(12) United States Patent
Steward et al.

(10) Patent No.: US 7,838,260 B2
(45) Date of Patent: *Nov. 23, 2010

(54) GFP-SNAP25 FLUORESCENCE RELEASE ASSAY FOR BOTULINUM TOXIN PROTEASE ACTIVITY

(75) Inventors: Lance E. Steward, Irvine, CA (US); Marcella A. Gilmore, Santa Ana, CA (US); Kei R. Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 345 days.

This patent is subject to a terminal disclaimer.

(21) Appl. No.: 12/019,120

(22) Filed: Jan. 24, 2008

(65) Prior Publication Data

US 2008/0213796 A1    Sep. 4, 2008

Related U.S. Application Data

(60) Division of application No. 10/917,844, filed on Aug. 13, 2004, now Pat. No. 7,374,896, which is a continuation of application No. 09/942,098, filed on Aug. 28, 2001, now Pat. No. 7,332,567.

(51) Int. Cl.
*G01N 33/554* (2006.01)
*G01N 33/53* (2006.01)
*G01N 33/569* (2006.01)
*C12Q 1/37* (2006.01)
*C12Q 1/06* (2006.01)

(52) U.S. Cl. .................. 435/7.32; 435/7.72; 435/23; 435/39

(58) Field of Classification Search .................. None
See application file for complete search history.

(56) References Cited

U.S. PATENT DOCUMENTS

| | | |
|---|---|---|
| 5,693,476 A | 12/1997 | Scheller |
| 5,804,604 A | 9/1998 | Frankel et al. |
| 5,962,637 A | 10/1999 | Shone et al. |
| 5,965,699 A | 10/1999 | Schmidt et al. |
| 5,981,200 A | 11/1999 | Tsien et al. |
| 5,989,545 A | 11/1999 | Foster et al. |
| 6,043,042 A | 3/2000 | Shone et al. |
| 6,169,074 B1 | 1/2001 | Montal et al. |
| 6,197,534 B1 | 3/2001 | Lakowicz et al. |
| 6,221,355 B1 | 4/2001 | Dowdy |
| 6,504,006 B1 | 1/2003 | Shine et al. |
| 6,762,280 B2 | 7/2004 | Schmidt et al. |
| 7,183,066 B2 * | 2/2007 | Fernandez-Salas et al. . 435/7.32 |
| 7,208,285 B2 * | 4/2007 | Steward et al. .............. 435/7.32 |
| 7,332,567 B2 * | 2/2008 | Steward et al. .............. 530/300 |
| 7,399,607 B2 * | 7/2008 | Williams et al. .............. 435/23 |
| 7,419,676 B2 * | 9/2008 | Dolly et al. .............. 424/239.1 |
| 7,422,877 B2 * | 9/2008 | Dolly et al. ................. 435/69.1 |
| 7,495,069 B2 * | 2/2009 | Steward et al. .............. 530/300 |
| 7,514,088 B2 * | 4/2009 | Steward et al. ............ 424/239.1 |
| 7,556,817 B2 * | 7/2009 | Steward et al. ............ 424/239.1 |
| 7,632,655 B2 * | 12/2009 | Williams et al. .............. 435/23 |
| 7,635,574 B2 * | 12/2009 | Williams et al. .............. 435/23 |
| 7,638,294 B2 * | 12/2009 | Williams et al. .............. 435/23 |
| 7,645,570 B2 * | 1/2010 | Fernandez-Salas et al. ..... 435/4 |
| 7,674,601 B2 * | 3/2010 | Williams et al. .............. 435/23 |
| 7,678,550 B1 * | 3/2010 | Steward et al. .............. 435/7.32 |
| 7,709,608 B2 * | 5/2010 | Steward et al. .............. 530/350 |
| 7,718,766 B2 * | 5/2010 | Steward et al. .............. 530/300 |
| 7,749,759 B2 * | 7/2010 | Fernandez-Salas et al. .. 435/325 |
| 2003/0027752 A1 | 2/2003 | Steward et al. |
| 2003/0077685 A1 | 4/2003 | Schmidt et al. |
| 2003/0143650 A1 | 7/2003 | Steward et al. |
| 2003/0143651 A1 | 7/2003 | Steward et al. |
| 2003/0219462 A1 | 11/2003 | Steward et al. |
| 2004/0072270 A1 | 4/2004 | Fernandez-Salas et al. |
| 2004/0115727 A1 | 6/2004 | Steward et al. |
| 2004/0146963 A1 | 7/2004 | Schmidt et al. |
| 2005/0100973 A1 | 5/2005 | Steward et al. |

(Continued)

FOREIGN PATENT DOCUMENTS

WO      WO 95/33850 A1    12/1995

(Continued)

OTHER PUBLICATIONS

U.S. Appl. No. 11/752,596, filed May 2007, Steward et al.
U.S. Appl. No. 11/753,304, filed May 2007, Steward et al.
U.S. Appl. No. 11/754,046, filed May 2007, Steward et al.
U.S. Appl. No. 11/780,538, filed Jul. 2007, Steward et al.
Adams et al., "New biarsenical ligands and tetracysteine motifs for protein labeling in vitro and in vivo: Synthesis and biological applications," J. Am. Chem. Soc. 124(21):6063-6076 (2002).
Anne et al., "High-Throughput Fluorogenic Assay for Determination of Botulinum Type B Neurotoxin Protease Activity," Anal. Biochem. 291:253-261 (2001).

(Continued)

*Primary Examiner*—N. M Minnifield
(74) *Attorney, Agent, or Firm*—Kenton Abel; Debra Condino

(57) ABSTRACT

The present invention provides a nucleic acid molecule which contains a nucleotide sequence encoding a SNAP-25 substrate which includes (i) a green fluorescent protein; (ii) a first partner of an affinity couple; and (iii) a portion of SNAP-25 that includes a BoNT/A, BoNT/C1 or BoNT/E recognition sequence containing a cleavage site, where the cleavage site intervenes between the green fluorescent protein and the first partner of the affinity couple. Further provided herein is a nucleic acid molecule which contains a nucleotide sequence encoding a tagged toxin substrate which includes (i) a fluorescent protein; (ii) a first partner of an affinity couple; and (iii) a clostridial toxin recognition sequence containing a cleavage site, where the cleavage site intervenes between the fluorescent protein and the first partner of the affinity couple.

26 Claims, 25 Drawing Sheets

U.S. PATENT DOCUMENTS

| | | | |
|---|---|---|---|
| 2006/0063321 A1* | 3/2006 | Sasaki | 438/199 |
| 2006/0154314 A9 | 7/2006 | Steward et al. | |
| 2006/0233836 A1* | 10/2006 | Kincaid et al. | 424/239.1 |
| 2007/0122858 A1* | 5/2007 | Fernandez-Salas et al. | 435/7.32 |
| 2007/0243565 A1 | 10/2007 | Williams et al. | |
| 2007/0275477 A1 | 11/2007 | Gilmore et al. | |
| 2007/0292920 A1 | 12/2007 | Lin et al. | |
| 2008/0032318 A1* | 2/2008 | Steward et al. | 435/7.32 |
| 2009/0208993 A1* | 8/2009 | Fournie-Zaluski et al. | 435/24 |
| 2010/0055727 A1* | 3/2010 | Steward et al. | 435/23 |
| 2010/0069610 A1* | 3/2010 | Steward et al. | 530/350 |
| 2010/0075357 A1* | 3/2010 | Steward et al. | 435/18 |
| 2010/0075358 A1* | 3/2010 | Steward et al. | 435/23 |
| 2010/0081157 A1* | 4/2010 | Steward et al. | 435/23 |
| 2010/0081158 A1* | 4/2010 | Steward et al. | 435/23 |
| 2010/0151494 A1* | 6/2010 | Steward et al. | 435/7.4 |

FOREIGN PATENT DOCUMENTS

| | | |
|---|---|---|
| WO | WO 97/34620 A1 | 9/1997 |
| WO | WO 99/29721 A1 | 6/1999 |
| WO | WO 99/55899 A1 | 11/1999 |
| WO | WO 00/34308 A2 | 6/2000 |
| WO | WO 01/18038 A2 | 3/2001 |
| WO | WO 02/25284 A2 | 3/2002 |
| WO | WO 03/020948 A2 | 3/2003 |
| WO | WO 2004/031355 A2 | 4/2004 |
| WO | WO 2004/031773 A1 | 4/2004 |
| WO | WO 2005/076785 * | 8/2005 |
| WO | WO 2006/107921 * | 10/2006 |
| WO | WO 2007/106115 A1 | 9/2007 |
| WO | WO 2007/106799 A2 | 9/2007 |
| WO | WO 2009/035476 A1 * | 3/2009 |

OTHER PUBLICATIONS

Ausubel et al. Current Protocols in Molecular Biology, John Wiley & Sons, Inc.: New York (2000) 10.15, Supplement 41.

Ausubel et al., Current Protocols in Molecular Biology, John Wiley & Sons, Inc.: New York (2000), Chapter 16.6.

U.S. Appl. No. 11/780,958, filed Jul. 2007, Steward et al.
U.S. Appl. No. 11/780,925, filed Jul. 2007, Steward et al.
U.S. Appl. No. 11/780,872, filed Jul. 2007, Steward et al.
U.S. Appl. No. 11/780,092, filed Jul. 2007, Steward et al.
U.S. Appl. No. 12/018,637, filed Jan. 2008, Steward et al.
U.S. Appl. No. 12/019,070, filed Jan. 2008, Steward et al.

Ausubel et al., Current Protocols in Molecular Biology, John Wiley & Sons, Inc.: New York (2000), Chapter 16.7.

Autofluorescent Proteins, AFP's Applications Manual, Carlsbad, CA: Qbiogene, pp. 1-25 (Nov. 1998).

Bark, "Structure of the chicken gene for SNAP-25 reveals duplicated exon encoding distinct isoforms of the protein ," J. Mol. Biol. 233(1):67-76 (1993).

BD Biosciences Clontech Product List, BD Living Colors™ Fluorescent Proteins, pp. 1-9 (Apr. 2004).

Blasi et al., "Botulinum neurotoxin C1 blocks neurotransmitter release by means of cleaving HPC-1/syntaxin," EMBO J. 12(12):4821-4828 (1993).

Bronstein et al., "Chemiluminescent and bioluminescent reporter gene assays," Anal. Biochem. 219:169-181 (2001).

Burnett et al., "Novel small molecule inhibitors of botulinum neurotoxin A metalloprotease activity," Biochem. Biophys. Res. Commun. 310(1):84-93 (2003).

Calbiochem, "SNAPtide® Botulinum Toxin A Substrate, Fluorogenic," www.calbiochem.com, printed on Dec. 17, 2002.

Catsicas et al., "Expression of a conserved cell-type-specific protein in nerve terminals coincides with synaptogenesis ," Proc. Natl. Acad. Sci. U.S.A. 88(3):785-789 (1991).

Clegg, "Fluorescence Resonance Energy Transfer," Curr. Opin. Biotechnol. 6:103-110 (1995).

Collins, "Generation and initial analysis of more than 15,000 full-length human and mouse cDNA sequences," Proc. Natl. Acad. Sci. U.S.A. 99(26):16899-16903 (2002).

Cornille et al., "Solid-Phase Synthesis, Conformational Analysis and In Vitro Cleavage of Synthetic Human Synaptobrevin II 1-93 by Tetanus Toxin L Chain," Eur. J. Biochem. 222:173-181 (1994).

Criado et al. "A single amino acid near the C terminus of the synaptosomeassociated protein of 25 kDa (SNAP-25) is essential for exocytosis in chromaffin cells," Proc. Natl. Acad. Sci. U.S.A. 96(13):7256-7261 (1999).

Deloukas et al., "The DNA sequence and comparative analysis of human chromosome 20," Nature 414(6866):865-871 (2001).

Ekong et al., "Recombinant SNAP-25 is an Effective Substrate for Clostridium botulinum Type A Toxin Endopeptidase Activity in vitro," Microbiology 143:3337-3347 (1997).

Ekong et al., "An alternative bioassay for botulinum neurotoxin type A based on its endopeptidase activity," Dev. Animal Vet. Sci. 27:1039-1044 (1997).

Ellenberg et al., "Two-color green fluorescent protein time-lapse imaging," Biotechniques 25(5):838-842, 844-846 (1998).

Enzelberger et al., "Designing new metal affinity peptides by random mutagenesis of a natural metal-binding site," J. Chromatogr. A. 898(1):83-94 (2000).

Fernandez-Salas et al, "Plasma membrane localization signals in the light chain of botulinum neurotoxin", PNAS, vol. 101, No. 9, Mar. 2, 1994, pp. 3208-3213.

Florentin et al., "A Highly Sensitive Fluorometric Assay for 'Enkephalinase,' a Neutral Metalloendopeptidase That Releases Tyrosine-Glycine-Glycine from Enkepahlins," Analytical Biochemistry 141:62-69 (1984).

Foran et al., "Differences in the Protease Activities of Tetanus and Botulinum B Toxins Revealed by the Cleavage of Vesicle-Associated Membrane Protein and Various Sized Fragments," Biochemistry 33:15365-15374 (1994).

Foran et al., "Botulinum neurotoxin C1 cleaves both syntaxin and SNAP-25 in intact and permeabilized chromaffin cells: Correlation with its blockade of catecholamine release," Biochemistry 35(8):2630-2636 (1996).

Geoghegan et al., "Fluorescence-based Continuous Assay for the Aspartyl Protease of Human Immunodeficiency Virus-1," FEBS 262:119-122 (1990).

Gil et al., "Modifications in the C terminus of the synaptosome-associated protein of 25 kDa (SNAP-25) and in the complementary region of synaptobrevin affect the final steps of exocytosis," J. Biol. Chem. 277(12):9904-9910 (2002).

Goudreau et al., "Dns-Gly-(p-NO2)Phe-Ala, a Specific Fluorogenic Substrate for Neutral Endopeptidase 24.11," Analytical Biochemistry 219:87-95 (1994).

Graham et al., "A method to measure the interaction of Rac/Cdc42 with their binding partners using fluorescence resonance energy transfer between mutants of green fluorescent protein," Analytical Biochem. 296:208-217 (2001).

Griesbeck et al., "Reducing the environmental sensitivity of yellow fluorescent protein. Mechanism and applications," J. Biol. Chem. 276(31):29188-29194 (2001).

Grisshammer and Tucker, "Quantitative evaluation of neurotensin receptor purification by immobilized metal affinity chromatography," Prot. Expr. Purif. 11:53-60 (1997).

Hallis et al., "Development of Novel Assays for Botulinum Type A and B Neurotoxins Based on Their Endopeptidase Activities," J. Clin. Microbiol. 34:1934-1938 (1996).

Hanson and Stevens, "Cocrystal Structure of Synaptobrevin-II Bound to Botulinum Neurotoxin Type B at 2.0 Å Resolution," Nature Structural Biology 7:687-692 (2000).

Heim and Tsien, "Engineering green fluorescent protein for improved brightness, longer wavelengths and fluorescence resonance energy transfer," Curr. Biol. 6(2):178-182 (1996).

Heim et al., "Wavelength mutations and posttranslational autoxidation of green fluorescent protein," Proc Natl Acad Sci U S A. 91(26):12501-12504 (1994).

Hess et al., "The 25 kDa synaptosomal-associated protein SNAP-25 is the major methionine-rich polypeptide in rapid axonal transport and a major substrate for palmitoylation in adult CNS," J. Neurosci. 12(12):4634-4641 (1992).

Heyduk, "Measuring protein conformational changes by FRET/LRET," Curr. Opin. Biotechnol. 13:292-296 (2002).

Hodel, "Molecules in Focus: SNAP-25," Int. J. Biochem. & Cell Biol. 30:1069-1073 (1998).

Holskin et al., "A Continuous Fluorescence-Based Assay of Human Cytomegalovirus Protease Using a Peptide Substrate," Analytical Biochemistry 226:148-155 (1995).

Huang et al., "Ca2+ influx and cAMP elevation overcame botulinum toxin A but not tetanus toxin inhibition of insulin exocytosis," Am. J. Physiol. Cell Physiol. 281:C740-C750 (2001).

Humeau et al., "How Botulinum and Tetanus Neurotoxins Block Neurotransmitter Release," Biochimie 82:427-446 (2000).

Jacobsson et al., "Differential subcellular localization of SNAP-25a and SNAP-25b RNA transcripts in spinal motoneurons and plasticity in expression after nerve injury," Brain Res. Mol. Brain Res. 37(1-2):49-62 (1996).

Jagadish et al., "Insulin-responsive tissues contain the core complex protein SNAP-25 (synaptosomal-associated protein 25) A and B isoforms in addition to syntaxin 4 and synaptobrevins 1 and 2," Biochem. J. 317(Pt 3):945-954 (1996).

Kakiuchi et al., "A High Throughput Assay of the Hepatitis C Virus Nonstructural Protein 3 Serine Proteinase," Journal of Virological Methods 80:77-84 (1999).

Kalandakanond and Coffield, "Cleavage of SNAP-25 by botulinum toxin type A requires receptor-mediated endocytosis, pH-dependent translocation, and zinc ," J. Pharmacol. Exp. Ther. 296(3):980-986 (2001).

Kam et al., "Probing molecular processes in live cells by quantitative multidimensional microscopy," Trends in Cell Biology 11:329-334 (2001).

Knapp et al., "The Crystal Structure of Botulinum Toxin A zinc Protease Domain" abstract of presentation, 37th Annual Meeting of the Interagency Botulism Research Coordinating Committee Asilomar, CA (2000).

Lacy et al., "Crystal Structure of Botulinum Neurotoxin Type A and Implications for Toxicity," Nature Structural Biology 5:898-902 (1998).

Le Bonniec et al., "Characterization of the P2' and P3' Specificities of Thrombin Using Fluorescence-Quenched Substrates and Mapping of the Subsites by Mutagenesis," Biochemistry 35:7114-7122 (1996).

Lippincott-Schwartz and Patterson, "Development and use of fluorescent protein markers in living cells," Science 300:87-91 (2003).

List Biological Laboratories, "SNAPtide for Fluorometric Measurement of Botulinum Toxin Type A Activity," www.listlabs.com, printed on Dec. 23, 2002.

List Biological Laboratories, Inc., "Botulinum Neurotoxins," web page: http://www.listlabs.com/Literature/130.htm (Printed: Dec. 10, 2004).

List Biological Laboratories, Inc., "What's new?," web page: http://www.listlabs.com/listopener.htm (Printed: Dec. 9, 2004).

Mahajan et al., "Novel Mutant Green Fluorescent Protein Protease Substrates Reveal the Activation of Specific Caspases During Apoptosis," Chemistry & Biology 6:401-409 (1999).

Matayoshi et al., "Novel Fluorogenic Substrates for Assaying Retroviral Proteases by Resonance Energy Transfer," Science 247:954-958 (1990).

Matsumoto et al., "A High-Throughput Screening Utilizing Intramolecular Fluorescence Resonance Energy Transfer for the Discovery of the Molecules that Bind HIV-1 TAR RNA Specifically," Bioorganic & Medicinal Chemistry Letters 10:1857-1861 (2000).

Mohanty and Weiner, "Membrane protein expression and production: Effects of polyhistidine tag length and position," Protein Expr. Purif 33:311-325 (2004).

Molecular Probes, "Section 10.4—Detecting Peptidases and Proteases," Molecular Probes Handbook, web page http://www.probes.com/handbook/sections/1004.html Updated Aug. 3, 2003.

Montecucco and Schiavo, "Structure and Function of Tetanus and Botulinum Neurotoxins," Quarterly Reviews of Biophysics 28:423-472 (1995).

Nagai et al., "A variant of yellow fluorescent protein with fast and efficient maturation for cell-biological applications," Nat. Biotechnol. 20(1):87-90 (2002).

Neale et al., "Botulinum neurotoxin A blocks synaptic vesicle exocytosis but not endocytosis at the nerve terminal," J. Cell Biology 147:1249-1260 (1999).

Niemann et al., "Clostridial Neurotoxins: New Tools for Dissecting Exocytosis," Trends in Cell Biology 4:179-185 (1994).

Olsen et al., "High-throughput Screening of Enzyme Libraries," Curr. Opin. Biotechnol. 11:331-337 (2000).

Ormo et al. "Crystal structure of the Aequorea victoria green fluorescent protein," Science 273(5280):1392-1395 (1996).

Oyler et al., "The identification of a novel synaptosomal-associated protein, SNAP-25, differentially expressed by neuronal subpopulations ," J. Cell Biol. 109 (6, Pt. 1):3039-3052 (1989).

Pellizzari et al., "Tetanus and Botulinum Neurotoxins: Mechanism of Action and Therapeutic Uses," Phil. Trans. R. Soc. Lond. 354:259-268 (1999).

Perpetuo et al., "Development of an operational synaptobrevin-based fluorescent substrate for tetanus neurotoxin quantification," Biotechnol. Appl. Biochem. 36:155-161 (2002).

Plafker and Macara, "Fluorescence resonance energy transfer biosensors that detect Ran conformational changes and a Ran•GDP-importin-β-RanBP1 complex in vitro and in intact cells," J. Biol. Chem. 277(33):30121-30127 (2002).

Risinger and Larhammar, "Multiple loci for synapse protein SNAP-25 in the tetraploid goldfish," Proc. Natl. Acad. Sci. U.S.A. 90(22):10598-10602 (1993).

Risinger et al., "Cloning of two loci for synapse protein Snap25 in zebrafish: Comparison of paralogous linkage groups suggests loss of one locus in the mammalian lineage ," J. Neurosci. Res. 54:563-573 (1998).

Rossetto et al., "Tetanus and Botulinum Neurotoxins: Turning Bad Guys Into Good by Research," Toxicon 39:27-41 (2001).

Schiavo et al., "Botulinum neurotoxin type C cleaves a single Lys-Ala bond within the carboxyl-terminal region of syntaxins," J. Biol. Chem. 270(18):10566-10570 (1995).

Schiavo et al, "Botulinum neurotoxins serotypes A and E cleave SNAP-25 at distinct COOH-terminal peptide bonds", FEBS Letters, vol. 335, No. 1, Nov. 1993, pp. 99-103 XP-002976174.

Schmidt and Bostian, "Endoproteinase Activity of Type A Botulinum Neurotoxin: Substrate Requirements and Activation by Serum Albumin," J. Protein Chem. 16(1):19-26 (1997).

Schmidt and Bostian, "Proteolysis of Synthetic Peptides by Type A Botulinum Neurotoxin," J. Protein Chem. 14(8):703-708 (1995).

Schmidt and Skerra, "The random peptide library-assisted engineering of a C-terminal affinity peptide, useful for the detection and purification of a functional Ig Fv fragment," Protein Eng. 6(1):109-122 (1993).

Schmidt and Stafford, "A high-affinity competitive inhibitor of type A botulinum neurotoxin protease activity," FEBS Lett. 532(3):423-426 (2002).

Schmidt and Stafford, "Fluorigenic substrates for the protease activities of botulinum neurotoxins, serotypes A, B, and F," Appl. Environ. Microbiol. 69(1):297-303 (2003); Erratum in: Appl Environ Microbiol. 69(5):3025. (May 2003).

Schmidt et al., "High-throughput assays for botulinum neurotoxin proteolytic activity: Serotypes A, B, D, and F," Analytical Biochem. 296:130-137 (2001).

Schmidt et al., "Type A Botulinum Neurotoxin Proteolytic Activity: Development of Competitive Inhibitors and Implications for Substrate Specificity at the S1' Binding Subsite," FEBS Lett. 435:61-64 (1998).

Selvin, "The Renaissance of Fluorescence Resonance Energy Transfer," Nature Structural Biology 7(9):730-734 (2000).

Selvin, "Fluorescence resonance energy transfer," Methods Enzymol. 246:300-334 (1995).

Shine et al., "Sensitive method for detection of botulinum toxin type A," abstract, The 38th Interagency Botulism Research Coordinating Committee Meeting, Easton, Maryland, Oct. 17-19, 2001.

Shine et al., "A continuous fluorimetric assay for high-throughput screening for botulinum toxin type a inhibitors," Naunyn Schmiedebergs Arch. Pharmacol. 365(Supp. 2):R40 (Jun. 2002).

Shone et al., "Proteolytic Cleavage of Synthetic Fragments of Vesicle-Associated Membrane Protein, Isoform-2 by Botulinum Type B Neurotoxin," Eur. J. Biochem. 217:965-971 (1993).

Siegel R. et al, "Measurement of molecular interactions in living cells by fluorescence resonance energy transfer between variants of green fluorescent protein", STKE, Jun. 27, 2000, pp. 1-6.

Sigma Genosys, "Strep-Tag II Protein Expression and Purification System," web page: http://www.sigma-genosys.com/molbio_strep_generalinfo.asp date printed Aug. 5, 2004.

Sittampalam et al., "High-Throughput Screening: Advances in Assay Technologies," Current Opinion in Chemical Biology 1:384-391 (1997).

Smith, "Purification of gluthation-S-transferase fusion proteins," Methods Mol. Cell Biol. 4:220-229 (1993).

Swaminathan and Eswaramoorthy, "Structural Analysis of the Catalytic and Binding Sites of Clostridium botulinum Neurotoxin B," Nature Structural Biology 7:693-699 (2000).

Tawa et al., "Quantitative Analysis of Fluorescent Caspase Substrate Cleavage in Intact Cells and Identification of Novel Inhibitors of Apoptosis," Cell Death and Differentiation 8:30-37 (2001).

Vadakkanchery V. et al, "Proteolysis of SNAP-25 isoforms by botulinum neurotoxin types A, C, and E: Domains and amino acid residues controlling the formation of enzyme-substrate complexes and cleavage", J. Neurochem, vol. 72, 1999, pp. 327-337.

Vaidyanathan et al., "Proteolysis of SNAP-25 Isoforms by Botulinum Neurotoxin Types A, C and E: Domains and Amino Acid Residues Controlling the Formation of Enzyme-Substrate Complexes and Cleavage," J. Neurochem. 72:327-337 (1999).

Wang et al., "A Continuous Fluorescence Assay of Renin Activity," Analytical Biochemistry 210:351-359 (1993).

Wu and Brand, "Resonance Energy Transfer: Methods and Applications," Analytical Biochemistry 218:1-13 (1994).

Xia and Liu, "Reliable and global measurement of fluorescence resonance energy transfer using fluorescence microscopes," Biophys. J. 81(4):2395-2402 (2001).

Xia et al., "Stable SNARE complex prior to evoked synaptic vesicle fusion revealed by fluorescence resonance energy transfer," J. Biol. Chem. 276:1766-1771 (2001).

Yamasaki et al., "Cleavage of Members of the Synaptobrevin/VAMP Family by Types D and F Botulinal Neurotoxins and Tetanus Toxin," J. Biol. Chem. 269:12764-12772 (1994).

Zhang et al., "Creating new fluorescent probes for cell biology," Nat. Rev. Mol. Cell Biol. 3(12):906-918 (2002).

Zhao et al., "Cloning and sequence analysis of the human SNAP25 cDNA," Gene 145(2):313-314 (1994).

Zimmer, "Green fluorescent protein (GFP): Applications, structure, and related photophysical behavior," Chem. Rev. 102(3):759-781 (2002).

Zlokarnik et al., "Quantitation of Transcription and Clonal Selection of Single Living Cells with β-Lactamase as Reporter," Science 279(5347):84-88 (1998).

* cited by examiner

```
                                        GFP
----------------------------------------------------------------------------------
 M   A   S     K  G  E     E  L  F     T  G  V     V  P  I     L  V  E     L  D  G
ATGGCTAGC   AAAGGAGAA   GAACTCTTC   ACTGGAGTT  GTCCCAATT   CTTGTTGAA   TTAGATGGT
                                        GFP
----------------------------------------------------------------------------------
 D   V   N     G  H  K     F  S  V     S  G  E     G  E  G     D  A  T     Y  G  K
GATGTTAAC   GGCCACAAG   TTCTCTGTC   AGTGGAGAG   GGTGAAGGT   GATGCAACA   TACGGAAAA
                                        GFP
----------------------------------------------------------------------------------
 L   T   L     K  F  I     C  T  T     G  K  L     P  V  P     W  P  T     L  V  T
CTTACCCTG   AAGTTCATC   TGCACTACT   GGCAAACTG   CCTGTTCCA   TGGCCAACA   CTAGTCACT
                                        GFP
----------------------------------------------------------------------------------
 T   L   C     Y  G  V     Q  C  F     S  R  Y     P  D  H     M  K  R     H  D  F
ACTCTGTGC   TATGGTGTT   CAATGCTTT   TCAAGATAC   CCGGATCAT   ATGAAACGG   CATGACTTT
                                        GFP
----------------------------------------------------------------------------------
 F   K   S     A  M  P     E  G  Y     V  Q  E     R  T  I     F  F  K     D  D  G
TTCAAGAGT   GCCATGCCC   GAAGGTTAT   GTACAGGAA   AGGACCATC   TTCTTCAAA   GATGACGGC
                                        GFP
----------------------------------------------------------------------------------
 N   Y   K     T  R  A     E  V  K     F  E  G     D  T  L     V  N  R     I  E  L
AACTACAAG   ACACGTGCT   GAAGTCAAG   TTTGAAGGT   GATACCCTT   GTTAATAGA   ATCGAGTTA
                                        GFP
----------------------------------------------------------------------------------
 K   G   I     D  F  K     E  D  G     N  I  L     G  H  K     L  E  Y     N  Y  N
AAAGGTATT   GACTTCAAG   GAAGATGGC   AACATTCTG   GGACACAAA   TTGGAATAC   AACTATAAC
                                        GFP
----------------------------------------------------------------------------------
 S   H   N     V  Y  I     M  A  D     K  Q  K     N  G  I     K  V  N     F  K  T
TCACACAAT   GTATACATC   ATGGCAGAC   AAACAAAAG   AATGGAATC   AAAGTGAAC   TTCAAGACC
                                        GFP
----------------------------------------------------------------------------------
 R   H   N     I  E  D     G  S  V     Q  L  A     D  H  Y     Q  Q  N     T  P  I
CGCCACAAC   ATTGAAGAT   GGAAGCGTT   CAACTAGCA   GACCATTAT   CAACAAAAT   ACTCCAATT
                                        GFP
----------------------------------------------------------------------------------
 G   D   G     P  V  L     L  P  D     N  H  Y     L  S  T     Q  S  A     L  S  K
GGCGATGGC   CCTGTCCTT   TTACCAGAC   AACCATTAC   CTGTCCACA   CAATCTGCC   CTTTCGAAA
                                        GFP
----------------------------------------------------------------------------------
 D   P   N     E  K  R     D  H  M     V  L  L     E  F  V     T  A  A     G  I  T
GATCCCAAC   GAAAAGAGA   GACCACATG   GTCCTTCTT   GAGTTTGTA   ACAGCTGCT   GGGATTACA
                                                                     Linker
                                                               ------------------
            GFP
--------------------------                                           ------
 H   G   M     D  E  L     Y  N  G     A  G     S  G  A     G  G  G     G  I  R
CATGGCATG   GATGAACTG   TACAACGGC   GGTGCAGGA   TCCGGTGCG   GGTGGCGGT   GGCATCCGG
                                     SNAP25(134-206)
----------------------------------------------------------------------------------
 R   V   T     N  D  A     R  E  N     E  M  D     E  N  L     E  Q  V     S  G  I
AGGGTAACA   AACGATGCC   CGGGAAAAT   GAGATGGAT   GAGAACCTG   GAGCAGGTG   AGCGGCATC
                                     SNAP25(134-206)
----------------------------------------------------------------------------------
 I   G   N     L  R  H     M  A  L     D  M  G     N  E  I     D  T  Q     N  R  Q
ATCGGAAAC   CTCCGCCAT   ATGGCTCTA   GACATGGGC   AATGAGATT   GACACCCAG   AATCGCCAG
                                     SNAP25(134-206)
----------------------------------------------------------------------------------
 I   D   R     I  M  E     K  A  D     S  N  K     T  R  I     D  E  A     N  Q  R
ATCGACAGG   ATCATGGAG   AAGGCTGAT   TCCAACAAA   ACCAGAATT   GATGAAGCC   AACCAACGT
                                        Linker
                                    ----------------
    SNAP25(134-206)                                         6xHis Tag
--------------------                                        ----------------------
 A   T   K     M  L  G     S  G  G     G  G  G     H  H  H     H  H  H     *
GCAACAAAG   ATGCTGGGA   AGTGGTGGC   GGTGGCGGC   CATCACCAT   CACCATCAC   TAA
```

Figure 9B

```
                BirA-PolyHis
------------------------------------------------
  M   A   S   G   G   L   N   D   I   F   E   A   Q   K   I   E   W   H   G   S   H
ATGGCTAGC GGAGGACTG AACGACATC TTCGAGGCT CAAAAGATC GAGTGGCAT GGATCCCAT
                                     SNAP25(134-206)
                                     ------------------------------------------------
   BirA-PolyHis
-------------------------
  H   H   H   H   H   H   H   I   R   R   V   T   N   D   A   R   E   N   E   M   D
CATCATCAT CATCATCAT CATATCCGG AGGGTAACA AACGATGCC CGGGAAAAT GAGATGGAT
                  SNAP25(134-206)

E   N   L   E   Q   V   S   G   I   I   G   N   L   R   H   M   A   L   D   M   G
GAGAACCTG GAGCAGGTG AGCGGCATC ATCGGAAAC CTCCGCCAT ATGGCTCTA GACATGGGC
                  SNAP25(134-206)

N   E   I   D   T   Q   N   R   Q   I   D   R   I   M   E   K   A   D   S   N   K
AATGAGATT GACACCCAG AATCGCCAG ATCGACAGG ATCATGGAG AAGGCTGAT TCCAACAAA
                                                                              Linker
                                                                          -------------
            SNAP25(134-206)
-----------------------------------------------------------
  T   R   I   D   E   A   N   Q   R   A   T   K   M   L   G   S   G   G   G   G   S
ACCAGAATT GATGAAGCC AACCAACGT GCAACAAAG ATGCTGGGA AGTGGTGGC GGTGGTAGC
                                                                 GFP
                                                                 ------------------------------------------
   Linker
-------------
  G   T   G   G   A   S   K   G   E   E   L   F   T   G   V   V   P   I   L   V   E
GGCACCGGT GGCGCTAGC AAAGGAGAA GAACTCTTC ACTGGAGTT GTCCCAATT CTTGTTGAA
                                                  GFP L   D   G   D   V   N   G   H   K   F   S   V   S   G   E   G   E   G   D   A   T
TTAGATGGT GATGTTAAC GGCCACAAG TTCTCTGTC AGTGGAGAG GGTGAAGGT GATGCAACA
                                                  GFP Y   G   K   L   T   L   K   F   I   C   T   T   G   K   L   P   V   P   W   P   T
TACGGAAAA CTTACCCTG AAGTTCATC TGCACTACT GGCAAACTG CCTGTTCCA TGGCCAACA
                                                  GFP L   V   T   T   L   C   Y   G   V   Q   C   F   S   R   Y   P   D   H   M   K   R
CTAGTCACT ACTCTGTGC TATGGTGTT CAATGCTTT TCAAGATAC CCGGATCAT ATGAAACGG
                                                  GFP H   D   F   F   K   S   A   M   P   E   G   Y   V   Q   E   R   T   I   F   F   K
CATGACTTT TTCAAGAGT GCCATGCCC GAAGGTTAT GTACAGGAA AGGACCATC TTCTTCAAA
                                                  GFP D   D   G   N   Y   K   T   R   A   E   V   K   F   E   G   D   T   L   V   N   R
GATGACGGC AACTACAAG ACACGTGCT GAAGTCAAG TTTGAAGGT GATACCCTT GTTAATAGA
                                                  GFP I   E   L   K   G   I   D   F   K   E   D   G   N   I   L   G   H   K   L   E   Y
ATCGAGTTA AAAGGTATT GACTTCAAG GAAGATGGC AACATTCTG GGACACAAA TTGGAATAC
                                                  GFP N   Y   N   S   H   N   V   Y   I   M   A   D   K   Q   K   N   G   I   K   V   N
AACTATAAC TCACACAAT GTATACATC ATGGCAGAC AAACAAAAG AATGGAATC AAAGTGAAC
                                                  GFP F   K   T   R   H   N   I   E   D   G   S   V   Q   L   A   D   H   Y   Q   Q   N
TTCAAGACC CGCCACAAC ATTGAAGAT GGAAGCGTT CAACTAGCA GACCATTAT CAACAAAAT
                                                  GFP T   P   I   G   D   G   P   V   L   L   P   D   N   H   Y   L   S   T   Q   S   A
ACTCCAATT GGCGATGGC CCTGTCCTT TTACCAGAC AACCATTAC CTGTCCACA CAATCTGCC
                                                  GFP L   S   K   D   P   N   E   K   R   D   H   M   V   L   L   E   F   V   T   A   A
CTTTCGAAA GATCCCAAC GAAAAGAGA GACCACATG GTCCTTCTT GAGTTTGTA ACAGCTGCT
                  GFP
-------------------------------------
  G   I   T   H   G   M   D   E   L   Y   N   *
GGGATTACA CATGGCATG GATGAACTG TACAACTGA
```

GFP-SNAP25 Assay of Native Pure A

Pure A (pM)
(150 kDa native BoNT/A dichain)

GFP-SNAP25 Assay of Native Single Chain BoNT/E

Figure 12A

GFP-SNAP Assay of Native BoNT/E Dichain

Figure 12B

GFP-SNAP25 assay of BoNT/C Complex

Figure 12C

GFP-SNAP25 FLUORESCENCE RELEASE ASSAY FOR BOTULINUM TOXIN PROTEASE ACTIVITY

This application is a divisional and claims priority pursuant to 35 U.S.C. §120 to U.S. patent application Ser. No. 10/917,844, filed Aug. 13, 2004, now U.S. Pat. No. 7,374,896 a continuation application that claims priority pursuant to 35 U.S.C. §120 to U.S. patent application Ser. No. 09/942,098, filed Aug. 28, 2001, now U.S. Pat. No. 7,332,567 each of which is hereby incorporated by reference in its entirety.

The present invention relates generally to protease assays, and more specifically, to recombinantly produced substrates and methods for assaying protease activity of clostridial toxins such as botulinum toxins and tetanus toxins.

The neuroparalytic syndrome of tetanus and the rare but potentially fatal disease, botulism, are caused by neurotoxins produced by bacteria of the genus *Clostridium*. These clostridial neurotoxins are highly potent and specific poisons of neural cells, with the human lethal dose of the botulinum toxins on the order of micrograms. Thus, the presence of even minute levels of botulinum toxins in foodstuffs represents a public health hazard that must be avoided through rigorous testing.

However, in spite of their potentially deleterious effects, low controlled doses of botulinum neurotoxins have been successfully used as therapeutics. These toxins have been used in the therapeutic management of a variety of focal and segmental dystonias, of strabismus and other conditions in which reversible depression of a cholinergic nerve terminal activity is desired. Established therapeutic uses of botulinum neurotoxins in humans include, for example, treatment of blepharospasm, hemifacial spasm, laringeal dysphonia, focal hyperhidrosis, hypersalivation, oromandibular dystonia, cervical dystonia, torticollis, strabismus, limbs dystonia, occupational cramps and myokymia (Rossetto et al., *Toxicon* 39:27-41 (2001)). Intramuscular injection of spastic tissue with small quantities of BoNT/A, for example, has been used effectively to treat spasticity due to brain injury, spinal cord injury, stroke, multiple sclerosis and cerebral palsy. Additional possible clinical uses of clostridial neurotoxins currently are being investigated.

Given the potential danger associated with small quantities of botulinum toxins in foodstuffs and the need to prepare accurate pharmaceutical formulations, assays for botulinum neurotoxins presently are employed in both the food and pharmaceutical industry. The food industry requires assays for botulinum neurotoxins in order to validate new food packaging methods and to ensure food safety. In addition, the growing clinical use of the botulinum toxins necessitates accurate assays for botulinum neurotoxin activity for product formulation as well as quality control. In both industries, a mouse lethality test currently is used to assay for botulinum neurotoxin activity. Unfortunately, this assay suffers from several drawbacks: cost due to the large numbers of laboratory animals required; lack of specificity; and the potential for inaccuracy unless large animal groups are used.

Thus, there is a need for new materials and methods for assaying for clostridial toxin protease activity. The present invention satisfies this need and provides related advantages as well.

The present invention provides methods of determining clostridial toxin protease activity by (a) treating with a sample, in solution phase under conditions suitable for clostridial toxin protease activity, a tagged toxin substrate containing (i) a fluorescent protein; (ii) a first partner of an affinity couple; and (iii) a clostridial toxin recognition sequence that includes a cleavage site which intervenes between the fluorescent protein and the first partner of the affinity couple, such that a fluorescent cleavage product is generated when clostridial toxin is present in the sample; (b) contacting the treated sample with a second partner of the affinity couple, thereby forming stable complexes containing the first and second partners of the affinity couple; and (c) assaying the presence or amount of the fluorescent cleavage product in the treated sample, thereby determining clostridial toxin protease activity. In one embodiment, the fluorescent cleavage product is separated from the stable complexes prior to assaying the presence or amount of the fluorescent cleavage product.

The present invention also provides a nucleic acid molecule containing a nucleotide sequence that encodes a SNAP-25 substrate which includes (i) a green fluorescent protein; (ii) a first partner of an affinity couple; and (iii) a portion of SNAP-25 that includes a BoNT/A, BoNT/C1 or BoNT/E recognition sequence containing a cleavage site which intervenes between the green fluorescent protein and the first partner of the affinity couple. The present invention additionally provides a nucleic acid molecule containing a nucleotide sequence that encodes a tagged toxin substrate which includes (i) a fluorescent protein; (ii) a first partner of an affinity couple; and (iii) a clostridial toxin recognition sequence containing a cleavage site that intervenes between the fluorescent protein and the first partner of the affinity couple.

BRIEF DESCRIPTION OF THE DRAWINGS

FIG. 6 shows an alignment of various VAMP proteins. Human VAMP-1 (SEQ ID NO: 96; GenBank accession g135093); human VAMP-2 (SEQ ID NO: 4; GenBank accession g135094); mouse VAMP-2 (SEQ ID NO: 17; GenBank accession g2501081); bovine VAMP (SEQ ID NO: 18; GenBank accession g89782); frog VAMP (SEQ ID NO: 19; GenBank accession g6094391); and sea urchin VAMP (SEQ ID NO: 20; GenBank accession g5031415) are depicted.

FIG. 12 shows endopeptidase activity of native BoNT/E single chain, native BoNT/E dichain and BoNT/C complex. (A) Endoprotease activity of native single chain BoNT/E toxin. (B) Endoprotease activity of native BoNT/E dichain (DC). (C) Endopeptidase activity of BoNT/C complex.

FIG. 13 shows proteolysis of the GFP-$SNAP25_{(134-206)}$ fusion protein substrate as well as substrate analogues containing mutations R198A and R180D in the scissile bonds.

FIG. 14 shows proteolysis of fusion protein substrates using crude cell lysates. (A) CODON PLUS® cell lysates. (B) Negative control TOP10® cell lysates.

FIG. 15 shows representative examples of data collected for kinetic analysis of rLC/A. The graph on the left shows the non-linear curves fit to data collected over the course of 7-hour reactions. The graph on the right shows the initial, linear segments of the non-linear plots; the slopes of these lines are the initial reaction rates at the specified substrate concentrations (RFU/min).

FIG. 16 shows a plot of preliminary data for 178 pM rLC/A activity, indicating that the $K_m$ is approximately 4.6 μM.

FIG. 17 shows a GFP-SNAP25 assay of two vials of BOTOX® (Botulinum toxin serotype A)

DETAILED DESCRIPTION

The invention provides nucleic acid molecules containing nucleotide sequences encoding SNAP-25 substrates and tagged toxin substrates useful for determining clostridial toxin protease activity, including botulinum toxins of all serotypes as well as tetanus toxins. The nucleic acid molecules of the invention are valuable, in part, because they can be used to conveniently prepare recombinant SNAP-25 substrates as well as tagged toxin substrates with a longer toxin recognition sequence, which can enhance binding affinity for the cognate clostridial toxin. Such recombinant SNAP-25 substrates and tagged toxin substrates can be utilized in simple screening assays which do not rely on animals and are useful for analyzing crude and bulk samples as well as highly purified dichain toxins or isolated clostridial toxin light chains. Furthermore, as disclosed herein, recombinant SNAP-25 substrates and tagged toxin substrates prepared from the nucleic acid molecules of the invention can be used to detect BoNT/A and BoNT/E at low picomolar concentrations, and to detect BoNT/C at low nanomolar concentrations.

The present invention further provides methods of determining clostridial toxin protease activity which are advantageous in that they can be sensitive, rapid and high-throughput and allow a solution phase proteolysis reaction. Unlike other assays, the methods of the invention combine analysis of a clostridial toxin substrate which has good affinity for its cognate toxin, resulting in an assay with high sensitivity, in a format in which the toxin protease activity is assayed in solution phase, allowing kinetic analyses of toxin activity. Alternative assays, such as those described in U.S. Pat. No. 6,762,280, have relied on an immobilized substrate, albeit one with good binding affinity for toxin. Additional assays have relied on high pressure liquid chromatography (HPLC) separation and, therefore, have not been amenable to a high-throughput format (U.S. Pat. No. 5,965,699), or have been lower sensitivity assays which relied on short peptide substrates with relatively poor binding characteristics (see, for example, Anne et al., *Anal. Biochem.* 291: 253-261 (2001)).

Thus, the present invention provides, in part, a nucleic acid molecule containing a nucleotide sequence that encodes a SNAP-25 substrate containing (i) a green fluorescent protein; (ii) a first partner of an affinity couple; and (iii) a portion of SNAP-25 which includes a BoNT/A, BoNT/C1 or BoNT/E recognition sequence containing a cleavage site, where the cleavage site intervenes between the green fluorescent protein and the first partner of the affinity couple. In a nucleic acid molecule of the invention, the encoded first partner of the affinity couple can be, without limitation, a histidine tag, glutathione-S-transferase, maltose-binding protein, biotinylation sequence, streptavidin, S peptide, S protein, or an epitope such as a FLAG, hemagluttinin, c-myc or AU1 epitope. In one embodiment, the encoded first partner of the affinity couple is a histidine tag.

Figure 1:
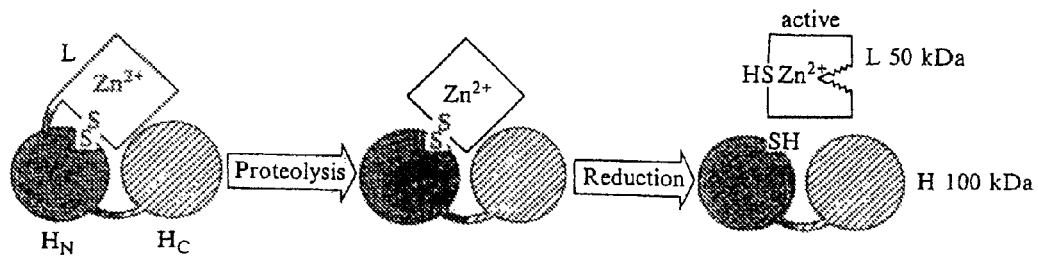
FIG. 1 shows a schematic of the deduced structure and postulated mechanism of activation of clostridial neurotoxins. Toxins can be produced as a single polypeptide chain of 150 kDa which is composed of three 50 kDa domains connected by loops. Selective proteolytic cleavage activates the toxins by generating two disulfide-linked chains: the L chain of 50 kDa and the H chain of 100 kDa, which is made up of two domains denoted $H_N$ and $H_C$. The three domains play distinct roles: the C-terminal domain of the heavy chain ($H_C$) functions in cell binding while the N-terminal domain of the heavy chain ($H_N$) permits translocation from endosome to cell cytoplasm. Following reduction of the disulfide linkage inside the cell, the zinc-endopeptidase activity of the L chain is liberated.

In a nucleic acid molecule of the invention, the encoded SNAP-25 substrate can include any of a variety of portions of SNAP-25 which have a BoNT/A, BoNT/C1 or BoNT/E recognition sequence containing a cleavage site. Such a portion of SNAP-25 can include, for example, residues 134 to 206 of SEQ ID NO: 90 or another BoNT/A, BoNT/C1 or BoNT/E recognition sequence and cleavage site disclosed herein or known in the art. In one embodiment, a nucleic acid molecule of the invention includes a nucleotide sequence encoding a SNAP-25 substrate which is cleaved with an activity of at least 1 nanomole/minute/milligram toxin. In another embodiment, a nucleic acid molecule of the invention includes a nucleotide sequence encoding a SNAP-25 substrate which is cleaved with an activity of at least 100 nanomoles/minute/milligram toxin. In a further embodiment, a nucleic acid molecule of the invention includes a nucleotide sequence encoding a SNAP-25 substrate which is cleaved with an activity of at least 1000 nanomoles/minute/milligram toxin.

The present invention further provides a nucleic acid molecule containing a nucleotide sequence encoding a tagged toxin substrate that contains (i) a fluorescent protein; (ii) a first partner of an affinity couple; and (iii) a clostridial toxin recognition sequence containing a cleavage site, where the cleavage site intervenes between the fluorescent protein and the first partner of the affinity couple. In a nucleic acid molecule encoding a tagged toxin substrate, the fluorescent protein can be, without limitation, a green fluorescent protein, blue fluorescent protein, cyan fluorescent protein, yellow fluorescent protein or red fluorescent protein. In one embodiment, a nucleic acid molecule of the invention includes a nucleotide sequence encoding a green fluorescent protein.

In such a nucleic acid molecule, a variety of first partners of an affinity couple can be incorporated into the encoded tagged toxin substrate. As non-limiting examples, an encoded tagged toxin substrate can include a histidine tag, glutathione-S-transferase, maltose-binding protein, biotinylation sequence, streptavidin, S peptide, S protein, or an epitope such as a FLAG, hemagluttinin, c-myc or AU1 epitope as the first partner of the affinity couple. Furthermore, the encoded clostridial toxin recognition sequence can be, without limitation, a portion of SNAP-25 such as residues 134 to 206 of SEQ ID NO: 90; or a BoNT/A, BoNT/B, BoNT/C1, BoNT/D, BoNT/E, BoNT/F, BoNT/G or TeNT recognition sequence such as, for example, one of the recognition sequences disclosed herein or known in the art.

Furthermore, a nucleic acid molecule of the invention contains a nucleotide sequence encoding a tagged toxin substrate which can be cleaved by cognate clostridial toxin with low or high activity. In one embodiment, a nucleic acid molecule of the invention encodes a tagged toxin substrate which can be cleaved with an activity of at least 1 nanomole/minute/milligram toxin. In another embodiment, a nucleic acid molecule of the invention encodes a tagged toxin substrate which can be cleaved with an activity of at least 100 nanomoles/minute/milligram toxin. In yet another embodiment, a nucleic acid molecule of the invention encodes a tagged toxin substrate which can be cleaved with an activity of at least 1000 nanomoles/minute/milligram toxin.

The invention additionally provides a nucleic acid molecule that contains a nucleotide sequence encoding a tagged toxin substrate that includes (i) a genetically encoded detectable marker; (ii) a first partner of an affinity couple; and (iii) a clostridial toxin recognition sequence containing a cleavage site, where the cleavage site intervenes between the genetically encoded detectable marker and the first partner of the affinity couple. In a nucleic acid molecule of the invention, the genetically encoded detectable marker can be, without limitation, luciferase, horseradish peroxidase, alkaline phosphatase or a fluorescent protein.

Any of a variety of first partners of an affinity couple can be combined with a genetically encoded detectable marker in a tagged toxin substrate encoded by a nucleic acid molecule of the invention. The encoded first partner of the affinity couple can be, for example, a histidine tag; glutathione-S-transferase; maltose-binding protein; biotinylation sequence such as BirAsp; streptavidin; S peptide; S protein; or an epitope such as a FLAG, hemagluttinin, c-myc or AU1 epitope. In one embodiment, a nucleic acid molecule of the invention encodes a tagged toxin substrate which includes a histidine tag as the first partner of the affinity couple.

Furthermore, any of a variety of encoded clostridial toxin recognition sequences can be combined with a genetically encoded detectable marker in a tagged toxin substrate encoded by a nucleic acid molecule of the invention. Such clostridial toxin recognition sequences include, yet are not limited to, botulinum toxin recognition sequences. As non-limiting examples, a clostridial toxin recognition sequence to be combined with a genetically encoded detectable marker in an encoded tagged toxin substrate can be a portion of SNAP-25 such as residues 134 to 206 of SEQ ID NO: 90; or a BoNT/A, BoNT/B, BoNT/C1, BoNT/D, BoNT/E, BoNT/F, BoNT/G or TeNT recognition sequences such as one of the recognition sequences disclosed herein or known in the art.

A nucleic acid molecule of the invention can encode a tagged toxin substrate which is cleaved by cognate clostridial toxin with low or high activity. In one embodiment, a nucleic acid molecule of the invention encodes a tagged toxin substrate which can be cleaved with an activity of at least 1 nanomole/minute/milligram toxin. In other embodiments, a nucleic acid molecule of the invention encodes a tagged toxin substrate which can be cleaved with an activity of at least 100 nanomoles/minute/milligram toxin or at least 1000 nanomoles/minute/milligram toxin.

Further provided herein is a SNAP-25 substrate which includes (i) a green fluorescent protein; (ii) a first partner of an affinity couple; and (iii) a portion of SNAP-25 that includes a BoNT/A, BoNT/C1 or BoNT/E recognition sequence containing a cleavage site, where the cleavage site intervenes between the green fluorescent protein and the first partner of the affinity couple. Any of a variety of first partners of an affinity couple are useful in a SNAP-25 substrate of the invention. As non-limiting examples, a first partner of an affinity couple can be a histidine tag, glutathione-S-transferase, maltose-binding protein, a biotinylation sequence, streptavidin, S peptide, S protein, or an epitope such as a FLAG, hemagluttinin, c-myc or AU1 epitope. In one embodiment, the invention provides a SNAP-25 substrate in which the first partner of the affinity couple is a histidine tag.

A SNAP-25 substrate of the invention incorporates a portion of SNAP-25 which includes a BoNT/A, BoNT/C1 or BoNT/E recognition sequence containing the corresponding cleavage site. In one embodiment, a SNAP-25 substrate of the invention includes residues 134 to 206 of SEQ ID NO: 90. In further embodiments, a SNAP-25 substrate of the invention includes a BoNT/A recognition sequence, a BoNT/C1 recognition sequence, or a BoNT/E recognition sequence. Furthermore, a SNAP-25 substrate of the invention can be cleaved, without limitation, with an activity of at least 1 nanomole/ minute/milligram toxin, at least 100 nanomoles/minute/milligram toxin, or at least 1000 nanomoles/minute/milligram toxin.

Further provided herein is a tagged toxin substrate which includes (i) a fluorescent protein; (ii) a first partner of an affinity couple; and (iii) a clostridial toxin recognition sequence containing a cleavage site, where the cleavage site intervenes between the fluorescent protein and the first partner of the affinity couple. Any of a variety of fluorescent proteins can be incorporated into a tagged toxin substrate of the invention, including, without limitation, green fluorescent proteins (GFPs), blue fluorescent proteins (BFPs), cyan fluorescent proteins (CFPs), yellow fluorescent proteins (YFPs) and red fluorescent proteins (RFPs). In one embodiment, a tagged toxin substrate of the invention includes a green fluorescent protein. Any of a variety of first partners of an affinity couple are useful in the tagged toxin substrates of the invention. As non-limiting examples, a tagged toxin substrate can include a histidine tag, glutathione-S-transferase, maltose-binding protein, a biotinylation sequence, streptavidin, S peptide, S protein, or an epitope such as a FLAG, hemagluttinin, c-myc or AU1 epitope as the first partner of the affinity couple. In one embodiment, the invention provides a tagged toxin substrate in which the first partner of the affinity couple is a histidine tag.

It is understood that a variety of recognition sequences are useful in the tagged toxin substrates of the invention, including, yet not limited to, botulinum toxin recognition sequences. In one embodiment, the invention provides a tagged toxin substrate in which the recognition sequence includes a portion of SNAP-25 such as, without limitation, residues 134 to 206 of SEQ ID NO: 90. In another embodiment, the invention provides a tagged toxin substrate in which the recognition sequence is a BoNT/A recognition sequence such as, without limitation, a BoNT/A recognition sequence including at least six consecutive residues of SNAP-25, where the six consecutive residues encompass the sequence Gln-Arg. In a further embodiment, the invention provides a tagged toxin substrate in which the recognition sequence is a BoNT/B recognition sequence such as, without limitation, a BoNT/B recognition sequence which includes at least six consecutive residues of VAMP, where the six consecutive residues encompass the sequence Gln-Phe. In still another embodiment, the invention provides a tagged toxin substrate in which the recognition sequence is a BoNT/C1 recognition sequence such as, without limitation, a BoNT/C1 recognition sequence which includes at least six consecutive residues of syntaxin, where the six consecutive residues encompass the sequence Lys-Ala, or a BoNT/C1 recognition sequence which includes at least six consecutive residues of SNAP-25, where the six consecutive residues encompass the sequence Arg-Ala. In still another embodiment, the invention provides a tagged toxin substrate in which the recognition sequence is a BoNT/D recognition sequence such as, without limitation, a BoNT/D recognition sequence including at least six consecutive residues of VAMP, where the six consecutive residues encompass the sequence Lys-Leu.

In yet another embodiment, the invention provides a tagged toxin substrate in which the recognition sequence is a BoNT/E recognition sequence such as, without limitation, a BoNT/E recognition sequence which includes at least six consecutive residues of SNAP-25, the six consecutive residues encompassing the sequence Arg-Ile. In a further embodiment, the invention provides a tagged toxin substrate in which the recognition sequence is a BoNT/F recognition sequence such as, without limitation, a BoNT/F recognition sequence including at least six consecutive residues of VAMP, the six consecutive residues encompassing the sequence Gln-Lys. The present invention additionally provides a tagged toxin substrate in which the recognition sequence is a BoNT/G recognition sequence such as, without limitation, a BoNT/G recognition sequence including at least six consecutive residues of VAMP, where the six consecutive residues encompass the sequence Ala-Ala. In still another embodiment, the invention provides a tagged toxin substrate in which the recognition sequence is a TeNT recognition sequence such as, without limitation, a TeNT recognition sequence which includes at least six consecutive residues of VAMP, where the six consecutive residues encompass the sequence Gln-Phe.

A tagged toxin substrate of the invention can be cleaved with high or low activity. In one embodiment, a tagged toxin substrate of the invention can be cleaved with an activity of at least 1 nanomole/minute/milligram toxin. In another embodiment, a tagged toxin substrate of the invention can be cleaved with an activity of at least 100 nanomoles/minute/milligram toxin. In still a further embodiment, a tagged toxin substrate of the invention can be cleaved with an activity of at least 1000 nanomoles/minute/milligram toxin.

Tetanus and botulinum neurotoxins are produced by Clostridia and cause the neuroparalytic syndromes of tetanus and botulism. While tetanus neurotoxin acts mainly at the CNS synapse, botulinum neurotoxins act peripherally. Clostridial neurotoxins share a similar mechanism of cell intoxication, blocking the release of neurotransmitters. In these toxins, which are composed of two disulfide-linked polypeptide chains, the larger subunit is responsible for neurospecific binding and translocation of the smaller subunit into the cytoplasm. Upon translocation and reduction in neurons, the smaller chain displays protease activity specific for protein components involved in neuroexocytosis in the neuronal cytosol. The SNARE protein targets of clostridial toxins are common to exocytosis in a variety of non-neuronal types; in these cells, as in neurons, light chain protease activity inhibits exocytosis.

Tetanus neurotoxin and botulinum neurotoxins B, D, F, and G specifically recognize VAMP (synaptobrevin), an integral protein of the synaptic vesicle membrane which is cleaved at distinct bonds depending on the neurotoxin. Botulinum A and E neurotoxins recognize and specifically cleave SNAP-25, a protein of the presynaptic membrane, at two different sites in the carboxy-terminal portion of the protein. Botulinum neurotoxin C1 cleaves syntaxin, a protein of the nerve plasmalemma, in addition to SNAP-25. The three protein targets of the Clostridial neurotoxins are conserved from yeast to humans, although cleavage sites and toxin susceptibility are not necessarily conserved (see below; see, also, Humeau et al., *Biochimie* 82:427-446 (2000); Niemann et al., *Trends in Cell Biol.* 4:179-185 (1994); and Pellizzari et al., *Phil. Trans. R. Soc. London* 354:259-268 (1999)).

Naturally occurring tetanus and botulinum neurotoxins are produced as polypeptide chains of 150 kDa without a leader sequence. These toxins may be cleaved by bacterial or tissue proteinases at an exposed protease-sensitive loop, generating active di-chain toxin. Naturally occurring clostridial toxins contain a single interchain disulfide bond bridging the heavy chain (H, 100 kDa) and light chain (L, 50 kDa); such a bridge is important for neurotoxicity of toxin added extracellularly (Montecucco and Schiavo, *Quarterly Rev. Biophysics* 28:423-472 (1995)).

Figure 2:
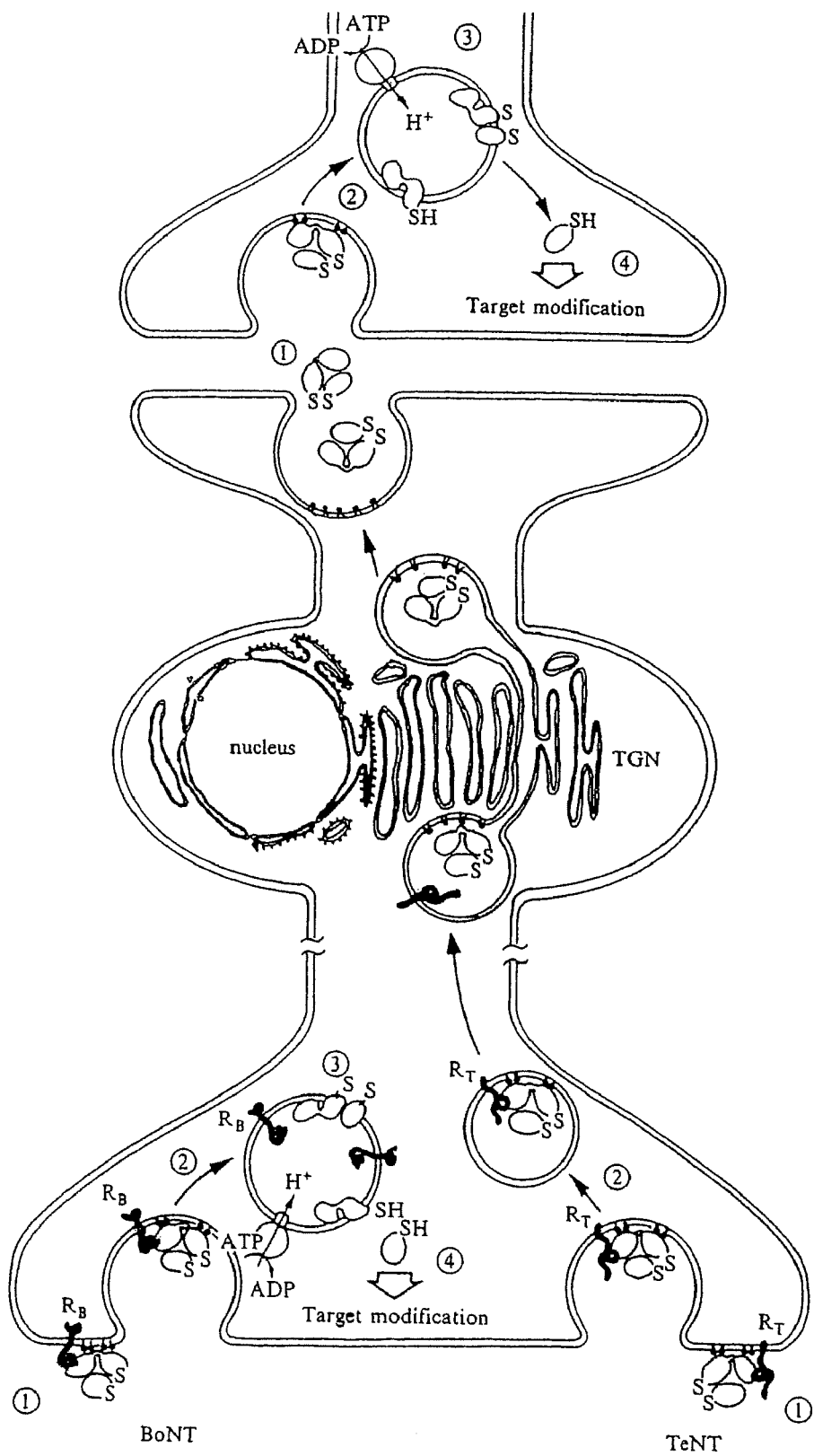
FIG. 2 shows a schematic of the four steps required for tetanus and botulinum toxin activity in central and peripheral neurons.

The clostridial toxins appear to be folded into three distinct 50 kDa domains, as shown in FIG. 1, with each domain having a separate functional role. As illustrated in FIG. 2, the cell intoxication mechanism of the clostridial toxins consists of four distinct steps: (1) binding; (2) internalization; (3) membrane translocation; and (4) enzymatic target modification. The carboxy-terminal part of the heavy chain ($H_C$) functions in neurospecific binding, while the amino-terminal portion of the H chain ($H_N$) functions in membrane translocation. The L chain is responsible for the intracellular catalytic activity (Montecucco and Schiavo, supra, 1995).

The amino acid sequences of eight human clostridial neurotoxins have been derived from the corresponding genes (Neimann, "Molecular Biology of Clostridial Neurotoxins" in *Sourcebook of Bacterial Protein Toxins* Alouf and Freer (Eds.) pp. 303-348 London: Academic Press 1991). The L and H chains are composed of roughly 439 and 843 residues, respectively, and homologous segments are separated by regions of little or no similarity. The most well conserved regions of the L chains are the amino-terminal portion (100 residues) and central region (corresponding to residues 216 to 244 of TeNT), as well as the two cysteines forming the interchain disulfide bond. The 216 to 244 region contains a His-Glu-X-X-His binding motif characteristic of zinc-endopeptidases.

The heavy chain is less well conserved than the light chain, with the carboxy-terminal part of $H_C$ (corresponding to residues 1140 to 1315 of TeNT) being the most variable. This is consistent with the involvement of the $H_C$ domain in binding to nerve terminals and the fact that the different neurotoxins appear to bind different receptors. Not surprisingly, many serotype specific antibodies recognize heavy chain determinants.

Figure 5:
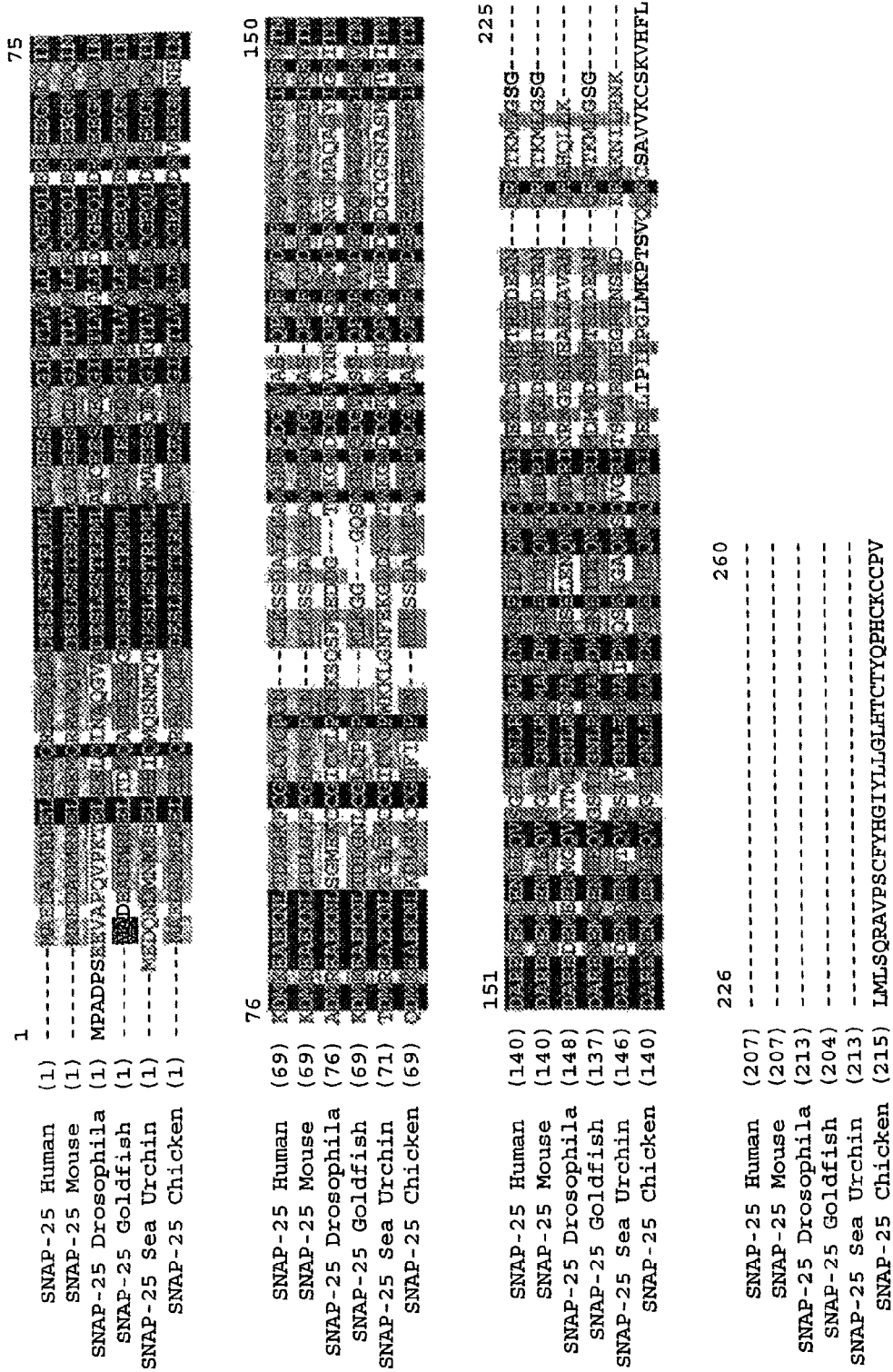
FIG. 5 shows an alignment of various SNAP-25 proteins. Human SNAP-25 (SEQ ID NO: 2; GenBank accession g4507099; see, also, related human SNAP-25 sequence g2135800); mouse SNAP-25 (SEQ ID NO: 12; GenBank accession G6755588); *Drosophila* SNAP-25 (SEQ ID NO: 13; GenBank accession g548941); goldfish SNAP-25 (SEQ ID NO: 14; GenBank accession g2133923); sea urchin SNAP-25 (SEQ ID NO: 15; GenBank accession g2707818) and chicken SNAP-25 (SEQ ID NO: 16; GenBank accession g481202) are depicted.
Figure 7:
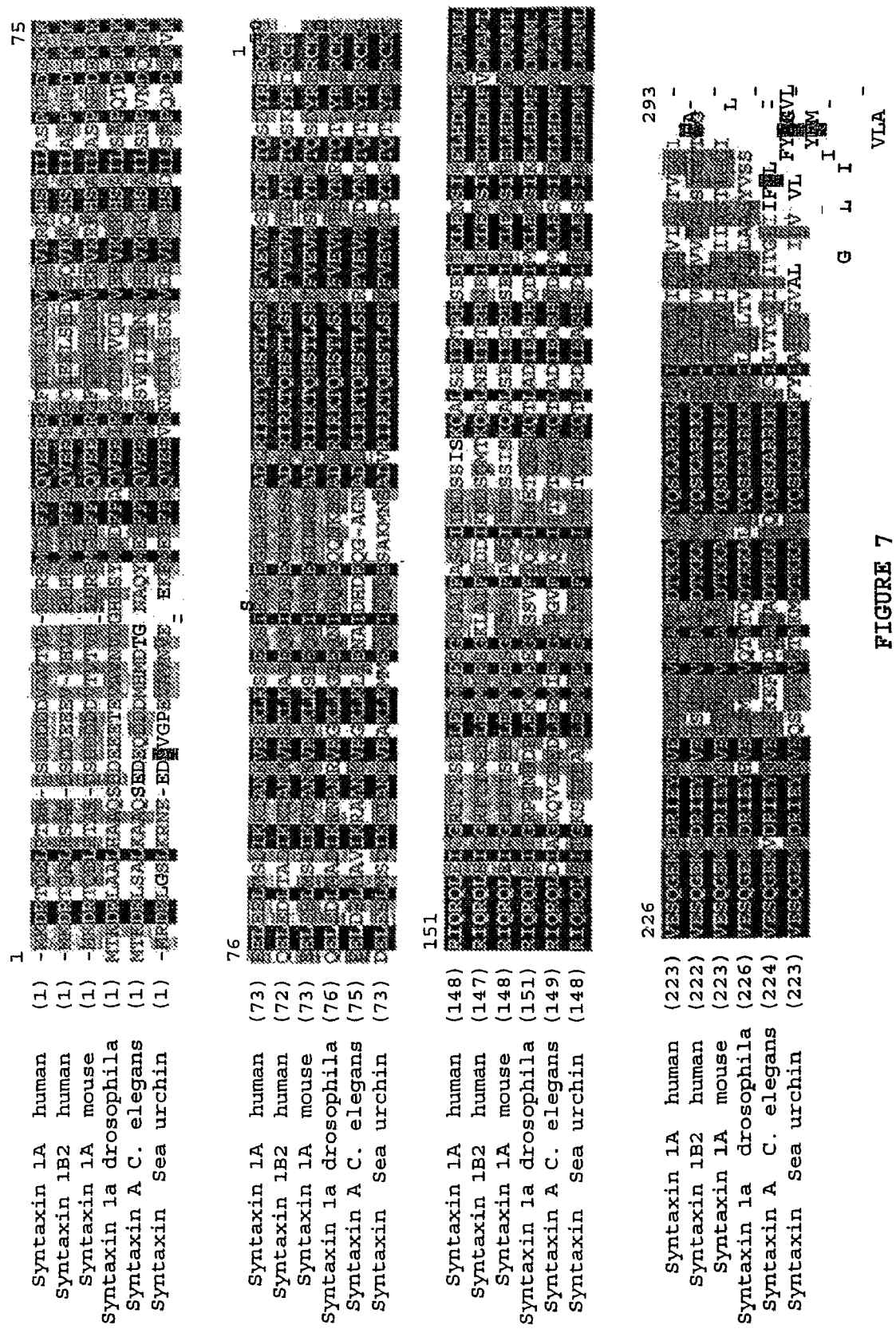
FIG. 7 shows an alignment of various syntaxin proteins. Human syntaxin 1A (SEQ ID NO: 21; GenBank accession g15079184), human syntaxin 1B2 (SEQ ID NO: 22; GenBank accession g15072437), mouse syntaxin 1A (SEQ ID NO: 23; GenBank accession g15011853), *Drosophila* syntaxin 1A (SEQ ID NO: 24; GenBank accession g2501095); *C. elegans* syntaxin A (SEQ ID NO: 25; GenBank accession g7511662) and sea urchin syntaxin (SEQ ID NO: 26; GenBank accession g13310402) are depicted.

Comparison of the nucleotide and amino acid sequences of the clostridial toxins indicates that they derive from a common ancestral gene. Spreading of the clostridial neutrotoxin genes may have been facilitated by the fact that these genes are located on mobile genetic elements. As discussed further below, sequence variants of the clostridial neurotoxins, including the seven botulinum toxins are known in the art. See, for example, FIGS. 5 to 7 and Humeau et al., supra, 2000.

Figure 3:
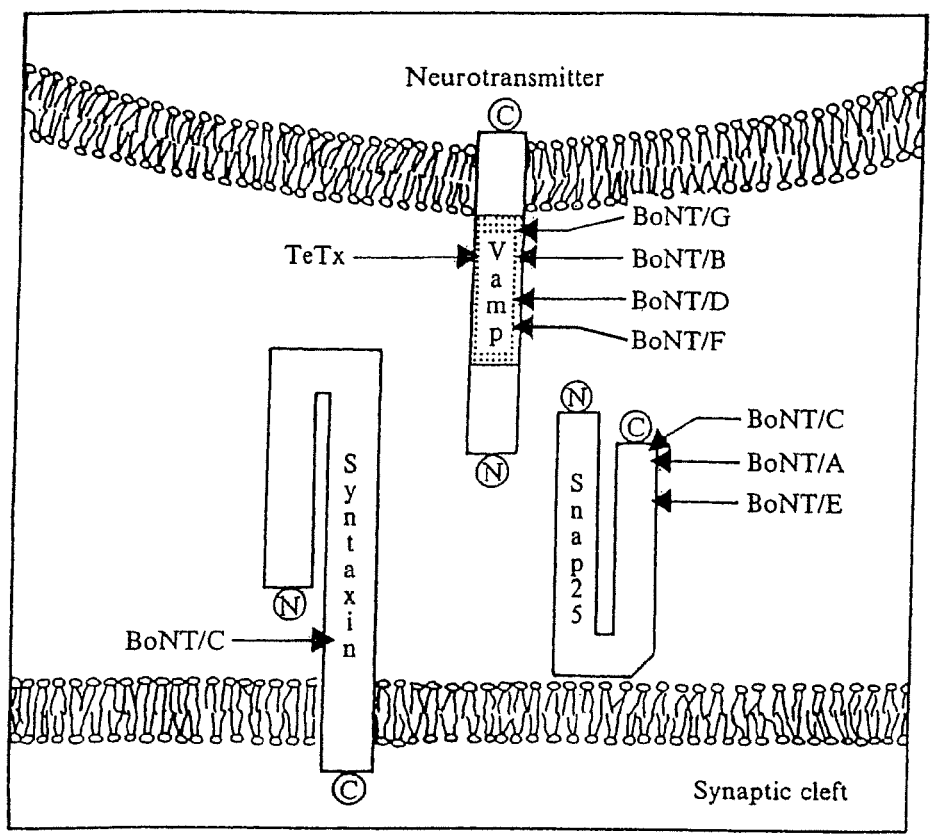
FIG. 3 shows the subcellular localization at the plasma membrane and sites of cleavage of SNAP-25, VAMP and syntaxin. VAMP is bound to synaptic vesicle membrane, whereas SNAP-25 and syntaxin are bound to the target plasma membrane. BoNT/A and /E cleave SNAP-25 close to the carboxy-terminus, releasing nine or 26 residues, respectively. BoNT/B, /D, /F, /G and TeNT act on the conserved central portion of VAMP (dotted) and release the amino-terminal portion of VAMP into the cytosol. BoNT/C1 cleaves SNAP-25 close to the carboxy-terminus as well as cleaving syntaxin at a single site near the cytosolic membrane surface. The action of BoNT/B, /C1, /D, /F, /G and TeNT results in release of a large portion of the cytosolic domain of VAMP or syntaxin, while only a small portion of SNAP-25 is released by selective proteolysis by BoNT/A, /C1 or /E.

As discussed above, natural targets of the clostridial neurotoxins include VAMP, SNAP-25, and syntaxin. As depicted in FIG. 3, VAMP is associated with the synaptic vesicle membrane, whereas SNAP-25 and syntaxin are associated with the target membrane. BoNT/A and BoNT/E cleave SNAP-25 in the carboxy-terminal region, releasing nine or twenty-six amino acid residues, respectively, and BoNT/C1 also cleaves SNAP-25 near the carboxy-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. Thus, the action of BoNT/B, BoNT/C1, BoNT/D, BoNT/F, BoNT/G and TeNT results in release of a large portion of the cytosolic domain of VAMP or syntaxin, while only a small portion of SNAP-25 is released by proteolysis of BoNT/A, BoNT/C1 or BoNT/E (Montecucco and Schiavo, supra, 1995).

SNAP-25, a protein of about 206 residues lacking a transmembrane segment, is associated with the cytosolic surface of the nerve plasmalemma (FIG. 3; see, also, Hodel et al., *Int. J. Biochemistry and Cell Biology* 30:1069-1073 (1998)). In addition to homologs highly conserved from *Drosophila* to mammals, SNAP-25-related proteins also have been cloned from yeast. SNAP-25 is required for axonal growth during development and may be required for nerve terminal plasticity in the mature nervous system. In humans, two isoforms are differentially expressed during development; isoform a is constitutively expressed beginning in the embryo stage, while isoform b appears at birth and predominates in adult life. SNAP-25 analogues such as SNAP-23 also are expressed outside the nervous system, for example, in pancreatic cells.

VAMP is a protein of about 120 residues, with the exact length depending on the species and isotype. As shown in FIG. 3, VAMP contains a short carboxy-terminal segment inside the vesicle lumen while most of the molecule is exposed to the cytosol. The proline-rich amino-terminal thirty residues are divergent among species and isoforms while the central portion of VAMP (residues 30 to 96), which is rich in charged and hydrophilic residues and includes known cleavage sites, is highly conserved. VAMP is associated on the synaptic vesicle membrane with synaptophysin.

A variety of species homologs of VAMP are known in the art including, without limitation, human, rat, bovine, *Torpedo, Drosophila*, yeast, squid and *Aplysia* homologs. In addition, multiple isoforms of VAMP have been identified, including VAMP-1, VAMP-2 and cellubrevin, and insensitive forms have been identified in non-neuronal cells. VAMP appears to be present in all vertebrate tissues although the distribution of VAMP-1 and VAMP-2 varies in different cell types. Chicken and rat VAMP-1 are not cleaved by TeNT or BoNT/B. These VAMP-1 homologs have a valine in place of glutamine present in human and mouse VAMP-1 at the TeNT or BoNT/B cleavage site. The substitution does not affect the activity of BoNT/D, /F or /G, which cleave both VAMP-1 and VAMP-2 with similar rates.

Syntaxin, located on the cytosolic surface of the nerve plasmalemma, is membrane-anchored via a carboxy-terminal segment such that most of the protein is exposed to the cytosol. Syntaxin colocalizes with calcium channels at the active zones of the presynaptic membrane where neurotransmitter release takes place. In addition, syntaxin interacts with synaptotagmin, a protein of the SSV membrane which forms a functional bridge between the plasmalemma and vesicles. A variety of syntaxin isoforms have been identified. Two isoforms of slightly different lengths (285 and 288 residues) have been identified in nerve cells (isoforms 1A and 1B), with isoforms 2, 3, 4 and 5 present in other tissues. The isoforms have varying sensitivities to BoNT/C1, with the 1A, 1B, 2 and 3 syntaxin isoforms cleaved by this toxin.

As indicated above, a SNAP-25 substrate of the invention includes (i) a green fluorescent protein; (ii) a first partner of an affinity couple; and (iii) a portion of SNAP-25 that includes a BoNT/A, BoNT/C1 or BoNT/E recognition sequence containing a cleavage site, where the cleavage site intervenes between the green fluorescent protein and the first partner of the affinity couple. A tagged toxin substrate of the invention includes (i) a fluorescent protein; (ii) a first partner of an affinity couple; and (iii) a clostridial toxin recognition sequence containing a cleavage site, where the cleavage site intervenes between the fluorescent protein and the first partner of the affinity couple.

A SNAP-25 substrate includes, in part, a green fluorescent protein. As used herein, the term "green fluorescent protein" is synonymous with "GFP" and means a protein which absorbs light of a certain wavelength and emits light energy of wavelengths in the range of 520-565 nm. Green fluorescent proteins useful in the invention include, without limitation, wild type green fluorescent proteins such as *A. Victoria* GFP (SEQ ID NO: 98) or homologs thereof, as well as naturally occurring and genetically engineered variants of wild type green fluorescent proteins, and active fragments thereof that retain the ability to emit light in the range of 520-565 nm. As non-limiting examples, the term "green fluorescent protein" includes the Ser65Thr variant of GFP of wild type *A. Victoria* GFP, which demonstrates accelerated fluorophore formation (Heim et al., *Nature* 373:663 (1995)); GFP variants containing a Ser65 to Thr, Ala, Gly, Cys or Leu substitution, which convert the major and minor absorbance peaks of wild type GFP to a single absorbance peak at 489 nm, producing brighter green fluorescent proteins (Heim et al., supra, 1995); GFP variants such as Phe64Leu, which alleviate the temperature sensitivity of wild type GFP (Tsien et al., *Biochem.* 67:509 (1998)); Ala206Lys, Leu221 Lys, and Phe223Arg variants of GFP, which overcome dimerization at high concentrations (Zacharias et al., *Science* 296:913 (2002)); and enhanced GFP (EGFP), which combines codon optimization for expression in mammalian cells with the Ser65Thr and Phe64Leu substitutions, resulting in a bright, stable variant (Cormack et al., *Gene* 173:33 (1996)). In one embodiment, a green fluorescent protein useful in the invention has at least 70% amino acid identity with the wild type *A. Victoria* GFP (SEQ ID NO: 98). In other embodiments, a green fluorescent protein useful in the invention has at least 75%, 80%, 85%, 90% or 95% amino acid identity with the wild type *A. Victoria* GFP (SEQ ID NO: 98). In a further embodiment, a green fluorescent protein useful in the invention has at most ten amino acid substitutions relative to the wild type *A. Victoria* GFP (SEQ ID NO: 98). In still further embodiments, a green fluorescent protein useful in the invention has at most one, two, three, four, five, six, seven, eight or nine amino acid substitutions relative to the wild type *A. Victoria* GFP (SEQ ID NO: 98).

A tagged toxin substrate includes, in part, a fluorescent protein. As used herein, the term "fluorescent protein" means a protein which absorbs light energy of a certain wavelength and emits light energy of a longer wavelength. Fluorescent proteins useful in the invention encompass, without limitation, wild type fluorescent proteins and naturally occurring or genetically engineered variants of fluorescent proteins such as those derived from marine organisms.

Fluorescent proteins useful in tagged toxin substrates include, without limitation, *A. victoria*-derived fluorescent proteins (AFPs) such as wild type *A. victoria* proteins and naturally occurring or genetically engineered variants of *A. victoria* proteins. Such fluorescent proteins include, but are not limited to, green fluorescent proteins (GFPs), cyan fluorescent proteins (CFPs), blue fluorescent proteins (BFPs) and yellow fluorescent proteins (YFPs), where the color of the fluorescence depends on the wavelength of the emitted light; green fluorescent proteins emit light in the range of 520-565 nm; cyan fluorescent proteins emit light in the range of 500-520 nm; blue fluorescent proteins emit light in the range of 450-500 nm; yellow fluorescent proteins emit light in the range of 565-590 nm; and red fluorescent proteins, described further below, emit light in the range of 625-740 nm. Furthermore, fluorescent proteins useful in the invention include, for example, those which have been genetically engineered for improved properties such as, without limitation, altered excitation or emission wavelengths; enhanced brightness, pH resistance, stability or speed of fluorophore formation; photoactivation; or reduced oligomerization or photobleaching. A fluorescent protein useful in the invention also can be engineered for improved protein expression by converting wild type codons to other codons more efficiently utilized in the cells which serve to express the SNAP-25 or tagged toxin substrate which includes the fluorescent protein.

Fluorescent proteins useful in the invention encompass those which emit in a variety of spectra, including violet, blue, cyan, green, yellow, orange and red. As described further below, fluorescent proteins useful in the invention also include, yet are not limited to, blue fluorescent proteins (BFPs) and cyan fluorescent proteins (CFPs) produced by random mutagenesis of GFP and rationally designed yellow fluorescent proteins (YFPs). BFP has a Tyr66His substitution relative to GFP that shifts the absorbance spectrum to a peak of 384 nm with emission at 448 nm (Heim et al., *Proc. Natl. Acad. Sci. U.S.A.* 91:12501 (1994)). CFP, which is brighter and more photostable than BFP, has an absorption/emission spectral range intermediate between BFP and EGFP due to a Tyr66Trp substitution (Heim et al., supra, 1994; Heim and Tsien, *Curr. Biol.* 6:178-182 (1996); and Ellenberg et al., *Biotechniques* 25:838 (1998)); the Thr203Tyr CFP variant known as "CGFP" has excitation and emission wavelengths intermediate between CFP and EGFP. The rationally designed YFP has red-shifted absorbance and emission spectra with respect to green fluorescent proteins (Ormo et al., *Science* 273:1392 (1996); Heim and Tsien, supra, 1996). A variety of YFP variants display improved characteristics including, without limitation, the YFP variants "Citrine" (YFP-Val68Leu/Gln69Met; Griesbeck et al., *J. Biol. Chem.* 276:29188-29194 (2001)) and "Venus" (YFP-Phe46Leu/Phe64Leu/Met153Thr/Val 63Ala/Ser175Gly), an extremely bright and fast-maturing YFP (Nagai et al., *Nature Biotech.* 20:87-90 (2002)). One skilled in the art understands that these and a variety of other fluorescent proteins which are derived, for example, from GFP or other naturally occurring fluorescent proteins also can be useful in the invention. See, for example, Lippincott-Schwartz, *Science* 300:87 (2003), and Zhang et al., *Nature Reviews* 3:906-918 (2002).

A fluorescent protein useful in the invention also can be a long wavelength fluorescent protein such as a red or far-red fluorescent protein, which can be useful for reducing or eliminating background fluorescence from samples derived from eukaryotic cells or tissues. Such red fluorescent proteins include naturally occurring and genetically modified forms of *Discosoma striata* proteins including, without limitation, DsRed (DsRed1 or drFP583; Matz et al., *Nat. Biotech.* 17:969-973 (1999)); dsRed2 (Terskikh et al., *J. Biol. Chem.* 277:7633-7636 (2002)); T1 (dsRed-Express; Clontech; Palo Alto, Calif.; Bevis and Glick, *Nature Biotech.* 20:83-87 (2002)); and the dsRed variant mRFP1 (Campbell et al., *Proc. Natl. Acad. Sci. USA* 99:7877-7882 (2002)). Such red fluorescent proteins further include naturally occurring and genetically modified forms of *Heteractis crispa* proteins such as HcRed (Gurskaya et al., *FEBS Lett.* 507:16 (2001)).

Fluorescent proteins useful in a tagged toxin substrate can be derived from any of a variety of species including marine species such as *A. victoria* and other coelenterate marine organisms. Useful fluorescent proteins encompass, without limitation, *Renilla mulleri*-derived fluorescent proteins such as the dimeric *Renilla mulleri* GFP, which has narrow excitation (498 nm) and emission (509 nm) peaks (Peele et al., *J. Prot. Chem.* 507-519 (2001)); *Anemonia sulcata* fluorescent proteins such as DsRed proteins, for example, asFP595 (Lukyanov et al., *J. Biol. Chem.* 275: 25879-25882 (2000)); *Discosoma* fluorescent proteins, for example, *Discosoma striata* red fluorescent proteins such as dsFP593 (Fradkov et al., *FEBS Lett.* 479:127-130 (2000)); *Heteractis crispa* fluorescent proteins such as HcRed and HcRed-2A (Gurskaya et al., *FEBS Lett.* 507:16-20 (2001)); and *Entacmeae quadricolor* fluorescent proteins including red fluorescent proteins such as eqFP611 (Wiedenmann et al., *Proc. Natl. Acad. Sci. USA* 99:11646-11651 (2002)). One skilled in the art understands that these and many other fluorescent proteins, including species homologs of the above described naturally occurring fluorescent proteins as well as engineered fluorescent proteins can be useful in recombinant tagged toxin substrates encoded by nucleic acid molecules of the invention. Expression vectors suitable for bacterial, mammalian and other expression of fluorescent proteins are available from a variety of commercial sources including BD Biosciences (Palo Alto, Calif.).

As used herein, the term "fluorescent cleavage product" means that portion of a tagged toxin substrate containing the fluorescent protein, where the portion is generated by proteolysis at the clostridial toxin cleavage site. By definition, a "fluorescent cleavage product" does not include the first partner of the affinity couple.

Further provided herein is a tagged toxin substrate which includes a genetically encoded detectable marker. As used herein, the term "genetically encoded detectable marker" means a protein having a property such that the relative quantity of a substrate or cleavage product containing the marker can be readily determined. Such a genetically encoded detectable marker generates a detectable cleavage product when the marker is included in a tagged toxin substrate which is treated with a sample containing clostridial toxin. Any of a variety of genetically encoded detectable markers are useful in the invention including, but not limited to, enzymes; tetracysteine motifs; fluorescent, bioluminescent, chemiluminescent and other luminescent proteins; haptens; and single-chain antibodies.

As used herein, the term "detectable cleavage product" means that portion of a tagged toxin substrate containing a genetically encoded detectable marker, where the portion is generated by proteolysis of the tagged toxin substrate at the clostridial toxin cleavage site.

One skilled in the art understands that the relative quantity of a detectable cleavage product is determined using a system or instrument appropriate to the genetically encoded detectable marker. As examples, a spectrophotometer can be used to assay a chromogenic detectable cleavage product generated from a tagged toxin substrate containing a genetically encoded chromogenic marker; a fluorometer can be used to assay a fluorescent detectable cleavage product generated from a tagged toxin substrate containing a genetically encoded fluorescent marker; and a luminometer can be used to assay a luminescent detectable cleavage product generated from a tagged toxin substrate containing a genetically encoded luminescent marker.

Any of a variety of genetically encoded detectable markers are useful in a tagged toxin substrate. In one embodiment, the genetically encoded detectable marker is an enzyme such as, without limitation, horseradish peroxidase (HRP), alkaline phosphatase (AP), luciferase; β-galactosidase, urease, β-glucouronidase (GUS), glucose oxidase or β-lactamase. As non-limiting examples, the relative quantity of a horseradish-peroxidase containing detectable cleavage product can be determined using a chromogenic substrate such as tetramethylbenzidine (TMB), yielding a soluble product in the presence of hydrogen peroxide which is detectable by measuring absorbance at 450 nm; the relative quantity of a detectable alkaline phosphatase-containing cleavage product can be determined using a chromogenic substrate such as p-nitrophenyl phosphate, which yields a soluble product readily detectable by measuring absorbance at 405 nm; the relative quantity of a detectable luciferase-containing cleavage product can be determined using luciferin as a substrate in the presence of ATP, $Mg^{2+}$ and molecular oxygen (Bronstein et al., *Anal. Biochem.* 219:169-181 (1994)); and the relative quantity of a detectable β-galactosidase containing cleavage product can be determined using a chromogenic substrate such as o-nitrophenyl-β-D-galactopyranoside (ONPG), which yields a soluble product detectable by measuring absorbance at 410 nm, or detectable by chemiluminescence using, for example, a 1,2-dioxetane substrate (Bronstein et al., supra, 1994). Similarly, the relative quantity of a detectable urease-containing cleavage product can be determined using a substrate such as urea-bromocresol purple (Sigma Immunochemicals, St. Louis, Mo.); and the relative quantity of a detectable β-glucouronidase (GUS)-containing cleavage product can be determined with a colorimetric assay using, for example, a β-glucouronide substrate such as X-Gluc; with a fluorescence assay using, for example, 4-methylumbelliferyl-β-D-galactoside (4-MUG; Jefferson et al., supra, 1987); or with a chemiluminescent assay using, for example, an adamantyl 1,2-dioxetane aryl glucuronide substrate (Bronstein et al., supra, 1994). In the same fashion, the relative quantity of a detectable β-lactamase-containing cleavage product can be determined, for example, with a fluorescence assay using, for example, a fluorescent substrate ester (Zlokarnik et al., *Science* 279:84-88 (1998)). See, also, Ausubel, Current Protocols in Molecular Biology John Wiley & Sons, Inc., New York 2000.

A genetically encoded detectable marker useful in a tagged toxin substrate also can be a fluorescent protein such as, without limitation, a naturally occurring or genetically engineered variant of a fluorescent *Aequorea victoria*, *Renilla mulleri*, *Anemonia sulcata*, *Discosoma striata*, *Heteractis crispa*, and *Entacmeae quadricolor* fluorescent protein. A fluorescent protein useful in the invention further can be, without limitation, a green fluorescent protein, blue fluorescent protein, cyan fluorescent protein, yellow fluorescent protein or red fluorescent protein. A variety of fluorescent proteins useful in the invention are described hereinabove and are otherwise known in the art. See, for example, Zhang et al., supra, 2002; Falk, *Trends Cell Biol.* 12:399-404 (2002); Selvin, supra, 2000; and Mahajan et al., supra, 1999.

A genetically encoded detectable marker useful in the invention also can be a tetracysteine motif. Exemplary tetracysteine motifs useful in the invention include, without limitation, the sequence Cys-Cys-Xaa-Xaa-Cys-Cys (SEQ ID NO: 99) or Cys-Cys-Pro-Gly-Cys-Cys (SEQ ID NO: 100). When combined with a biarsenical reagent, a reduced tetracysteine motif forms a fluorescent complex in which each arsenic atom of the conjugate cooperatively binds a pair of cysteines within the motif. Thus, the relative quantity of a tetracysteine motif-containing cleavage fragment can be determined by its ability to form a fluorescent covalent complex when combined with a biarsenical protein such as the resorufin-based red label (ReAsH-$EDT_2$), the fluorescein arsenical helix binder (FlAsH-$EDT_2$) or the biarsenical protein CHoXAsH-$EDT_2$ (Adams et al., *J. Am. Chem. Soc.* 124: 6063-6076 (2002), and Zhang et al., supra, 2002). It is understood that these and other biarsenical proteins are useful for determining the relative quantity of a tetracysteine-motif containing cleavage fragment in a method of the invention.

A genetically encoded detectable marker useful in the invention also can be a hapten or single-chain antibody. A variety of genetically encoded haptens are known in the art, including, yet not limited to, FLAG, hemaglutinin (HA), c-myc, 6-HIS and AU1 haptens, which can be detected in conjunction with commercially available antibodies as disclosed hereinbelow. Using procedures well known in the art, the relative quantity of a hapten-containing detectable cleavage fragment can be determined using a labeled anti-hapten antibody or labeled secondary antibody. As a non-limiting example, an enzyme-linked immunosorbent assay (ELISA) can be useful for determining the relative quantity of a hapten-containing detectable cleavage product. One skilled in the art understands that, where a tagged toxin substrate includes a genetically encoded detectable marker which is a hapten, such a hapten is selected to be distinct from the first and second partners of the affinity couple. One skilled in the art further understands that these and a variety of other well-known genetically encoded detectable markers including, but not limited to, enzymes; tetracysteine motifs; fluorescent, bioluminescent, chemiluminescent and other luminescent proteins; haptens; and single-chain antibodies can be useful in the tagged toxin substrates of the invention.

A SNAP-25 or tagged toxin substrate includes a first partner of an affinity couple. As used herein, the term "affinity couple" means first and second partners which are capable of forming a stable, non-covalent association. An affinity couple useful in the invention can be, without limitation, a histidine tag-metal; binding protein-ligand; biotinylation sequence-streptavidin; streptavidin-biotin; S peptide-S protein; antigen-antibody; or receptor-ligand.

As indicated above, a first partner of an affinity couple is included in a SNAP-25 or tagged toxin substrate. In particular, a SNAP-25 substrate contains a BoNT/A, /C1 or /E cleavage site which intervenes between the green fluorescent protein and the first partner of the affinity couple. Thus, upon proteolysis at the cleavage site, the green fluorescent protein is separated from the portion of the SNAP-25 substrate containing the first partner of the affinity couple. Similarly, a tagged toxin substrate contains a clostridial toxin cleavage site which intervenes between the fluorescent protein or other genetically encoded detectable marker and the first partner of the affinity couple. Thus, upon proteolysis at the cleavage site of a tagged toxin substrate, the fluorescent protein or genetically encoded detectable marker is separated from the portion of the tagged toxin substrate that contains the first partner of the affinity couple. As described further below, the methods of the invention can be practiced by contacting a treated sample with the second partner of the affinity couple in order to separate the fluorescent or otherwise detectable cleavage product (which lacks the first partner of the affinity couple) from uncleaved substrate and other components of the treated sample which contain the first partner of the affinity couple.

A SNAP-25 or tagged toxin substrate includes a clostridial toxin recognition sequence. As used herein, the term "clostridial toxin recognition sequence" means a scissile bond together with adjacent or non-adjacent recognition elements, or both, sufficient for detectable proteolysis at the scissile bond by a clostridial toxin under conditions suitable for clostridial toxin protease activity.

In a SNAP-25 or tagged toxin substrate, a cleavage site "intervenes" between a green fluorescent protein or other fluorescent protein or genetically encoded detectable marker and the first partner of the affinity couple. Thus, the cleavage site is positioned in between the green fluorescent protein, or other fluorescent protein or genetically encoded detectable marker, and the first partner of the affinity couple, such that proteolysis at the cleavage site results in a fluorescent or otherwise detectable cleavage product, which lacks the first partner of the affinity couple, and the remaining portion of the substrate, which includes the first partner of the affinity couple. It is understood that all or only a part of the clostridial toxin recognition sequence can intervene between the green fluorescent protein or other fluorescent protein or genetically encoded detectable marker and the first partner of the affinity couple.

A SNAP-25 or tagged toxin substrate contains a clostridial toxin cleavage site which is positioned between a green fluorescent protein, or other fluorescent protein or genetically encoded detectable marker, and a first partner of an affinity couple. In one embodiment, the green fluorescent protein, or other fluorescent protein or genetically encoded detectable marker, is positioned amino-terminal of the cleavage site while the first partner of the affinity couple is positioned carboxy-terminal of the cleavage site. In another embodiment, the green fluorescent protein, or other fluorescent protein or genetically encoded detectable marker, is positioned carboxy-terminal of the cleavage site while the first partner of the affinity couple is positioned amino-terminal of the cleavage site.

Clostridial toxins have specific and distinct cleavage sites. BoNT/A cleaves a Gln-Arg bond; BoNT/B and TeNT cleave a Gln-Phe bond; BoNT/C1 cleaves a Lys-Ala or Arg-Ala bond; BoNT/D cleaves a Lys-Leu bond; BoNT/E cleaves an Arg-Ile bond; BoNT/F cleaves a Gln-Lys bond; and BoNT/G cleaves an Ala-Ala bond (see Table 1). In standard nomenclature, the sequence surrounding a clostridial toxin cleavage site is denoted $P_5$-$P_4$-$P_3$-$P_2$-$P_1$-$P_1'$-$P_2'$-$P_3'$-$P_4'$-$P_5'$, with $P_1$-$P_1'$ representing the scissile bond. It is understood that a $P_1$ or $P_1'$ site, or both, can be substituted with another amino acid or amino acid mimetic in place of the naturally occurring residue. For example, BoNT/A substrates have been prepared in which the $P_1$ position (Gln) is modified to be an alanine, 2-aminobutyric acid or asparagine residue, and these substrates were hydrolyzed by BoNT/A at the $P_1$-Arg bond (Schmidt and Bostian, *J. Protein Chem.* 16:19-26 (1997)). While substitutions can be introduced at the $P_1$ position of the scissile bond, for example, a BoNT/A scissile bond, it is further recognized that conservation of the $P_1'$ residue is more often important for detectable proteolysis (Vaidyanathan et al., *J. Neurochem.* 72:327-337 (1999)). Thus, in particular embodiments, the invention provides a SNAP-25 or tagged toxin substrate in which the $P_1'$ residue is not modified or substituted relative to the naturally occurring residue in a target protein cleaved by the clostridial toxin. In further embodiments, the invention provides a SNAP-25 or tagged toxin substrate in which the $P_1$ residue is modified or substituted relative to the naturally occurring residue in a target protein cleaved by the clostridial toxin; such a substrate retains susceptibility to peptide bond cleavage between the $P_1$ and $P_1'$ residues.

SNAP-25, VAMP and syntaxin share a short motif located within regions predicted to adopt an α-helical conformation (see FIG. 4). This motif is present in SNAP-25, VAMP and syntaxin isoforms expressed in animals sensitive to the neurotoxins. In contrast, *Drosophila* and yeast homologs that are resistant to these neurotoxins and syntaxin isoforms not involved in exocytosis contain sequence variations in the α-helical motif regions of these VAMP and syntaxin proteins.

TABLE 1

| Bond cleaved in human VAMP-2, SNAP-25 or syntaxin | | | |
|---|---|---|---|
| Toxin | Target | $P_4$-$P_3$-$P_2$-$P_1$--$P_1'$-$P_2'$-$P_3'$-$P_4'$ | SEQ ID NO: |
| BoNT/A | SNAP-25 | Glu-Ala-Asn-Gln—Arg*-Ala-Thr-Lys | SEQ ID NO: 1 |
| BoNT/B | VAMP-2 | Gly-Ala-Ser-Gln—Phe*-Glu-Thr-Ser | SEQ ID NO: 3 |

TABLE 1-continued Bond cleaved in human VAMP-2, SNAP-25 or syntaxin

| Toxin | Target | $P_4$-$P_3$-$P_2$-$P_1$--$P_1'$-$P_2'$-$P_3'$-$P_4'$ | SEQ ID NO: |
|---|---|---|---|
| BoNT/C1 | syntaxin | Asp-Thr-Lys-Lys—Ala\*-Val-Lys-Tyr | SEQ ID NO: 5 |
| BoNT/D | VAMP-2 | Arg-Asp-Gln-Lys—Leu\*-Ser-Glu-Leu | SEQ ID NO: 6 |
| BoNT/E | SNAP-25 | Gln-Ile-Asp-Arg—Ile\*-Met-Glu-Lys | SEQ ID NO: 8 |
| BoNT/F | VAMP-2 | Glu-Arg-Asp-Gln—Lys\*-Leu-Ser-Glu | SEQ ID NO: 9 |
| BoNT/G | VAMP-2 | Glu-Thr-Ser-Ala—Ala\*-Lys-Leu-Lys | SEQ ID NO: 10 |
| TeNT | VAMP-2 | Gly-Ala-Ser-Gln—Phe\*-Glu-Thr-Ser | SEQ ID NO: 11 |

*Scissile bond shown in bold

Figure 4:
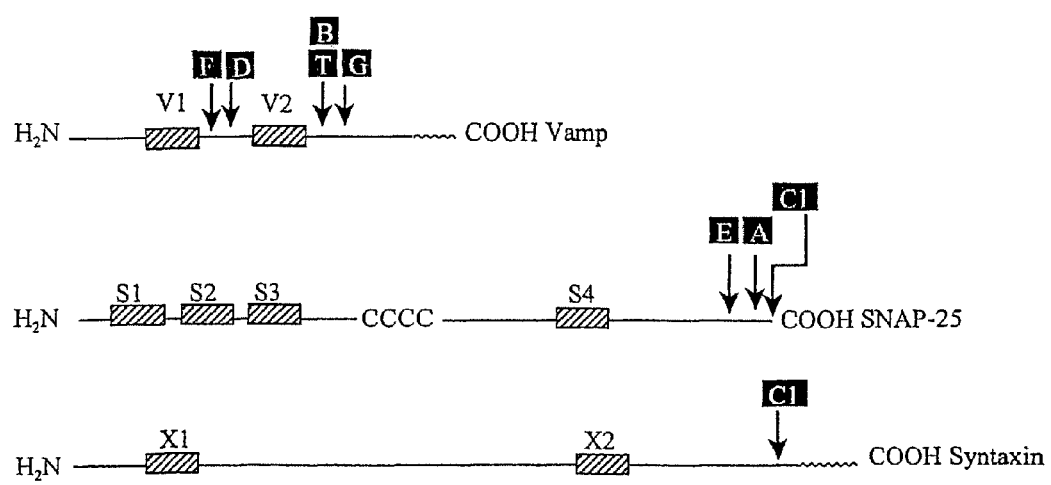
FIG. 4 shows the neurotoxin recognition motif of VAMP, SNAP-25 and syntaxin. (A) Hatched boxes indicate the presence and positions of a motif common to the three targets of clostridial neurotoxins. (B) The recognition motif is composed of hydrophobic residues ("h"); negatively charged Asp or Glu residues ("–") and polar residues ("p"); "x" represents any amino acid. The motif is included in regions of VAMP, SNAP-25 and syntaxin predicted to adopt an α-helical conformation. (C) A top view of the motif in an α-helical conformation is shown. Negatively charged residues align on one face, while hydrophobic residues align on a second face.
Figure 4:
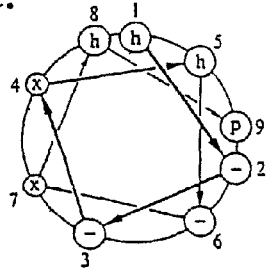

Multiple repetitions of the α-helical motif are present in proteins sensitive to cleavage by clostridial toxins: four copies are naturally present in SNAP-25; two copies are naturally present in VAMP; and two copies are naturally present in syntaxin (see FIG. 4A). Furthermore, peptides corresponding to the specific sequence of the α-helical motifs can inhibit neurotoxin activity in vitro and in vivo, and such peptides can cross-inhibit different neurotoxins. In addition, antibodies raised against such peptides can cross-react among the three target proteins, indicating that the α-helical motif is exposed on the protein surface and adopts a similar configuration in each of the three target proteins. Consistent with these findings, SNAP-25-specific, VAMP-specific and syntaxin-specific neurotoxins cross-inhibit each other by competing for the same binding site, although they do not cleave targets non-specifically. These results indicate that a clostridial toxin recognition sequence can include, if desired, at least one α-helical motif. However, it is recognized that an α-helical motif is not absolutely required for cleavage by a clostridial toxin as evidenced by 16-mer and 17-mer peptides which serve as substrates for BoNT/A although they lack an α-helical motif.

In one embodiment, the invention provides a SNAP-25 or tagged toxin substrate in which the clostridial toxin recognition sequence includes a single α-helical motif. In another embodiment, the invention provides a SNAP-25 or tagged toxin substrate in which the clostridial toxin recognition sequence includes two or more α-helical motifs. As non-limiting examples, a BoNT/A or BoNT/E recognition sequence can include a S4 α-helical motif, alone or combined with one or more additional α-helical motifs; a BoNT/B, BoNT/G or TeNT recognition sequence can include the V2 α-helical motif, alone or combined with one or more additional α-helical motifs; a BoNT/C1 recognition sequence can include the S4 α-helical motif, alone or combined with one or more additional α-helical motifs, or an X2 α-helical motif, alone or combined with one or more additional α-helical motifs; and a BoNT/D or BoNT/F recognition sequence can include the V1 α-helical motif, alone or combined with one or more additional α-helical motifs (see FIG. 4A).

As used herein, the term "botulinum toxin serotype A recognition sequence" is synonymous with "BoNT/A recognition sequence" and means a scissile bond together with adjacent or non-adjacent recognition elements, or both, sufficient for detectable proteolysis at the scissile bond by a BoNT/A under conditions suitable for clostridial toxin protease activity. A scissile bond cleaved by BoNT/A can be, for example, Gln-Ala.

A variety of BoNT/A recognition sequences are well known in the art. A BoNT/A recognition sequence can have, for example, residues 134 to 206 or residues 137 to 206 of human SNAP-25 (Ekong et al., supra, 1997; U.S. Pat. No. 5,962,637). A BoNT/A recognition sequence also can include, without limitation, the sequence Thr-Arg-Ile-Asp-Glu-Ala-Asn-Gln-Arg-Ala-Thr-Lys-Met (SEQ ID NO: 27), or a peptidomimetic thereof, which corresponds to residues 190 to 202 of human SNAP-25; Ser-Asn-Lys-Thr-Arg-Ile-Asp-Glu-Ala-Asn-Gln-Arg-Ala-Thr-Lys (SEQ ID NO: 28), or a peptidomimetic thereof, which corresponds to residues 187 to 201 of human SNAP-25; Ser-Asn-Lys-Thr-Arg-Ile-Asp-Glu-Ala-Asn-Gln-Arg-Ala-Thr-Lys-Met (SEQ ID NO: 29), or a peptidomimetic thereof, which corresponds to residues 187 to 202 of human SNAP-25; Ser-Asn-Lys-Thr-Arg-Ile-Asp-Glu-Ala-Asn-Gln-Arg-Ala-Thr-Lys-Met-Leu (SEQ ID NO: 30), or a peptidomimetic thereof, which corresponds to residues 187 to 203 of human SNAP-25; Asp-Ser-Asn-Lys-Thr-Arg-Ile-Asp-Glu-Ala-Asn-Gln-Arg-Ala-Thr-Lys-Met (SEQ ID NO: 31), or a peptidomimetic thereof, which corresponds to residues 186 to 202 of human SNAP-25; or Asp-Ser-Asn-Lys-Thr-Arg-Ile-Asp-Glu-Ala-Asn-Gln-Arg-Ala-Thr-Lys-Met-Leu (SEQ ID NO: 32), or a peptidomimetic thereof, which corresponds to residues 186 to 203 of human SNAP-25. See, for example, Schmidt and Bostian, *J. Protein Chem.* 14:703-708 (1995); Schmidt and Bostian, supra, 1997; Schmidt et al., *FEBS Letters* 435:61-64 (1998); and Schmidt and Bostian, U.S. Pat. No. 5,965,699). If desired, a similar BoNT/A recognition sequence can be prepared from a corresponding (homologous) segment of another BoNT/A-sensitive SNAP-25 isoform or homolog such as, for example, murine, rat, goldfish or zebrafish SNAP-25 or can be any of the peptides disclosed herein or described in the art, for example, in U.S. Pat. No. 5,965,699.

A BoNT/A recognition sequence can correspond to a segment of a protein that is sensitive to cleavage by botulinum toxin serotype A, or can be substantially similar to a segment of a BoNT/A-sensitive protein. As illustrated in Table 2, a variety of naturally occurring proteins sensitive to cleavage by BoNT/A are known in the art and include, for example, human, mouse and rat SNAP-25; and goldfish SNAP-25A and SNAP-25B. Thus, a BoNT/A recognition sequence useful in a SNAP-25 or tagged toxin substrate of the invention can correspond, for example, to a segment of human SNAP-25, mouse SNAP-25, rat SNAP-25, goldfish SNAP-25A or 25B, or another naturally occurring protein sensitive to cleavage by BoNT/A. Furthermore, comparison of native SNAP-25 amino acid sequences cleaved by BoNT/A reveals that such sequences are not absolutely conserved (see Table 2 and FIG. 5), indicating that a variety of amino acid substitutions and modifications relative to a naturally occurring BoNT/A- sensitive SNAP-25 sequence can be tolerated in a SNAP-25 or tagged toxin substrate of the invention Gln197, Ala199, Thr200 and Met202, Leu203, Gly204, Ser205, and Gly206, as well as residues more distal from the

TABLE 2

Cleavage of SNAP-25 and related proteins[a,b,c,d]

| Species | Isoform | Cleavage Sites BoNT/E ⇓ | BoNT/A ⇓⇓ BoNT/C | SEQ ID NO: | Resistance to Cleavage by |
|---|---|---|---|---|---|
| human mouse rat | SNAP-25 | 174 qnrqid ri mekadsnktridean | 206 qra tkmlgsg | 33 | none[a] |
| human | SNAP-23 | 180 qnpqik ri tdkadtnrdridian | ara end kklids | 34 | all[b] |
| mouse | SNAP-23 | 179 qnqqiq ki tekadtnknridian | end tra kklids | 35 | BoNT/A & C |
| chicken | SNAP-25 | 174 qnrqid ri meklipikpglmkpt | end svq qrcsavvk | 36 | BoNT/A & C |
| goldfish | SNAP-25A | 171 qnrqid ri mdmadsnktridean | end qra tkmlgsg | 37 | none |
| goldfish | SNAP-25B | 172 qnrqid ri mekadsnktridean | end qra tkmlgsg | 38 | none |
| Torpedo | SNAP-25 | 180 qnaqvd ri vvkgdmnkaridean | end kha tkml | 39 | BoNT/E[c] & A[d] |
| sea urchin | SNAP-25 | 180 qnsqvg ri tskaesnegrinsad | end kra knilrnk | 40 | (?)[e] |
| C-elegans | SNAP-25 | 203 qnrqld ri hdkqsnevrvesank | end rak nlitk | 41 | BoNT/A & C |
| Drosophila | SNAP-25 | 182 qnrqid ri nrkgesneariavan | end qra hqllk | 42 | BoNT/E & A[e] |
| leech | SNAP-25 | 181 qnrqvd ri nnkmtsnqlrisdan | end kra skllke | 43 | BoNT/A[e] |

[a]= In vitro cleavage of SNAP-25 requires 1000-fold higher BoNT/C concentration than BoNT/A or /E.
[b]= Substitution of p182r, or k185dd (boxes) induces susceptibility toward BoNT/E.
[c]= Resistance to BoNT/A possibly due to d189 or e189 substitution by v189, see box.
[d]= Note that Torpedo is susceptible to BoNT/A.
[e]= Note the presence of several non-conservative mutations around putative cleavage sites.

A SNAP-25 or tagged toxin substrate which includes a BoNT/A recognition sequence can have one or multiple modifications as compared to a naturally occurring sequence that is cleaved by BoNT/A. For example, as compared to a 17-mer corresponding to residues 187 to 203 of human SNAP-25, substitution of Asp193 with Asn resulted in a relative rate of proteolysis of 0.23; substitution of Glu194 with Gln resulted in a relative rate of 2.08; substitution of Ala195 with 2-aminobutyric acid resulted in a relative rate of 0.38; and substitution of Gln197 with Asn, 2-aminobutyric acid or Ala resulted in a relative rate of 0.66, 0.25, or 0.19, respectively (see Table 3). Furthermore, substitution of Ala199 with 2-aminobutyric acid resulted in a relative rate of 0.79; substitution of Thr200 with Ser or 2-aminobutyric acid resulted in a relative rate of 0.26 or 1.20, respectively; substitution of Lys201 with Ala resulted in a relative rate of 0.12; and substitution of Met202 with Ala or norleucine resulted in a relative rate of 0.38 or 1.20, respectively. See Schmidt and Bostian, supra, 1997. These results indicate that a variety of residues can be substituted in a SNAP-25 or tagged toxin substrate as compared to a naturally occurring toxin-sensitive sequence. In the case of BoNT/A, these results indicate that residues including but not limited to Glu194, Ala195, Gln-Arg scissile bond can be substituted to produce a SNAP-25 or tagged toxin substrate of the invention. Such a substrate is detectably proteolyzed at the scissile bond by BoNT/A under conditions suitable for clostridial toxin protease activity. In sum, it is understood that a SNAP-25 or tagged toxin substrate can include, if desired, one or several amino acid substitutions, additions or deletions relative to a naturally occurring SNAP-25 sequence. A SNAP-25 or tagged toxin substrate also can optionally include a carboxy-terminal amide.

TABLE 3

Kinetic parameters of BoNT/A synthetic peptide substrates

| Peptide | Sequence[a] | SEQ ID NO: | Relative Rate[b] |
|---|---|---|---|
| [1-15] | SNKTRIDEANQRATK | 28 | 0.03 |
| [1-16] | SNKTRIDEANQRATKM | 29 | 1.17 |
| [1-17] | SNKTRIDEANQRATKML | 30 | 1.00 |

TABLE 3-continued

Kinetic parameters of BoNT/A synthetic peptide substrates

| Peptide | Sequence[a] | SEQ ID NO: | Relative Rate[b] |
|---|---|---|---|
| M16A | SNKTRIDEANQRATKAL | 44 | 0.38 |
| M16X | SNKTRIDEANQRATKXL | 45 | 1.20 |
| K15A | SNKTRIDEANQRATAML | 46 | 0.12 |
| T14S | SNKTRIDEANQRASKML | 47 | 0.26 |
| T14B | SNKTRIDEANQRABKML | 48 | 1.20 |
| A13B | SNKTRIDEANQRBTKML | 49 | 0.79 |
| Q11A | SNKTRIDEANARATKML | 50 | 0.19 |
| Q11B | SNKTRIDEANBRATKML | 51 | 0.25 |
| Q11N | SNKTRIDEANNRATKML | 52 | 0.66 |
| N10A | SNKTRIDEAAQRATKML | 53 | 0.06 |
| A9B | SNKTRIDEBNQRATKML | 54 | 0.38 |
| E8Q | SNKTRIDQANQRATKML | 55 | 2.08 |
| D7N | SNKTRINEANQRATKML | 56 | 0.23 |

[a]Nonstandard amino acid abbreviations are:
B, 2-aminobutyric acid;
X, 2-aminohexanoic acid (norleucine)
[b]Initial hydrolysis rates relative to peptide [1-17]. Peptide concentrations were 1.0 mM.

TABLE 4

Cleavage of VAMP[a,b]

| Species | Isoform | Cleavage Sites BoNT/F ⇓⇓ | BoNT/D | TeNT ⇓ | BoNT/G ⇓ | SEQ ID NO: | Resistance to Cleavage by |
|---|---|---|---|---|---|---|---|
| human mouse bovine | VAMP-1 | 53 dkvlerd | qkl selddradalqagas | qf ess | aa klkrkyww 92 | 57 | none |
| human mouse bovine | VAMP-2 | 51 dkvlerd | qkl selddradalqagas | qf ets | aa klkrkyww 90 | 58 | none |
| rat | VAMP-2 | 53 dkvlerd | qkl selddradalqagas | vf ess | aa klkrkyww 92 | 59 | TeNT & BoNT/B |
| rat | VAMP-2 | 51 dkvlerd | qkl selddradalqagas | qf ets | aa klkrkyww 90 | 60 | none |
| rat | Cellubrevin | 38 dkvlerd | qkl selddradalqagas | qf ets | aa klkrkyww 77 | 61 | none |
| rat | TI-VAMP | 146 dlvaqrg | erl ellidktenlvdssv | tf ktt | sr nlaramcm 175 | 62 | all |
| chicken | VAMP-1 | - ----erd | qkl selddradalqagas | vf ess | aa klkr---- - | 63 | TeNT & BoNT/B |
| chicken | VAMP-2 | - ----erd | qkl selddradalqagas | qf ets | aa klkr---- - | 64 | none |
| Torpedo | VAMP-1 | 55 dkvlerd | qkl selddradalqagas | qf ess | aa klkrkyww 94 | 65 | none |
| sea urchin | VAMP | 35 dkvldrd | qal svlddradaiqqgas | gf etn | ag klkrkyww 74 | 66 | BoNT/F, D & G |
| *Aplysia* | VAMP | 41 ekvldrd | qki sqlddraealqagas | gf eas | ag klkrkyww 80 | 67 | BoNT/G |
| squid | VAMP | 60 dkvlerd | ski selddradalqagas | gf eas | ag klkrkfww 99 | 68 | BoNT/F & G |
| *C. elegans* | VAMP | 86 nkvmerd | vgl nsldhraevlqngas | qf qqs | sr elkrqyww 115 | 69 | BoNT/F, D & G |
| | | 67 | | | 106 | | TeNT & |

TABLE 4-continued

Cleavage of VAMP[a,b]

| Species | Isoform | Cleavage Sites BoNT/F ⇓⇓ BoNT/D | TeNT ⇓ | BoNT/G ⇓ | SEQ ID NO: | Resistance to Cleavage by |
|---|---|---|---|---|---|---|
| Drosphila | syb[a] | ekvlerd qkl selgeradqleqgas | gs eqq | ag klkrkqww | 70 | BoNT/B & G |
| Drosphila | n-syb[b] | 61<br>ekvlerd skl selddradalqqgas | gf eqq | 100<br>ag klkrkfwl | 71 | BoNT/F & G |
| leech | VAMP | 49<br>dkvlekd qkl aeldgradalqagas | qf eas | 88<br>ag klkrkfww | 72 | BoNT/G |

[a] = Sequence corrected in position 93 (f > s).
[b] = Sequence corrected in position 68 (t > s).

TABLE 5

Cleavage of syntaxin

| Species | Isoform | Cleavage Sites BoNT/c ⇓ | | SEQ ID NO: | Resistance to Cleavage by |
|---|---|---|---|---|---|
| human rat mouse bovine | syntaxin 1A | 245<br>eravsdtk ka | 262<br>vkyqskar | 73 | no |
| human rat mouse bovine | syntaxin 1B | 244<br>eravsdtk ka | 261<br>vkyqskar | 74 | no |
| rat | syntaxin 2 | 245<br>ehakeetk ka | 262<br>ikyqskar | 75 | no |
| rat | syntaxin 3 | 244<br>ekardetr ka | 261<br>mkyqgqar | 76 | no |
| rat | syntaxin 4 | 244<br>ergqehvk ia | 261<br>lenqkkar | 77 | yes |
| chicken | syntaxin 1B | 239<br>vpevfvtk sa | 259<br>vmyqcksr | 78 | expected |
| sea urchin | syntaxin | 243<br>vrrqndtk ka | 269<br>vkyqskar | 79 | no |
| Aplysia | syntaxin 1 | 247<br>etakmdtk ka | 264<br>vkyqskar | 80 | no |
| squid | syntaxin | 248<br>etakvdtk ka | 265<br>vkyqskar | 81 | no |
| Drosophila | Dsynt 1 | 248<br>qtatqdtk ka | 265<br>lkyqskar | 82 | no |
| leech | syntaxin 1 | 251<br>etaaadtk ka | 268<br>mkyqsaar | 83 | no |

As used herein, the term "botulinum toxin serotype B recognition sequence" is synonymous with "BoNT/B recognition sequence" and means a scissile bond together with adjacent or non-adjacent recognition elements, or both, sufficient for detectable proteolysis at the scissile bond by a BoNT/B under appropriate conditions. A scissile bond cleaved by BoNT/B can be, for example, Gln-Phe.

A variety of BoNT/B recognition sequences are well known in the art or can be defined by routine methods. Such a BoNT/B recognition sequence can include, for example, a sequence corresponding to some or all of the hydrophilic core of a VAMP protein such as human VAMP-1 or human VAMP-2. A BoNT/B recognition sequence can include, without limitation, residues 33 to 94, residues 45 to 94, residues 55 to 94, residues 60 to 94, residues 65 to 94, residues 60 to 88 or residues 65 to 88 of human VAMP-2 (SEQ ID NO: 4), or residues 60 to 94 of human VAMP-1 (SEQ ID NO: 96) (see, for example, Shone et al., *Eur. J. Biochem.* 217: 965-971 (1993) and U.S. Pat. No. 5,962,637). If desired, a similar BoNT/B recognition sequence can be prepared from a corresponding (homologous) segment of another BoNT/B-sensitive VAMP isoform or homolog such as human VAMP-1 or rat or chicken VAMP-2.

Thus, it is understood that a BoNT/B recognition sequence can correspond to a segment of a protein that is sensitive to cleavage by botulinum toxin serotype B, or can be substantially similar to such a segment of a BoNT/B-sensitive protein. As shown in Table 4, a variety of naturally occurring proteins sensitive to cleavage by BoNT/B are known in the art and include, for example, human, mouse and bovine VAMP-1 and VAMP-2; rat VAMP-2; rat cellubrevin; chicken VAMP-2; Torpedo VAMP-1; sea urchin VAMP; Aplysia VAMP; squid VAMP; C. elegans VAMP; Drosophila n-syb; and leech VAMP. Thus, a BoNT/B recognition sequence useful in a tagged toxin substrate of the invention can correspond, for example, to a segment of human VAMP-1 or VAMP-2, mouse VAMP-1 or VAMP-2, bovine VAMP-1 or VAMP-2, rat VAMP-2, rat cellubrevin, chicken VAMP-2, Torpedo VAMP-1, sea urchin VAMP, Aplysia VAMP, squid VAMP, C. elegans VAMP, Drosophila n-syb, leech VAMP, or another naturally occurring protein sensitive to cleavage by BoNT/B. Furthermore, as shown in Table 4, comparison of native VAMP amino acid sequences cleaved by BoNT/B reveals that such sequences are not absolutely conserved (see, also, FIG. 6), indicating that a variety of amino acid substitutions and modifications relative to a naturally occurring VAMP sequence can be tolerated in a tagged toxin substrate which includes a BoNT/A recognition sequence.

As used herein, the term "botulinum toxin serotype C1 recognition sequence" is synonymous with "BoNT/C1 recognition sequence" and means a scissile bond together with adjacent or non-adjacent recognition elements, or both, sufficient for detectable proteolysis at the scissile bond by a BoNT/C1 under appropriate conditions. A scissile bond cleaved by BoNT/C1 can be, for example, Lys-Ala or Arg-Ala.

It is understood that a BoNT/C1 recognition sequence can correspond to a segment of a protein that is sensitive to cleavage by botulinum toxin serotype C1, or can be substantially similar to a segment of a BoNT/C1-sensitive protein. As shown in Table 5, a variety of naturally occurring proteins sensitive to cleavage by BoNT/C1 are known in the art and include, for example, human, rat, mouse and bovine syntaxin 1A and 1B; rat syntaxins 2 and 3; sea urchin syntaxin; Aplysia syntaxin 1; squid syntaxin; Drosophila Dsynt1; and leech syntaxin 1 Thus, a BoNT/C1 recognition sequence useful in a tagged toxin substrate of the invention can correspond, for example, to a segment of human, rat, mouse or bovine syntaxin 1A or 1B, rat syntaxin 2, rat syntaxin 3, sea urchin syntaxin, Aplysia syntaxin 1, squid syntaxin, Drosophila Dsynt1, leech syntaxin 1, or another naturally occurring protein sensitive to cleavage by BoNT/C1. Furthermore, comparison of native syntaxin amino acid sequences cleaved by BoNT/C1 reveals that such sequences are not absolutely conserved (see Table 5 and FIG. 7), indicating that a variety of amino acid substitutions and modifications relative to a naturally occurring BoNT/C1-sensitive syntaxin sequence can be tolerated in a tagged toxin substrate including a BoNT/C1 recognition sequence.

A variety of naturally occurring SNAP-25 proteins also are sensitive to cleavage by BoNT/C1, including human, mouse and rat SNAP-25; goldfish SNAP-25A and 25B; and Drosophila and leech SNAP-25. Thus, a BoNT/C1 recognition sequence useful in a SNAP-25 or tagged toxin substrate of the invention can correspond, for example, to a segment of human, mouse or rat SNAP-25, goldfish SNAP-25A or 25B, Torpedo SNAP-25, zebrafish SNAP-25, Drosophila SNAP-25, leech SNAP-25, or another naturally occurring protein sensitive to cleavage by BoNT/C1. As discussed above in regard to variants of naturally occurring syntaxin sequences, comparison of native SNAP-25 amino acid sequences cleaved by BoNT/C1 reveals significant sequence variability (see Table 2 and FIG. 5 above), indicating that a variety of amino acid substitutions and modifications relative to a naturally occurring BoNT/C1-sensitive SNAP-25 sequence can be tolerated in a SNAP-25 or tagged toxin substrate of the invention.

The term "botulinum toxin serotype D recognition sequence" is synonymous with "BoNT/D recognition sequence" and means a scissile bond together with adjacent or non-adjacent recognition elements, or both, sufficient for detectable proteolysis at the scissile bond by a BoNT/D under appropriate conditions. A scissile bond cleaved by BoNT/D can be, for example, Lys-Leu.

A variety of BoNT/D recognition sequences are well known in the art or can be defined by routine methods. A BoNT/D recognition sequence can include, for example, residues 27 to 116; residues 37 to 116; residues 1 to 86; residues 1 to 76; or residues 1 to 69 of rat VAMP-2 (SEQ ID NO: 7; Yamasaki et al., J. Biol. Chem. 269:12764-12772 (1994)). Thus, a BoNT/D recognition sequence can include, for example, residues 27 to 69 or residues 37 to 69 of rat VAMP-2 (SEQ ID NO: 7). If desired, a similar BoNT/D recognition sequence can be prepared from a corresponding (homologous) segment of another BoNT/D-sensitive VAMP isoform or homolog such as human VAMP-1 or human VAMP-2.

A BoNT/D recognition sequence can correspond to a segment of a protein that is sensitive to cleavage by botulinum toxin serotype D, or can be substantially similar to a segment of a BoNT/D-sensitive protein. As shown in Table 5, a variety of naturally occurring proteins sensitive to cleavage by BoNT/D are known in the art and include, for example, human, mouse and bovine VAMP-1 and VAMP-2; rat VAMP-1 and VAMP-2; rat cellubrevin; chicken VAMP-1 and VAMP-2; Torpedo VAMP-1; Aplysia VAMP; squid VAMP; Drosophila syb and n-syb; and leech VAMP. Thus, a BoNT/D recognition sequence useful in a tagged toxin substrate of the invention can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, Torpedo VAMP-1, Aplysia VAMP, squid VAMP, Drosophila syb or n-syb, leech VAMP, or another naturally occurring protein sensitive to cleavage by BoNT/D. Furthermore, as shown in Table 5 above, comparison of native VAMP amino acid sequences cleaved by BoNT/D reveals significant sequence variability (see, also, FIG. 6), indicating that a variety of amino acid substitutions and modifications relative to a naturally occurring BoNT/D-sensitive VAMP sequence can be tolerated in a tagged toxin substrate of the invention.

As used herein, the term "botulinum toxin serotype E recognition sequence" is synonymous with "BoNT/E recognition sequence" and means a scissile bond together with adjacent or non-adjacent recognition elements, or both, sufficient for detectable proteolysis at the scissile bond by a BoNT/E under appropriate conditions. A scissile bond cleaved by BoNT/E can be, for example, Arg-Ile.

One skilled in the art appreciates that a BoNT/E recognition sequence can correspond to a segment of a protein that is sensitive to cleavage by botulinum toxin serotype E, or can be substantially similar to a segment of a BoNT/E-sensitive protein. A variety of naturally occurring proteins sensitive to cleavage by BoNT/E are known in the art and include, for example, human, mouse and rat SNAP-25; mouse SNAP-23;

chicken SNAP-25; goldfish SNAP-25A and SNAP-25B; zebrafish SNAP-25; *C. elegans* SNAP-25; and leech SNAP-25 (see Table 2). Thus, a BoNT/E recognition sequence useful in a SNAP-25 or tagged toxin substrate of the invention can correspond, for example, to a segment of human SNAP-25, mouse SNAP-25, rat SNAP-25, mouse SNAP-23, chicken SNAP-25, goldfish SNAP-25A or 25B, *C. elegans* SNAP-25, leech SNAP-25, or another naturally occurring protein sensitive to cleavage by BoNT/E. Furthermore, as shown in Table 2 and FIG. 5 above, comparison of native SNAP-23 and SNAP-25 amino acid sequences cleaved by BoNT/E reveals that such sequences are not absolutely conserved, indicating that a variety of amino acid substitutions and modifications relative to a naturally occurring BoNT/E-sensitive SNAP-23 or SNAP-25 sequence can be tolerated in a SNAP-25 or tagged toxin substrate of the invention.

The term "botulinum toxin serotype F recognition sequence," as used herein, is synonymous with "BoNT/F recognition sequence" and means a scissile bond together with adjacent or non-adjacent recognition elements, or both, sufficient for detectable proteolysis at the scissile bond by a BoNT/F under appropriate conditions. A scissile bond cleaved by BoNT/F can be, for example, Gln-Lys.

A variety of BoNT/F recognition sequences are well known in the art or can be defined by routine methods. A BoNT/F recognition sequence can include, for example, residues 27 to 116; residues 37 to 116; residues 1 to 86; residues 1 to 76; or residues 1 to 69 of rat VAMP-2 ((SEQ ID NO: 7; Yamasaki et al., supra, 1994). A BoNT/F recognition sequence also can include, for example, residues 27 to 69 or residues 37 to 69 of rat VAMP-2 (SEQ ID NO: 7). It is understood that a similar BoNT/F recognition sequence can be prepared, if desired, from a corresponding (homologous) segment of another BoNT/F-sensitive VAMP isoform or homolog such as human VAMP-1 or human VAMP-2.

A BoNT/F recognition sequence can correspond to a segment of a protein that is sensitive to cleavage by botulinum toxin serotype F, or can be substantially similar to a segment of a BoNT/F-sensitive protein. A variety of naturally occurring proteins sensitive to cleavage by BoNT/F are known in the art and include, for example, human, mouse and bovine VAMP-1 and VAMP-2; rat VAMP-1 and VAMP-2; rat cellubrevin; chicken VAMP-1 and VAMP-2; Torpedo VAMP-1; *Aplysia* VAMP; *Drosophila* syb; and leech VAMP (see Table 5). Thus, a BoNT/F recognition sequence useful in a tagged toxin substrate of the invention can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, Torpedo VAMP-1, *Aplysia* VAMP, *Drosophila* syb, leech VAMP, or another naturally occurring protein sensitive to cleavage by BoNT/F. Furthermore, as shown in Table 5 above, comparison of native VAMP amino acid sequences cleaved by BoNT/F reveals that such sequences are not absolutely conserved (see, also, FIG. 6), indicating that a variety of amino acid substitutions and modifications relative to a naturally occurring BoNT/F-sensitive VAMP sequence can be tolerated in a tagged toxin substrate which includes a BoNT/F recognition sequence.

As used herein, the term "botulinum toxin serotype G recognition sequence" is synonymous with "BoNT/G recognition sequence" and means a scissile bond together with adjacent or non-adjacent recognition elements, or both, sufficient for detectable proteolysis at the scissile bond by a BoNT/G under appropriate conditions. A scissile bond cleaved by BoNT/G can be, for example, Ala-Ala.

A BoNT/G recognition sequence can correspond to a segment of a protein that is sensitive to cleavage by botulinum toxin serotype G, or can be substantially similar to such a BoNT/G-sensitive segment. As illustrated in Table 5 above, a variety of naturally occurring proteins sensitive to cleavage by BoNT/G are known in the art and include, for example, human, mouse and bovine VAMP-1 and VAMP-2; rat VAMP-1 and VAMP-2; rat cellubrevin; chicken VAMP-1 and VAMP-2; and Torpedo VAMP-1. Thus, a BoNT/G recognition sequence useful in a tagged toxin substrate of the invention can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, Torpedo VAMP-1, or another naturally occurring protein sensitive to cleavage by BoNT/G. Furthermore, as shown in Table 5 above, comparison of native VAMP amino acid sequences cleaved by BoNT/G reveals that such sequences are not absolutely conserved (see, also, FIG. 6), indicating that a variety of amino acid substitutions and modifications relative to a naturally occurring BoNT/G-sensitive VAMP sequence can be tolerated in a tagged toxin substrate which includes a BoNT/G recognition sequence.

The term "tetanus toxin recognition sequence" means a scissile bond together with adjacent or non-adjacent recognition elements, or both, sufficient for detectable proteolysis at the scissile bond by a tetanus toxin under appropriate conditions. A scissile bond cleaved by TeNT can be, for example, Gln-Phe.

A variety of TeNT recognition sequences are well known in the art or can be defined by routine methods and include a sequence corresponding to some or all of the hydrophilic core of a VAMP protein such as human VAMP-1 or human VAMP-2. A TeNT recognition sequence can include, for example, residues 25 to 93 or residues 33 to 94 of human VAMP-2 (SEQ ID NO: 4; Cornille et al., *Eur. J. Biochem.* 222:173-181 (1994); Foran et al., *Biochem.* 33: 15365-15374 (1994)); residues 51 to 93 or residues 1 to 86 of rat VAMP-2 (SEQ ID NO: 7; Yamasaki et al., supra, 1994); or residues 33 to 94 of human VAMP-1 (SEQ ID NO: 96). A TeNT recognition sequence also can include, for example, residues 25 to 86, residues 33 to 86 or residues 51 to 86 of human VAMP-2 (SEQ ID NO: 4) or rat VAMP-2 (SEQ ID NO: 7). It is understood that a similar TeNT recognition sequence can be prepared, if desired, from a corresponding (homologous) segment of another TeNT-sensitive VAMP isoform or species homolog such as human VAMP-1 or sea urchin or *Aplysia* VAMP.

Thus, a TeNT recognition sequence can correspond to a segment of a protein that is sensitive to cleavage by tetanus toxin, or can be substantially similar to a segment of a TeNT-sensitive protein. As shown in Table 5 above, a variety of naturally occurring proteins sensitive to cleavage by TeNT are known in the art and include, for example, human, mouse and bovine VAMP-1 and VAMP-2; rat VAMP-2; rat cellubrevin; chicken VAMP-2; Torpedo VAMP-1; sea urchin VAMP; *Aplysia* VAMP; squid VAMP; *C. elegans* VAMP; *Drosophila* n-syb; and leech VAMP. Thus, a TeNT recognition sequence useful in a tagged toxin substrate of the invention can correspond, for example, to a segment of human VAMP-1 or VAMP-2, mouse VAMP-1 or VAMP-2, bovine VAMP-1 or VAMP-2, rat VAMP-2, rat cellubrevin, chicken VAMP-2, Torpedo VAMP-1, sea urchin VAMP, *Aplysia* VAMP, squid VAMP, *C. elegans* VAMP, *Drosophila* n-syb, leech VAMP, or another naturally occurring protein sensitive to cleavage by TeNT. Furthermore, comparison of native VAMP amino acid sequences cleaved by TeNT reveals that such sequences are not absolutely conserved (Table 5 and FIG. 6), indicating that a variety of amino acid substitutions and modifications relative to a naturally occurring TeNT-sensitive VAMP sequence can be tolerated in a tagged toxin substrate which includes a TeNT recognition sequence.

In view of the above, it is clear that a "portion of SNAP-25" included in a SNAP-25 substrate, or a "clostridial toxin recognition sequence" included in a tagged toxin substrate, can correspond to a segment of SNAP-25, VAMP or syntaxin which is less than full-length SNAP-25, VAMP or syntaxin. In particular embodiments, a BoNT/A recognition sequence is homologous to at most 160, 140, 120, 100, 80, 60, 40, 20 or 10 consecutive residues of SNAP-25, where the consecutive residues include the cleavage site Gln-Arg. As non-limiting examples, a BoNT/A recognition sequence can have at least 80% amino acid identity with at most 160, 140, 120, 100, 80, 60, 40, 20 or 10 consecutive residues of human SNAP-25 (SEQ ID NO: 2) or another SNAP-25, where the consecutive residues include the cleavage site Gln-Arg.

In other embodiments, a BoNT/B recognition sequence is homologous to at most 160, 140, 120, 100, 80, 60, 40, 20 or 10 consecutive residues of VAMP, where the consecutive residues include the cleavage site Gln-Phe. As non-limiting examples, a BoNT/B recognition sequence can have at least 80% amino acid identity with at most 160, 140, 120, 100, 80, 60, 40, 20 or 10 consecutive residues of human VAMP-1 (SEQ ID NO: 96) or human VAMP-2 (SEQ ID NO: 4) or another VAMP, where the consecutive residues include the cleavage site Gln-Phe.

In further embodiments, a BoNT/C1 recognition sequence is homologous to at most 160, 140, 120, 100, 80, 60, 40, 20 or 10 consecutive residues of syntaxin, where the consecutive residues include the cleavage site Lys-Ala. As non-limiting examples, a BoNT/C1 recognition sequence can have at least 80% amino acid identity with at most 160, 140, 120, 100, 80, 60, 40, 20 or 10 consecutive residues of human syntaxin 1A (SEQ ID NO: 21) or human syntaxin-1B or another syntaxin, where the consecutive residues include the cleavage site Lys-Ala.

In still further embodiments, a BoNT/C1 recognition sequence is homologous to at most 160, 140, 120, 100, 80, 60, 40, 20 or 10 consecutive residues of SNAP-25, where the consecutive residues include the cleavage site Arg-Ala. As non-limiting examples, a BoNT/C1 recognition sequence can have at least 80% amino acid identity with at most 160, 140, 120, 100, 80, 60, 40, 20 or 10 consecutive residues of human SNAP-25 (SEQ ID NO: 2) or another SNAP-25, where the consecutive residues include the cleavage site Arg-Ala.

In additional embodiments, a BoNT/D recognition sequence is homologous to at most 160, 140, 120, 100, 80, 60, 40, 20 or 10 consecutive residues of VAMP, where the consecutive residues include the cleavage site Lys-Leu. As non-limiting examples, a BoNT/D recognition sequence can have at least 80% amino acid identity with at most 160, 140, 120, 100, 80, 60, 40, 20 or 10 consecutive residues of human VAMP-1 (SEQ ID NO: 96) or human VAMP-2 (SEQ ID NO: 4) or another VAMP, where the consecutive residues include the cleavage site Lys-Leu.

In other embodiments, a BoNT/E recognition sequence is homologous to at most 160, 140, 120, 100, 80, 60, 40, 20 or 10 consecutive residues of SNAP-25, where the consecutive residues include the cleavage site Arg-Ile. As non-limiting examples, a BoNT/E recognition sequence can have at least 80% amino acid identity with at most 160, 140, 120, 100, 80, 60, 40, 20 or 10 consecutive residues of human SNAP-25 (SEQ ID NO: 2) or another SNAP-25, where the consecutive residues include the cleavage site Arg-Ile.

In further embodiments, a BoNT/F recognition sequence is homologous to at most 160, 140, 120, 100, 80, 60, 40, 20 or 10 consecutive residues of VAMP, where the consecutive residues include the cleavage site Gln-Lys. As non-limiting examples, a BoNT/F recognition sequence can have at least 80% amino acid identity with at most 160, 140, 120, 100, 80, 60, 40, 20 or 10 consecutive residues of human VAMP-1 (SEQ ID NO: 96) or human VAMP-2 (SEQ ID NO: 4) or another VAMP, where the consecutive residues include the cleavage site Gln-Lys.

In yet further embodiments, a BoNT/G recognition sequence is homologous to at most 160, 140, 120, 100, 80, 60, 40, 20 or 10 consecutive residues of VAMP, where the consecutive residues include the cleavage site Ala-Ala. As non-limiting examples, a BoNT/G recognition sequence can have at least 80% amino acid identity with at most 160, 140, 120, 100, 80, 60, 40, 20 or 10 consecutive residues of human VAMP-1 (SEQ ID NO: 96) or human VAMP-2 (SEQ ID NO: 4) or another VAMP, where the consecutive residues include the cleavage site Ala-Ala.

In still further embodiments, a TeNT recognition sequence is homologous to at most 160, 140, 120, 100, 80, 60, 40, 20 or 10 consecutive residues of VAMP, where the consecutive residues include the cleavage site Gln-Phe. As non-limiting examples, a TeNT recognition sequence can have at least 80% amino acid identity with at most 160, 140, 120, 100, 80, 60, 40, 20 or 10 consecutive residues of human VAMP-1 (SEQ ID NO: 96) or human VAMP-2 (SEQ ID NO: 4) or another VAMP, where the consecutive residues include the cleavage site Gln-Phe.

In another embodiment, a clostridial toxin recognition sequence is a sequence other than a substrate sequence described in U.S. Pat. No. 6,762,280. In further embodiments, a clostridial toxin recognition sequence is a sequence other than SNRTRIDEANQRATRMLG (SEQ ID NO: 109); LSELDDRADALQAGASQFETSAAKLKRKY WWKNLK (SEQ ID NO: 110); AQVDEVVDIMRVNVD-KVLERDQKLSELDDRADALQAGAS (SEQ ID NO: 111); NKLKSSDAYKKAWGNNQDGVVASQPAR-WDEREQMAISGGFIRRVT NDARENEM DENLEQVS-GIIGNLRHMALDMGNEIDTQNRQID-RIMEKADSNKTRIDEANQR ATKMLGSG (SEQ ID NO: 112); or NKLKSSDAYKKAWGNNQDGVVASQPAR-WDEREQM AISGGFIRRVTNDARENEMDENLEQVS-GIIGNLRHMALDMGNEIDTQNRQIDRIMEKADSNK TRIDEANQAATKMLGSG (SEQ ID NO: 113).

A SNAP-25 or tagged toxin substrate also can contain one or multiple clostridial toxin cleavage sites for the same or different clostridial toxin. In one embodiment, a SNAP-25 or tagged toxin substrate contains a single cleavage site. In another embodiment, a SNAP-25 or tagged toxin substrate has multiple cleavage sites for the same clostridial toxin. These cleavage sites can be incorporated within the same or different clostridial toxin recognition sequences. In a further embodiment, a SNAP-25 or tagged toxin substrate has multiple cleavage sites for the same clostridial toxin that intervene between the same green fluorescent protein, or other fluorescent protein or genetically encoded detectable marker, and the first partner of the affinity couple. A SNAP-25 or tagged toxin substrate can contain, for example, two or more, three or more, five or more, seven or more, eight or more, or ten or more cleavage sites for the same clostridial toxin intervening between the same or different green fluorescent protein, or other fluorescent protein or genetically encoded detectable marker, and the first partner of the affinity couple. A SNAP-25 or tagged toxin substrate also can have, for example, two, three, four, five, six, seven, eight, nine or ten cleavage sites for the same clostridial toxin intervening between the same or different green fluorescent protein, or other fluorescent protein or genetically encoded detectable marker, and the first partner of the affinity couple.

A SNAP-25 or tagged toxin substrate also can contain multiple cleavage sites for different clostridial toxins. In one embodiment, a SNAP-25 or tagged toxin substrate includes multiple cleavage sites for different clostridial toxins all intervening between the same green fluorescent protein, or other fluorescent protein or genetically encoded detectable marker, and first partner of the affinity couple. A SNAP-25 or tagged toxin substrate can contain, for example, two or more, three or more, five or more, or ten or more cleavage sites for different clostridial toxins all intervening between the same green fluorescent protein, or other fluorescent protein or genetically encoded detectable marker, and first partner of the affinity couple. A SNAP-25 or tagged toxin substrate also can contain, for example, two or more, three or more, five or more, or ten or more cleavage sites for different clostridial toxins intervening between at least two different pairs of green fluorescent proteins, or other fluorescent proteins or genetically encoded detectable markers, and first partners of an affinity couple. In particular embodiments, a clostridial substrate also has two, three, four, five, six, seven, eight, nine or ten cleavage sites for different clostridial toxins, where the cleavage sites intervene between the same or different pairs of green fluorescent proteins, or other fluorescent proteins or genetically encoded detectable markers, and first partners of an affinity couple. It is understood that a SNAP-25 or tagged toxin substrate having multiple cleavage sites can have any combination of two, three, four, five, six, seven or eight cleavage sites for any combination of the following clostridial toxins: BoNT/A, BoNT/B, BoNT/C1, BoNT/D, BoNT/E, BoNT/F, BoNT/G and TeNT.

It is understood that, in addition to a green fluorescent protein, or other fluorescent protein or genetically encoded detectable marker, a first partner of an affinity couple, and a clostridial toxin recognition sequence, a SNAP-25 substrate or tagged toxin substrate can include, if desired, one or more additional components. As an example, a flexible spacer sequence such as GGGGS (SEQ ID NO: 84) can be included in a SNAP-25 or tagged toxin substrate of the invention. A SNAP-25 or tagged toxin substrate further can include, without limitation, one or more of the following: a carboxy-terminal cysteine residue; an immunoglobulin hinge region; an N-hydroxysuccinimide linker; a peptide or peptidomimetic hairpin turn; a hydrophilic sequence, or another component or sequence that promotes the solubility or stability of the SNAP-25 or tagged toxin substrate.

Furthermore, a SNAP-25 or tagged toxin substrate can be cleaved at a reduced or enhanced rate relative to SNAP-25, VAMP or syntaxin proteins or relative to a similar peptide or peptidomimetic that does not contain a fluorescent protein or genetically encoded detectable marker or a first partner of an affinity couple. A SNAP-25 or tagged toxin substrate such as a BoNT/A, BoNT/B, BoNT/C1, BoNT/D, BoNT/E, BoNT/F, BoNT/G or TeNT substrate can be cleaved, for example, with an initial hydrolysis rate that is at least 5% of the initial hydrolysis rate, under otherwise identical conditions, of human SNAP-25, VAMP or syntaxin, where the SNAP-25 or tagged toxin substrate and SNAP-25, VAMP or syntaxin each is present at a concentration of 16 µM.

Where a SNAP-25 or tagged toxin substrate includes a BoNT/A, BoNT/C1 or BoNT/E recognition sequence, the substrate can be cleaved, for example, with an initial hydrolysis rate that is at least 5%, 10%, 20%, 30%, 40%, 50%, 60%, 70%, 80%, 90%, 100%, 150%, 200%, 250%, or 300% of the initial hydrolysis rate, under otherwise identical conditions, of human SNAP-25 by BoNT/A, BoNT/C1 or BoNT/E, respectively, where the substrate and human SNAP-25 each is present at a concentration of 16 µM. In other embodiments, such a substrate is cleaved with an initial hydrolysis rate that is at least 5%, 10%, 20%, 30%, 40%, 50%, 60%, 70%, 80%, 90%, 100%, 150%, 200%, 250%, or 300% of the initial hydrolysis rate, under otherwise identical conditions, of human SNAP-25 by BoNT/A, BoNT/C1 or BoNT/E, respectively, where the SNAP-25 or tagged toxin substrate and human SNAP-25 each is present at a concentration of 200 µM.

Similarly, where a SNAP-25 or tagged toxin substrate includes a BoNT/B, BoNT/D, BoNT/F or BoNT/G recognition sequence, the substrate can be cleaved, for example, with an initial hydrolysis rate that is at least 5%, 10%, 20%, 30%, 40%, 50%, 60%, 70%, 80%, 90%, 100%, 150%, 200%, 250%, or 300% of the initial hydrolysis rate, under otherwise identical conditions, of human VAMP-2 by BoNT/B, BoNT/D, BoNT/F or BoNT/G, respectively, where substrate of the invention and human VAMP-2 each is present at a concentration of 16 µM. In other embodiments, such a substrate is cleaved with an initial hydrolysis rate that is at least 5%, 10%, 20%, 30%, 40%, 50%, 60%, 70%, 80%, 90%, 100%, 150%, 200%, 250%, or 300% of the initial hydrolysis rate, under otherwise identical conditions, of human VAMP-2 by BoNT/B, BoNT/D, BoNT/F or BoNT/G, respectively, where the SNAP-25 or tagged toxin substrate and human VAMP-2 each is present at a concentration of 200 µM.

Where a tagged toxin substrate includes a BoNT/C1 recognition sequence, the substrate can be cleaved with an initial hydrolysis rate that is at least 5%, 10%, 20%, 30%, 40%, 50%, 60%, 70%, 80%, 90%, 100%, 150%, 200%, 250%, or 300% of the initial hydrolysis rate, under otherwise identical conditions, of human syntaxin by BoNT/C1, where the tagged toxin substrate and human syntaxin each is present at a concentration of 16 µM. In other embodiments, such a substrate is cleaved with an initial hydrolysis rate that is at least 5%, 10%, 20%, 30%, 40%, 50%, 60%, 70%, 80%, 90%, 100%, 150%, 200%, 250%, or 300% of the initial hydrolysis rate, under otherwise identical conditions, of human syntaxin by BoNT/C1, where the tagged toxin substrate and human syntaxin each is present at a concentration of 200 µM.

The "turnover number," or $k_{cat}$, is the rate of breakdown of a toxin-substrate complex. A SNAP-25 or tagged toxin substrate can be cleaved with a $k_{cat}$ that is reduced or enhanced as compared to the $k_{cat}$ of human SNAP-25, human VAMP-2 or human syntaxin target proteins when cleaved by the same clostridial toxin under the same conditions. A SNAP-25 or tagged toxin substrate can be cleaved, for example, with a $k_{cat}$ of about 0.001 to about 4000 $sec^{-1}$. In one embodiment, a SNAP-25 or tagged toxin substrate is cleaved with a $k_{cat}$ of about 1 to about 4000 $sec^{-1}$. In other embodiments, a SNAP-25 or tagged toxin substrate has a $k_{cat}$ of less than 5 $sec^{-1}$, 10 $sec^{-1}$, 25 $sec^{-1}$, 50 $sec^{-1}$, 100 $sec^{-1}$, 250 $sec^{-1}$, 500 $sec^{-1}$, or 1000 $sec^{-1}$. A SNAP-25 or tagged toxin substrate also can have, for example, a $k_{cat}$ in the range of 1 to 1000 $sec^{-1}$; 1 to 500 $sec^{-1}$; 1 to 250 $sec^{-1}$; 1 to 100 $sec^{-1}$; 1 to 50 $sec^{-1}$; 10 to 1000 $sec^{-1}$; 10 to 500 $sec^{-1}$; 10 to 250 $sec^{-1}$; 10 to 100 $sec^{-1}$; 10 to 50 $sec^{-1}$; 25 to 1000 $sec^{-1}$; 25 to 500 $sec^{-1}$; 25 to 250 $sec^{-1}$; 25 to 100 $sec^{-1}$; 25 to 50 $sec^{-1}$; 50 to 1000 $sec^{-1}$; 50 to 500 $sec^{-1}$; 50 to 250 $sec^{-1}$; 50 to 100 $sec^{-1}$; 100 to 1000 $sec^{-1}$; 100 to 500 $sec^{-1}$; or 100 to 250 $sec^{-1}$. One skilled in the art understands the turnover number, $k_{cat}$, is assayed under standard steady state conditions in which there is an excess of substrate.

One skilled in the art understands that there are several considerations in selecting and positioning a green fluorescent protein, or other fluorescent protein or genetically encoded detectable marker and a first partner of an affinity couple in a SNAP-25 or tagged toxin substrate. These elements generally are positioned to minimize interference with substrate binding to, or proteolysis by, the clostridial toxin. Thus, a green fluorescent protein, or other fluorescent protein or genetically encoded detectable marker, and a first partner of an affinity couple can be selected and positioned, for example, so as to minimize the disruption of bonded and non-bonded interactions that are important for binding, and to minimize steric hindrance.

In a complex of a VAMP substrate and the light chain of BoNT/B (LC/B), nearly all VAMP residues with side chains containing hydrogen bond acceptors or donors were hydrogen bonded with the LC/B. Thus, it is understood that a SNAP-25 or tagged toxin substrate of the invention can be prepared, if desired, in which the potential for hydrogen bonding, for example, by Ser, Thr, Tyr, Asp, Glu, Asn or Gln residues is not diminished in the substrate as compared to the potential for hydrogen bonding in a native protein sensitive to cleavage by the toxin. Thus, in particular embodiments, the present invention provides a SNAP-25 or tagged toxin substrate in which the potential for hydrogen-bonding is not diminished in the substrate as compared to a native protein sensitive to cleavage by the corresponding botulinum or tetanus toxin.

The present invention also provides a kit for determining clostridial toxin protease activity. The kit contains a SNAP-25 or tagged toxin substrate in a vial or other container. The kit generally also includes instructions for use. In one embodiment, a kit of the invention further includes as a positive control a known amount of the botulinum or tetanus toxin, such as, without limitation, a recombinant toxin light chain, capable of cleaving the SNAP-25 or tagged toxin substrate included in the kit. In another embodiment, the kit contains a SNAP-25 or tagged toxin substrate and further includes the fluorescent or otherwise detectable cleavage products as a positive control. A kit of the invention may optionally include a container with buffer suitable for clostridial toxin protease activity. As described above, the methods of the invention can be practiced with a combination of tagged toxin substrates. Thus, in one embodiment, the invention provides a kit for determining clostridial toxin protease activity that includes at least two different tagged toxin substrates.

Further provided herein are methods of determining clostridial toxin protease activity by (a) treating with a sample, in solution phase under conditions suitable for clostridial toxin protease activity, a tagged toxin substrate containing (i) a fluorescent protein; (ii) a first partner of an affinity couple; and (iii) a clostridial toxin recognition sequence that includes a cleavage site which intervenes between the fluorescent protein and the first partner of the affinity couple, such that a fluorescent cleavage product is generated when clostridial toxin is present in the sample; (b) contacting the treated sample with a second partner of the affinity couple, thereby forming stable complexes containing the first and second partners of the affinity couple; and (c) assaying the presence or amount of fluorescent cleavage product in the treated sample, thereby determining clostridial toxin protease activity. In one embodiment, a method of the invention is practiced by separating the fluorescent cleavage product from the stable complexes prior to assaying the presence or amount of fluorescent cleavage product. A variety of fluorescent proteins can be useful in the methods of the invention including, without limitation, green fluorescent proteins, blue fluorescent proteins, cyan fluorescent proteins, yellow fluorescent proteins and red fluorescent proteins. In one embodiment, a method of the invention is practiced using a tagged toxin substrate containing a green fluorescent protein. First partners of an affinity couple useful in the methods of the invention encompass, but are not limited to, a histidine tag, glutathione-S-transferase, maltose-binding protein, biotinylation sequence, streptavidin, S peptide, S protein, or an epitope such as a FLAG, hemagluttinin, c-myc or AU1 epitope.

The methods of the invention can be useful for determining clostridial toxin protease activity in any of a variety of samples. Such samples include, but are not limited to, clarified and other crude cell lysates; native and recombinant isolated clostridial toxins; isolated clostridial toxin light chains; formulated clostridial toxin products such as BOTOX® (botulinum toxin serotype A); and foodstuffs, including raw, cooked, partially cooked and processed foods and beverages.

In the methods of the invention, the tagged toxin substrate is treated with a sample in solution phase. As used herein in reference to a tagged toxin substrate, the term "in solution phase" means that the substrate is soluble and is not constrained or immobilized on a solid support such as a bead, column or dish.

As used herein, the term "sample" means any biological matter that contains or potentially contains an active clostridial toxin, or light chain or proteolytically active fragment thereof. Thus, the term sample encompasses, but is not limited to, purified or partially purified clostridial toxin; recombinant single chain or dichain toxin with a naturally or non-naturally occurring sequence; chimeric toxin containing structural elements from multiple clostridial toxin species or subtypes; recombinant toxin light chain with a naturally occurring or non-naturally occurring sequence; bulk toxin; formulated product; cells or crude, fractionated or partially purified cell lysates including, without limitation, animal, insect, bacterial and other cells engineered to include a recombinant nucleic acid encoding a clostridial toxin or light chain thereof; bacterial, baculoviral and yeast lysates; raw, cooked, partially cooked or processed foods; beverages; animal feed; soil samples; water samples; pond sediments; lotions; cosmetics; and clinical formulations. It further is understood that the term sample encompasses tissue samples, including, without limitation, mammalian samples, primate samples and human samples, and further encompassing samples such as intestinal samples, for example, infant intestinal samples, and samples obtained from a wound. Thus, it is understood that a method of the invention can be useful, without limitation, to assay for clostridial toxin protease activity in a food or beverage sample; to assay a sample from a human or animal, for example, exposed to a clostridial toxin or having one or more symptoms of a clostridial toxicity; to follow activity during production and purification of clostridial toxin; or to assay formulated clostridial toxin products, including pharmaceuticals and cosmetics.

One skilled in the art understands that the methods of the invention are suitable for assaying any protein or molecule with clostridial toxin protease activity and do not rely, for example, on the ability of the clostridial toxin to bind to a neuronal cell or its ability to be internalized or translocated across the membrane. Thus, the methods of the invention are suitable for assaying for clostridial toxin protease activity of a clostridial toxin light chain, alone, and, although useful for assaying single or dichain heterotoxin, do not require the presence of the heavy chain. It further is understood that the methods of the invention are applicable to non-neuronal clostridial toxins including native and recombinant clostridial toxins, for example, clostridial toxins engineered to target pancreatic acinar or other non-neuronal cells.

Depending on the clostridial toxin protease activity which is to be assayed, a tagged toxin substrate included in a method of the invention will incorporate one of a variety of clostridial toxin recognition sequences. A method of the invention can be practiced, for example, with a botulinum toxin recognition sequence such as, without limitation, residues 134 to 206 of SEQ ID NO: 90, or another portion of SNAP-25. A method of the invention also can be practiced, for example, with a BoNT/A recognition sequence such as, without limitation, a BoNT/A recognition sequence containing at least six consecutive residues of SNAP-25, where the six consecutive residues encompass the sequence Gln-Arg. In addition, a method of the invention can be practiced, without limitation, with a BoNT/B recognition sequence such as a BoNT/B recognition sequence which includes at least six consecutive residues of VAMP, where the six consecutive residues encompass the sequence Gln-Phe. In still further embodiments, a method of the invention is practiced with a tagged toxin substrate in which the recognition sequence is a BoNT/C1 recognition sequence such as, without limitation, a BoNT/C1 recognition sequence which includes at least six consecutive residues of syntaxin, where the six consecutive residues encompass the sequence Lys-Ala, or a BoNT/C1 recognition sequence which includes at least six consecutive residues of SNAP-25, where the six consecutive residues encompass the sequence Arg-Ala.

A method of the invention also can be practiced, without limitation, with a BoNT/D recognition sequence such as a BoNT/D recognition sequence which includes at least six consecutive residues of VAMP, where the six consecutive residues encompass the sequence Lys-Leu. A method of the invention additionally can be practiced, without limitation, with a BoNT/E recognition sequence such as a BoNT/E recognition sequence which includes at least six consecutive residues of SNAP-25, the six consecutive residues encompassing the sequence Arg-Ile. In addition, a method of the invention can be practiced, without limitation, with a BoNT/F recognition sequence such as a BoNT/F recognition sequence which includes at least six consecutive residues of VAMP, the six consecutive residues encompassing the sequence Gln-Lys. A method of the invention further can be practiced, without limitation, with a BoNT/G recognition sequence such as a BoNT/G recognition sequence which includes at least six consecutive residues of VAMP, where the six consecutive residues encompass the sequence Ala-Ala. In a further embodiment, a method of the invention is practiced with a TeNT recognition sequence such as a TeNT recognition sequence which includes at least six consecutive residues of VAMP, where the six consecutive residues encompass the sequence Gln-Phe.

In the methods of the invention, a substrate can be cleaved with any of a variety of activities. In one embodiment, a method of the invention is practiced with a tagged toxin substrate under conditions such that the substrate is cleaved with an activity of at least 1 nanomole/minute/milligram toxin. In another embodiment, a method of the invention is practiced with a tagged toxin substrate under conditions such that the substrate is cleaved with an activity of at least 100 nanomoles/minute/milligram toxin. In a further embodiment, a method of the invention is practiced with a tagged toxin substrate under conditions such that the substrate is cleaved with an activity of at least 1000 nanomoles/minute/milligram toxin.

Any of a variety of second partners are useful in the invention including, but not limited to, cobalt ($Co^{2+}$) and nickel ($Ni^{2+}$). Furthermore, the second partner of the affinity couple can optionally be immobilized, for example, on a column or filter plate. In addition, a method of the invention may optionally include the step of assaying the amount of uncleaved tagged toxin substrate in the treated sample. It is understood that any of a variety of samples can be assayed in a method of the invention for determining clostridial toxin protease activity. Samples to be assayed according to a method of the invention encompass, without limitation, isolated clostridial toxins of any serotype; isolated clostridial light chains; formulated clostridial toxin products including, but not limited to, formulated BoNT/A; and whole or partially purified cellular extracts containing one or more recombinantly expressed clostridial toxins.

In a method of the invention, a variety of means can be used to separate a fluorescent or otherwise detectable cleavage product from stable complexes containing first and second partners of the affinity couple. Separation is generally performed by specific binding of the second partner of the affinity couple to components within the treated sample which contain the first partner of the affinity couple. As discussed above, by definition a fluorescent or otherwise detectable cleavage product does not contain the first partner of the affinity couple and, therefore, can be readily separated from all components within a treated sample which contain the first partner. As discussed further below, fluorescent or otherwise detectable cleavage products are separated from stable complexes using any of a variety of means including, but not limited to, metal chelate affinity chromatography.

Affinity purification, including metal chelate, immunoaffinity and other types of affinity purification techniques, can be used to separate a fluorescent or otherwise detectable cleavage product in a method of the invention. In one embodiment, the first partner of the affinity couple is a histidine tag. In another embodiment, the first partner of the affinity couple is glutathione-S-transferase (GST). In yet another embodiment, the first partner of the affinity couple is maltose-binding protein (MBP). In still another embodiment, the first partner of the affinity couple is a heterologous epitope.

In the methods of the invention, the second partner of an affinity couple can optionally be attached to a solid support. As used herein, the term "solid support" means an insoluble supporting material to which a second partner can be covalently attached. The term solid support includes, without limitation, affinity matrices including affinity beads or gels; resins including modified polystyrene; beads such as dextran and magnetic beads; and carbohydrate polymers such as agarose and Sepharose.

Where the first partner of an affinity couple is a histidine tag, metal chelate affinity chromatography (MCAC) can be useful for separating the fluorescent or otherwise detectable cleavage product. As used herein, the term "histidine tag" means a consecutive series of about 6 to 10 histidine residues that generally is solvent exposed. In one embodiment, a SNAP-25 or tagged toxin substrate of the invention includes the 6X-HIS tag HHHHHH (SEQ ID NO: 95). In another embodiment, a SNAP-25 or tagged toxin substrate of the invention includes the 10X-HIS tag HHHHHHHHHH (SEQ ID NO: 108).

Metal chelate chromatography is well known in the art as described in Ausubel et al., supra, 10.15, Supplement 41, and exemplified herein in Example II. Metal affinity tags useful in the invention include, without limitation, metal affinity peptides, which can be, for example, natural or synthetic mimics of a natural metal-binding site. A variety of metal affinity peptides and other metal affinity tags are known in the art as described, for example, in Enzelberger et al., *J. Chromatoqr. A.* 898:83-94 (2000), and include, without limitation, 6X-HIS, 7X-HIS, 8X-HIS, 9X-HIS and 10X-HIS tags (Mohanty and Weiner, *Protein Expr. Purif.* 33:311-325 (2004); and Grisshammer and Tucker, *Prot. Expr. Purif.* 11:53-60 (1997)). In metal chelate affinity purification, the second partner of the affinity couple is a metal ion such as a nickel ion ($Ni^{2+}$), copper ion ($Cu^{2+}$) or a cobalt ion ($Co^{2+}$). As non-limiting examples, the methods of the invention can be practiced using a bead such as Sepharose, for example, Sepharose CL-6B; a resin; or another solid support containing nickel or other metal ion immobilized by iminodiacetic acid (IDA) or nitrilotriacetic acid (NTA). Subsequent to separation of the fluorescent or otherwise detectable cleavage fragment (which does not contain a histidine or other metal affinity tag) from stable complexes containing the histidine tag-metal affinity couple, the stable complexes can optionally be eluted from the solid support using an acidic buffer or a buffer containing imidazole. One skilled in the art understands that a histidine tag also can be useful for immunoaffinity separation, as described further hereinbelow.

Glutathione-S-transferase (GST)/glutathione also can be an affinity couple useful in the methods of the invention. In this case, glutathione-S-transferase is incorporated into the SNAP-25 or tagged toxin substrate as the first partner of the affinity couple. Vectors for expression of GST-containing SNAP-25 or tagged toxin substrates in organisms such as *E. coli* and Baculovirus are well known in the art. Such vectors include the pGEX series of vectors and are commercially available from sources such as Becton Dickinson Biosciences and Amersham Pharmacia Biosciences (Piscataway, N.J.). In the methods of the invention where glutathione-S-transferase is the first partner of the affinity couple, fluorescent or otherwise detectable cleavage fragments (which do not contain glutathione-S-transferase) can be separated from components within the sample that contain glutathione-S-transferase using glutathione as the second partner of the affinity couple. Glutathione, for example, conjugated to agarose or other beads is commercially available from SIGMA, Amersham Pharmacia Biosciences and other sources. Free glutathione optionally serves to release stable complexes containing GST-glutathione from the beads or other solid support. Affinity chromatography using glutathione is well known in the art as described, for example, in Smith, *Methods Mol. Cell Biol.* 4:220-229 (1993), or Ausubel, supra, 2000 (see Chapter 16.7).

Maltose-binding protein/maltose also can be an affinity couple useful in the methods of the invention. In nature, maltose-binding protein (MBP) is encoded by the malE gene of *E. coli*. Vectors are commercially available for expression of a SNAP-25 or tagged toxin substrate containing a maltose-binding protein as a first partner of an affinity couple. Such vectors include pMAL vectors such as pMAL-c2e, -c2g, and -c2x, and pMAL-p2e, -p2g and p2x and are commercially available, for example, from sources such as New England Biolabs (Beverly, Mass.). In one embodiment, the second partner of the affinity couple is amylose, which is a polysaccharide consisting of maltose subunits. As a non-limiting example, the methods of the invention can be practiced using an amylose resin such as an agarose resin derivatized with amylose and commercially available from New England Biolabs. Thus, in the methods of the invention where maltose-binding protein is the first partner of the affinity couple, fluorescent or otherwise detectable cleavage fragments (which do not contain maltose-binding protein) can be separated from components within the treated sample that contain maltose-binding protein using amylose or another maltose-containing second partner. If desired, free maltose, such as column buffer containing 10 mM free maltose, can be used to elute the stable complexes bound to the amylose resin. Maltose affinity chromatography methods are routine and well known in the art as described, for example, in Ausubel, supra, 2000 (Chapter 16.6).

Biotin-streptavidin affinity systems also can be useful in the methods of the invention. As a non-limiting example, an 8 amino acid streptavidin tag is known in the art (Schmidt and Skerra, *Prot. Engin.* 6:109-122 (1993)) and are commercially available (SIGMA-Genosys).

The methods of the invention also can be practiced with a SNAP-25 or tagged toxin substrate which contains a heterologous epitope as the first partner of the affinity couple. Such a heterologous epitope provides a convenient means for separating the fluorescent or otherwise detectable cleavage product. As used herein in reference to an epitope, the term "heterologous" means an epitope derived from a gene which is different than the gene encoding the fused fluorescent protein or genetically encoded detectable marker and the gene encoding the clostridial toxin recognition sequence. Thus, for example, in a FLAG-SNAP25-GFP tagged toxin substrate of the invention, the "FLAG" component is a heterologous epitope which is not derived from the gene encoding SNAP-25. A variety of heterologous epitopes are well known in the art, including but not limited to, the FLAG epitope DYKDDDDK (SEQ ID NO: 91; Chubet and Brizzard, *BioTechniques* 20:136-141 (1996); the hemagluttinin (HA) epitope YPYDVPDYA (SEQ ID NO: 92); the c-myc epitope EQKLISEEDL (SEQ ID NO: 93), the AU1 epitope DTYRYI (SEQ ID NO: 94) and the 6-HIS epitope HHHHHH (SEQ ID NO: 95). One skilled in the art understands that these and other heterologous epitopes can be useful as first partners of an affinity couple in the substrates and methods of the invention.

As a non-limiting example, a SNAP-25 or tagged toxin substrate can include the FLAG tag DYKDDDDK (SEQ ID NO: 91) as the first partner of the affinity couple. The substrate can be produced by routine molecular methods, and the relative quantity of the resulting detectable cleavage product determined using anti-FLAG monoclonal antibodies commercially available, for example, from Eastman Kodak (Rochester, N.Y.) or Berkeley Antibody Company (BabCO; Richmond, Calif.). Similarly, the hemagluttinin (HA) epitope YPYDVPDYA (SEQ ID NO: 92) can be engineered into a SNAP-25 or tagged toxin substrate of the invention, and the relative quantity of the corresponding detectable cleavage fragment detected using anti-HA antibody or antiserum obtained from BabCO (Roche Diagnostics; Indianapolis, Ind.) or Santa Cruz Biotechnology. One can analogously engineer into a SNAP-25 or tagged toxin substrate the c-myc epitope EQKLISEEDL (SEQ ID NO: 93), such that the relative quantity of corresponding detectable cleavage product can be determined using antibody or antisera commercially available from sources such as BabCO, Invitrogen (San Diego, Calif.), Roche Diagnostics, SIGMA (St. Louis, Mo.) and Santa Cruz Biotechnology. Additional heterologous epitopes useful as first partners of an affinity couple include, without limitation, the AU1 tag DTYRYI (SEQ ID NO: 94) recognized by a monoclonal antibody available from BabCO, and the 6-HIS tag HHHHHH (SEQ ID NO: 95), which is recognized by antibodies and antisera available from BabCO, Invitrogen, SIGMA, Santa Cruz Biotechnology and other commercial sources. One skilled in the art understands that these and other heterologous epitopes can be conveniently used to separate a fluorescent or otherwise detectable cleavage product in a method of the invention.

Where the first partner of the affinity couple is a heterologous epitope, immunoprecipitation or another immunoaffinity separation procedure generally is used to separate the fluorescent or otherwise detectable cleavage product in a method of the invention. In immunoprecipitation, an antibody that recognizes the first partner of the affinity couple is attached to a sedimentable matrix such as, without limitation, protein A or protein G-agarose beads or Sepharose. Low-speed centrifugation can be performed to separate the solid-phase matrix and bound components containing the heterologous epitope, and unbound proteins removed by washing. A variety of immunoprecipitation protocols are routine and well known in the art, as described, for example, in Harlow and Lane, *Antibodies: A Laboratory Manual* (Cold Spring Harbor Laboratory Press, 1988); and Ausubel, supra, 2000 (see especially Chapter 10, Supplement 48, and Chapter 20, Supplement 46). Where the first partner of an affinity couple is a well known heterologous epitope such as, without limitation, a FLAG, hemagluttinin (HA), c-myc, AU1 or 6-HIS epitope, the antibodies or antiserum that specifically bind the epitope typically are commercially available from sources such as BabCO, Invitrogen, Roche Diagnostics, SIGMA and Santa Cruz Biotechnology, as described hereinabove. Antibodies against these and other heterologous epitopes also can be prepared by routine methods as described, for example, in Harlow and Lane, supra, 1988.

An antibody useful in immunoaffinity separation of fluorescent or otherwise detectable cleavage products can be polyclonal or monoclonal, or a pool of monoclonal antibodies, and, furthermore, can be an antigen-binding fragment of an antibody that retains a specific binding activity for the first partner of the affinity couple of at least about $1 \times 10^5$ M$^{-1}$. As non-limiting examples, antibody fragments such as Fab, F(ab')$_2$ and F$_v$ fragments can retain specific binding activity for a first partner of an affinity couple and, thus, can be useful in the invention. Furthermore, immunoaffinity separation can be performed with a non-naturally occurring antibody or fragment containing, at a minimum, one $V_H$ and one $V_L$ domain, for example, a chimeric antibody, humanized antibody or single chain Fv fragment (scFv) that specifically binds the first partner of the affinity couple. Such a non-naturally occurring antibody can be constructed using solid phase peptide synthesis, produced recombinantly, or obtained, for example, by screening combinatorial libraries consisting of variable heavy chains and variable light chains as described by Borrebaeck (Ed.), *Antibody Engineering* (Second edition) New York: Oxford University Press (1995)). If desired, an antibody can be attached to a solid support for immunoaffinity separation. Such solid supports include, without limitation, Sepharose, which is an insoluble, large-pore size chromatographic matrix. In one embodiment, an antibody is attached to Sepharose CL-4B, a 4% cross-linked agarose. Elution can be performed, for example, using brief exposure to high or low pH (Ausubel, supra, Chapter 10.11A, 2000).

As discussed further below, a variety of conditions suitable for clostridial toxin protease activity are useful in the methods of the invention. For example, conditions suitable for clostridial toxin protease activity can be provided such that at least 10% of the substrate is cleaved. Similarly, conditions suitable for clostridial toxin protease activity can be provided such that at least 20%, 30%, 40%, 50%, 60%, 70%, 80%, 90% or 95% of the SNAP-25 or tagged toxin substrate is cleaved, or such that 100% of the SNAP-25 or tagged toxin substrate is cleaved. In one embodiment, the conditions suitable for clostridial toxin protease activity are selected such that the assay is linear. In another embodiment, conditions suitable for clostridial toxin protease activity are provided such that at least 90% of the SNAP-25 or tagged toxin substrate is cleaved. In a further embodiment, conditions suitable for clostridial toxin protease activity are provided such that at most 25% of the SNAP-25 or tagged toxin substrate is cleaved. In yet further embodiments, conditions suitable for clostridial toxin protease activity are provided such that at most 5%, 10%, 15% or 20% of the SNAP-25 or tagged toxin substrate is cleaved.

In the methods of the invention, a sample is treated with a SNAP-25 or tagged toxin substrate in solution phase under conditions suitable for clostridial toxin protease activity. Exemplary conditions suitable for clostridial toxin protease activity are well known in the art, and further can be determined by routine methods. See, for example, Hallis et al., *J. Clin. Microbiol.* 34:1934-1938 (1996); Ekong et al., *Microbiol.* 143:3337-3347 (1997); Shone et al., WO 95/33850; Schmidt and Bostian, supra, 1995; Schmidt and Bostian, supra, 1997; Schmidt et al., supra, 1998; and Schmidt and Bostian, U.S. Pat. No. 5,965,699. It is understood that conditions suitable for clostridial toxin protease activity can depend, in part, on the specific clostridial toxin type or subtype being assayed and the purity of the toxin preparation. Conditions suitable for clostridial toxin protease activity generally include a buffer, such as HEPES, Tris or sodium phosphate, typically in the range of pH 5.5 to 9.5, for example, in the range of pH 6.0 to 9.0, pH 6.5 to 8.5 or pH 7.0 to 8.0. Conditions suitable for clostridial toxin protease activity also can include, if desired, dithiothreitol, β-mercaptoethanol or another reducing agent, for example, where a dichain toxin is being assayed (Ekong et al., supra, 1997). In one embodiment, the conditions include DTT in the range of 0.01 mM to 50 mM; in other embodiments, the conditions include DTT in the range of 0.1 mM to 20 mM, 1 to 20 mM, or 5 to 10 mM. If desired, an isolated clostridial toxin or sample can be pre-incubated with a reducing agent, for example, with 10 mM dithiothreitol (DTT) for about 30 minutes prior to addition of SNAP-25 or tagged toxin substrate.

Clostridial toxins are zinc metalloproteases, and a source of zinc, such as zinc chloride or zinc acetate, typically in the range of 1 to 500 μM, for example, 5 to 10 μM can be included, if desired, as part of the conditions suitable for clostridial toxin protease activity. One skilled in the art understands that zinc chelators such as EDTA generally are excluded from a buffer for assaying clostridial toxin protease activity.

Conditions suitable for clostridial toxin protease activity can optionally include a detergent such as TWEEN-20, which can be used, for example, in place of bovine serum albumin. TWEEN-20 can be provided, for example, in the range of 0.001% to 10% (v/v) Tween-20, or in the range of 0.01% to 1.0% (v/v) Tween-20. In one embodiment, TWEEN-20 is provided at a concentration of 0.1% (v/v; see Example II).

Conditions suitable for clostridial toxin protease activity can optionally include a detergent such as TWEEN-20 (polyoxyethylene (20) sorbitan monolaureate), which can be used, for example, in place of bovine serum albumin. TWEEN-20® (polyoxyethylene (20) sorbitan monolaureate) can be provided, for example, in the range of 0.001% to 10% (v/v) TWEEN-20® (polyoxyethylene (20) sorbitan monolaureate), or in the range of 0.01% to 1.0% (v/v) Tween-20® (polyoxyethylene (20) sorbitan monolaureate). In one embodiment, TWEEN-20® (polyoxyethylene (20) sorbitan monolaureate) is provided at a concentration of 0.1% (v/v; see Example II).

The amount of SNAP-25 or tagged toxin substrate can be varied in a method of the invention. A SNAP-25 or tagged toxin substrate can be supplied, for example, at a concentration of 1 μM to 500 μM, 1 μM to 50 μM, 1 μM to 30 μM, 5 μM to 20 μM, 50 μM to 3.0 mM, 0.5 mM to 3.0 mM, 0.5 mM to 2.0 mM, or 0.5 mM to 1.0 mM. The skilled artisan understands that the concentration of SNAP-25 or tagged toxin substrate or the amount of sample can be limited, if desired, such that the assay is linear. In one embodiment, a method of the invention relies on a SNAP-25 or tagged toxin substrate concentration of less than 100 μM. In further embodiments, a method of the invention relies on a SNAP-25 or tagged toxin substrate concentration of less than 50 μM or less than 25 μM. In a further embodiment, a method of the invention relies on a SNAP-25 or tagged toxin substrate concentration of 10 μM to 20 μM. If desired, a linear assay also can be performed by mixing SNAP-25 or tagged toxin substrate with corresponding, "unlabeled" substrate which lacks the green fluorescent protein, or fluorescent protein or genetically encoded detectable marker. The appropriate dilution can be determined, for example, by preparing serial dilutions of SNAP-25 or tagged toxin substrate in the corresponding unlabeled substrate.

The concentration of purified or partially purified clostridial toxin assayed in a method of the invention generally is in the range of about 0.1 pM to 100 nM, for example, 1 pM to 2000 pM, 1 pM to 200 pM, 1 pM to 50 pM, 1 to 200 nM, 1 to 100 nM or 3 to 100 nM toxin, which can be, for example, purified native or recombinant light chain or dichain toxin or formulated clostridial toxin product containing human serum albumin and excipients. In particular embodiments, the concentration of purified or partially purified recombinant BoNT/A or BoNT/E light chain or dichain or formulated toxin product is in the range of 1 pM to 2000 pM, 10 pM to 2000 pM, 20 pM to 2000 pM, 40 pM to 2000 pM, or 1 pM to 200 pM. In further embodiments, the concentration of purified or partially purified recombinant BoNT/C light chain or dichain or formulated toxin product is in the range of 1 to 200 nM, 4 to 100 nM, 10 to 100 nM or 4 to 60 nM. One skilled in the art understands that the concentration of purified or partially purified clostridial toxin will depend on the serotype of the toxin assayed, as well as the purity of the toxin, the presence of inhibitory components, and the assay conditions. It is additionally understood that purified, partially purified or crude samples can be diluted to within a convenient range for assaying for clostridial toxin protease activity against a standard curve. Similarly, it is understood that a sample can be diluted, if desired, such that the assay for toxin protease activity is linear.

Conditions suitable for clostridial toxin protease activity also generally include, for example, temperatures in the range of about 20° C. to about 45° C., for example, in the range of 25° C. to 40° C., or the range of 35° C. to 39° C. Assay volumes often are in the range of about 5 to about 200 μl, for example, in the range of about 10 μl to 100 μl or about 0.5 μl to 100 μl, although nanoliter reaction volumes also can be used with the methods of the invention. Assay volumes also can be, for example, in the range of 100 μl to 2.0 ml or in the range of 0.5 ml to 1.0 ml.

Assay times can be varied as appropriate by the skilled artisan and generally depend, in part, on the concentration, purity and activity of the clostridial toxin. Assay times generally vary, without limitation, in the range of about 15 minutes to about 5 hours. As non-limiting examples, exemplary assay times include incubation, for example, at 37° C. for 30 minutes, 45 minutes, 60 minutes, 75 minutes or 90 minutes (see Example III). In particular embodiments, at least 10%, 20%, 30%, 40%, 50%, 60%, 70%, 80%, 90%, 95% or 100% of the SNAP-25 or tagged toxin substrate is cleaved. In further embodiments, the protease reaction is stopped before more than 5%, 10%, 15%, 20%, 25% or 50% of the SNAP-25 or tagged toxin substrate is cleaved. Protease reactions can be terminated by the appropriate reagent, which generally depends on the fluorescent protein or other detectable marker in the substrate. As a non-limiting example, a protease reaction based on a GFP-containing substrate can be terminated by addition of a terminating reagent such as guanidinium chloride, for example, to a final concentration of 1 to 2 M as in Example II. Protease reactions also can be terminated by addition of $H_2SO_4$; addition of about 0.5 to 1.0 M sodium borate, pH 9.0 to 9.5; or addition of zinc chelators. One skilled in the art understands that protease reactions can be terminated, if desired, prior to contacting the treated sample with a second partner of the affinity couple.

As a non-limiting example, conditions suitable for clostridial toxin protease activity such as BoNT/A protease activity can be incubation at 37° C. for 90 minutes in a buffer containing 50 mM HEPES (pH 7.2), 10 μM $ZnCl_2$, 10 mM DTT, and 0.1% (v/v) TWEEN-20® (polyoxyethylene (20) sorbitan monolaureate) with 10-16 μM substrate (see Example II). If desired, BoNT/A, particularly dichain BoNT/A, can be preincubated with dithiothreitol, for example, for 20 or 30 minutes before addition of substrate. As a further non-limiting example, conditions suitable for BoNT/A protease activity can be incubation at 37° C. in a buffer such as 30 mM HEPES (pH 7.3) containing a reducing agent such as 5 mM dithiothreitol; and a source of zinc such as 25 μM zinc chloride (approximately 7 nM; Schmidt and Bostian, supra, 1997). BSA in the range of 0.1 mg/ml to 10 mg/ml, for example, 1 mg/ml BSA, also can be included when a sample is treated with a SNAP-25 or tagged toxin substrate (Schmidt and Bostian, supra, 1997). As still a further non-limiting example, conditions suitable for clostridial toxin protease activity, for example BoNT/B activity, can be incubation in 50 mM HEPES, pH 7.4, with 10 μM zinc chloride, 1% fetal bovine serum and 10 mM dithiothreitol, with incubation for 90 minutes at 37° C. (Shone and Roberts, *Eur. J. Biochem.* 225:263-270 (1994); Hallis et al., supra, 1996); or can be, for example, incubation in 40 mM sodium phosphate, pH 7.4, with 10 mM dithiothreitol, optionally including 0.2% (v/v) Triton X-100, with incubation for 2 hours at 37° C. (Shone et al., supra, 1993). Conditions suitable for tetanus toxin protease activity or other clostridial toxin protease activity can be, for example, incubation in 20 mM HEPES, pH 7.2, and 100 mM NaCl for 2 hours at 37° C. with 25 μM peptide substrate (Cornille et al., supra, 1994).

In a method of the invention for determining clostridial toxin protease activity, a sample is treated with a tagged toxin substrate containing (i) a fluorescent protein or other genetically encoded detectable marker; (ii) a first partner of an affinity couple; and (iii) a clostridial toxin recognition sequence that includes a cleavage site which intervenes between the fluorescent protein and the first partner of the affinity couple. If desired, a second tagged toxin substrate can be included; this second substrate contains a second fluorescent protein or other genetically encoded detectable marker and a second first partner of an affinity couple as well as a second clostridial toxin recognition sequence including a second cleavage site that is cleaved by a different clostridial toxin than the toxin that cleaves the first cleavage site within the first clostridial toxin recognition sequence. The fluorescent protein or other genetically encoded detectable marker and the first partner of an affinity couple in the second substrate can be the same or different from those in the first substrate. In this way, a single sample can be conveniently assayed for the presence of multiple clostridial toxins.

It is understood that one can assay for any combination of clostridial toxins, for example, two, three, four, five, six, seven, eight, nine, ten or more clostridial toxins. One can assay, for example, any combination of two, three, four, five, six, seven or eight of TeNT, BoNT/A, BoNT/B, BoNT/C1, BoNT/D, BoNT/E, BoNT/F and BoNT/G. For example, seven substrates, each containing the same fluorescent or other genetically encoded detectable protein and same first partner of an affinity couple flanking a BoNT/A, BoNT/B, BoNT/C1, BoNT/D, BoNT/E, BoNT/F or BoNT/G recognition sequence can be treated with a sample in solution phase under conditions suitable for botulinum toxin protease activity before contacting the treated sample with a second partner of the affinity couple. The presence of fluorescent cleavage product is indicative of clostridial toxin protease activity of at least one botulinum toxin. Such an assay can be useful, for example, for assaying food samples or tissue samples for the presence of any botulinum toxin and can be combined, if desired, with one or more subsequent assays for individual botulinum toxins or specific combinations of botulinum toxins.

In another embodiment, a single sample is assayed for two or more different clostridial toxins using two or more different tagged toxin substrates with each substrate containing a different fluorescent protein or other genetically encoded detectable marker. The use of multiple substrates can be useful for extending the dynamic range of the assay, as described, for example, in U.S. Pat. No. 6,180,340. As an example of the use of multiple tagged toxin substrates, a single sample can be assayed for BoNT/A and BoNT/B protease activity using a first tagged toxin substrate containing a green fluorescent protein and a BoNT/A recognition sequence, and a second tagged toxin substrate containing a red fluorescent protein and a BoNT/B recognition sequence. If desired, the two substrates can utilize the same first partner of an affinity couple, such as a histidine tag. Subsequent to contacting the treated sample with a second partner of the affinity couple and separating fluorescent cleavage product from stable complexes, a green fluorescent cleavage product is indicative of BoNT/A protease activity while a red fluorescent cleavage product is indicative of BoNT/B protease activity, and both green and red fluorescent cleavage products are indicative of BoNT/A and BoNT/B cleavage products.

Multiple substrates also can be used in the methods of the invention to extend the range of the assay. For example, at least two tagged toxin substrates are used together at different dilutions; the substrates have different fluorescent proteins or other genetically encoded detectable markers and, therefore, are separately detectable, but have recognition sequences for the same clostridial toxin. In one embodiment, otherwise identical tagged toxin substrates with different fluorescent proteins or other genetically encoded detectable markers are used together at different dilutions to extend the dynamic range of a method of the invention.

One or more controls may optionally be utilized in the methods of the invention. A control substrate typically is the same SNAP-25 or tagged toxin substrate which is treated with a defined sample containing one or more clostridial toxins; the same SNAP-25 or tagged toxin substrate which is not treated with any sample; or a non-cleavable form of the SNAP-25 or tagged toxin substrate. One skilled in the art understands that a variety of control substrates are useful in the methods of the invention and that a control substrate can be a positive control substrate or a negative control substrate. A control substrate can be, for example, a negative control such as a similar or identical substrate that is contacted with a similar sample that does not contain active clostridial toxin, or that is not contacted with any sample. A control cleavage product, similar or identical to the fluorescent or otherwise detectable cleavage product, also can be useful in the methods of the invention.

It is understood that the methods of the invention can be automated and, furthermore, can be configured in a high-throughput or ultra high-throughput format using, for example, 96-well, 384-well or 1536-well plates. As one example, fluorescence emission can be detected using Molecular Devices FLIPR instrumentation system (Molecular Devices; Sunnyvale, Calif.), which is designed for 96-well plate assays (Schroeder et al., *J. Biomol. Screening* 1:75-80 (1996)). FLIPR utilizes a water-cooled 488 nm argon ion laser (5 watt) or a xenon arc lamp and a semiconfocal optimal system with a charge-coupled device (CCD) camera to illuminate and image the entire plate. The FPM-2 96-well plate reader (Folley Consulting and Research; Round Lake, Ill.) also can be useful in detecting fluorescence emission in the methods of the invention. One skilled in the art understands that these and other automated systems with the appropriate spectroscopic compatibility such as the ECLIPSE cuvette reader (Varian-Cary; Walnut Creek, Calif.), the SPECTRA$_{max}$ GEMINI XS (Molecular Devices) and other systems from, for example, Perkin Elmer can be useful in the methods of the invention.

The following examples are intended to illustrate but not limit the present invention.

EXAMPLE I

Expression and Characterization of Recombinant GFP-SNAP-25 Substrates

This example describes construction of plasmids for expression of GFP-SNAP25$_{(134-206)}$ and SNAP25$_{(134-206)}$-GFP substrates as well as control substrates containing modified cleavage sites.

Two GFP substrates containing the same components, but present in the opposite orientations were designed and expressed. Each substrate was a fusion protein consisting of green fluorescent protein (GFP), murine SNAP-25 residues 134-206, and a polyhistidine affinity tag (6xHis), with each component separated by peptide linkers. As described further below, the substrates were designed such that the GFP and polyhistidine tag were fused to opposite termini of SNAP25$_{(134-206)}$. The fusion protein substrates were designated GFP-SNAP25 and SNAP25-GFP.

A. Construction of pDQE50/BirASNAP$_{(128-206)}$

The SNAP-25 sequence was obtained from pT25FL, a plasmid which contains the full-length mouse SNAP-25 gene inserted in frame with the 3' terminus of the glutathione-S-transferase (GST) gene (GST-SNAP25$_{(1-206)}$), provided by Professor Dolly (O'Sullivan et al., *J. Biol. Chem.* 274:36897-36904 (1999)). The SNAP-25 sequence from pT25FL was incorporated into a second expression vector, which was designed to have a BirAsp signal sequence for biotinylation and a polyhistidine affinity tag fused to the N-terminus of residues 134 to 206 of SNAP-25 (BirAsp-polyHis-SNAP25$_{(134-206)}$, denoted "BA-SNAP"). The DNA sequence encoding SNAP25$_{(134-206)}$ was generated by PCR amplification of the appropriate region of the pT25FL plasmid with PCR primers 5'-GCT <u>AGATCT</u> CGA GTT MC CAC TTC CCA GCA TCT TTG-3' (SEQ ID NO: 104; antisense) and 5'-ATC CGG AGG GTA ACA AAC GAT GCC-3' (SEQ ID NO: 101; sense) to produce a SNAP25$_{(134-206)}$ PCR product containing a Bgl II restriction site (PCR product A).

The BirAsp sequence, a natural substrate for biotinylation, as well as a polyhistidine affinity tag, were engineered for fusion upstream and in frame with the SNAP25$_{(134-206)}$ sequence using synthetic oligonucleotides SEQ ID NOS: 102 and 103, which contained a 20 bp complementary region. These oligonucleotides, 5'-CGA ATT CCGCGG GCC ACC ATG GGA GGA GGA CTG MC GAC ATC TTC GAG GCT CM MG ATC-3' (SEQ ID NO: 102; sense; Sac II site underlined) and 5'-TCG TTT GTT ACC CTC CGG ATA TGA TGA TGA TGA TGA TGA TGA TGG GAT CCA TGC CAC TCG ATC TTT TGA GCC TCG MG A-3' (SEQ ID NO: 103; antisense), were annealed, and the single strand overhangs filled by PCR amplification to yield PCR product B.

The two double stranded PCR products containing the coding sequences for SNAP25$_{(134-206)}$, denoted PCR product A, and BirAsp and polyhistidine, denoted PCR product B, were denatured and annealed. The 20 bp complementary sequence in the two gene fragments is shown in italics in PCR primers SEQ ID NO: 101 and SEQ ID NO: 103). After filling in the overhangs by PCR, the product was amplified with primers SEQ ID NO: 102 and SEQ ID NO: 104. The resulting PCR product, which encoded BirAsp-polyHis-SNAP25$_{(134-206)}$ (designated "BA-SNAP"), was digested with SacII and BglII, and the isolated gene insert ligated into pQBI25fA2 vector digested with SacI and BamHI, to yield plasmid pNTP12 (pQBI25fA2 containing BA-SNAP).

For expression and purification from *E. coli*, the BA-SNAP gene was transferred into a pTrc99A plasmid (Amersham Pharmacia Biotech). The BA-SNAP gene was isolated from pNTP12 by digestion with NcoI and XhoI followed by gel purification. Separately, the pTrc99A plasmid was digested with NcoI and SalI, and the isolated vector ligated to the BA-SNAP gene to yield plasmid pNTP14 (pTrc99A containing BA-SNAP).

For cloning of the BA-SNAP gene into plasmid pQE-50, the A-SNAP fragment was PCR amplified from pNTP14 with primer SEQ ID NO: 104 and primer SEQ ID NO: 105 (5'-CGA AGA TCT GGA GGA CTG MC GAC ATC TTC-3' (sense; Bgl II site underlined)). After digestion with BglII and XhoI, the amplified PCR product was ligated into vector pQE-50, which had been digested with BamH I and Sal I. The resulting plasmid, which represents pQE50 containing BA-SNAP, was designated pNTP26.

B. Construction of GFP-SNAP-25 Expression Vectors

Figure 8A:
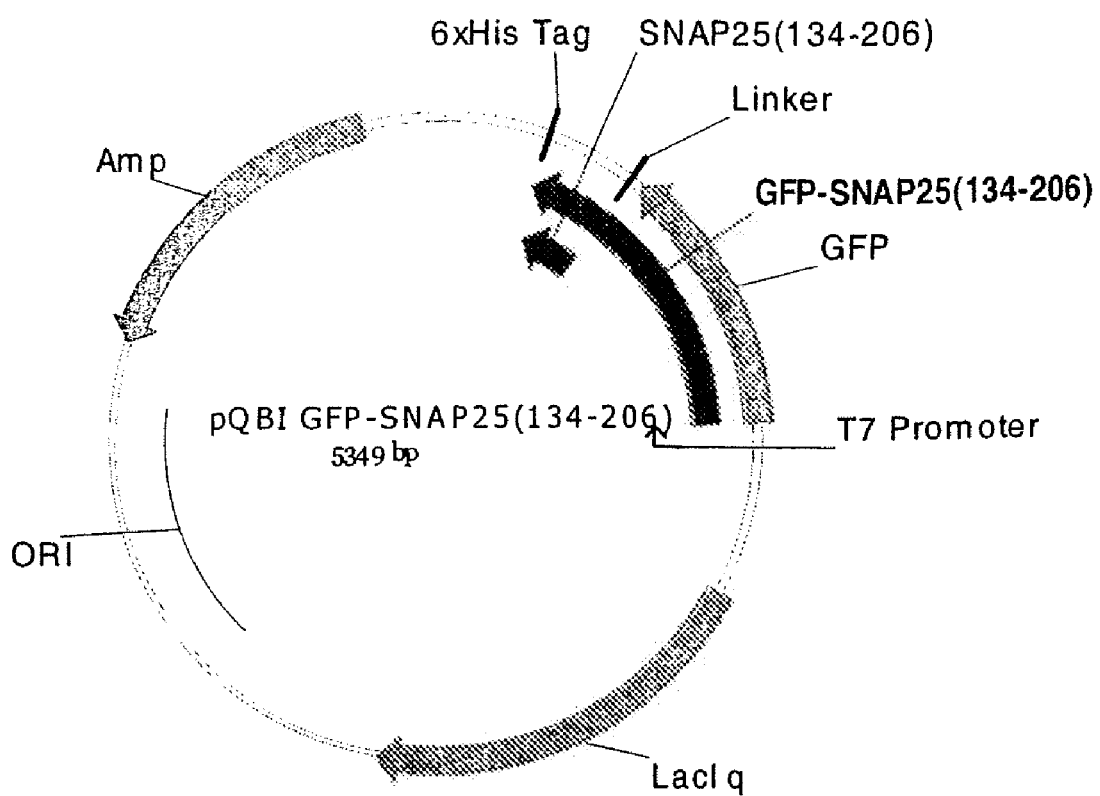
FIG. 8 shows (A) a schematic of plasmid pQBI GFP-$SNAP25_{(134-206)}$ and (B) the nucleic acid and amino acid sequences (SEQ ID NOS: 85 and 86) of GFP-$SNAP25_{(134-206)}$-6XHIS.
Figure 9A:
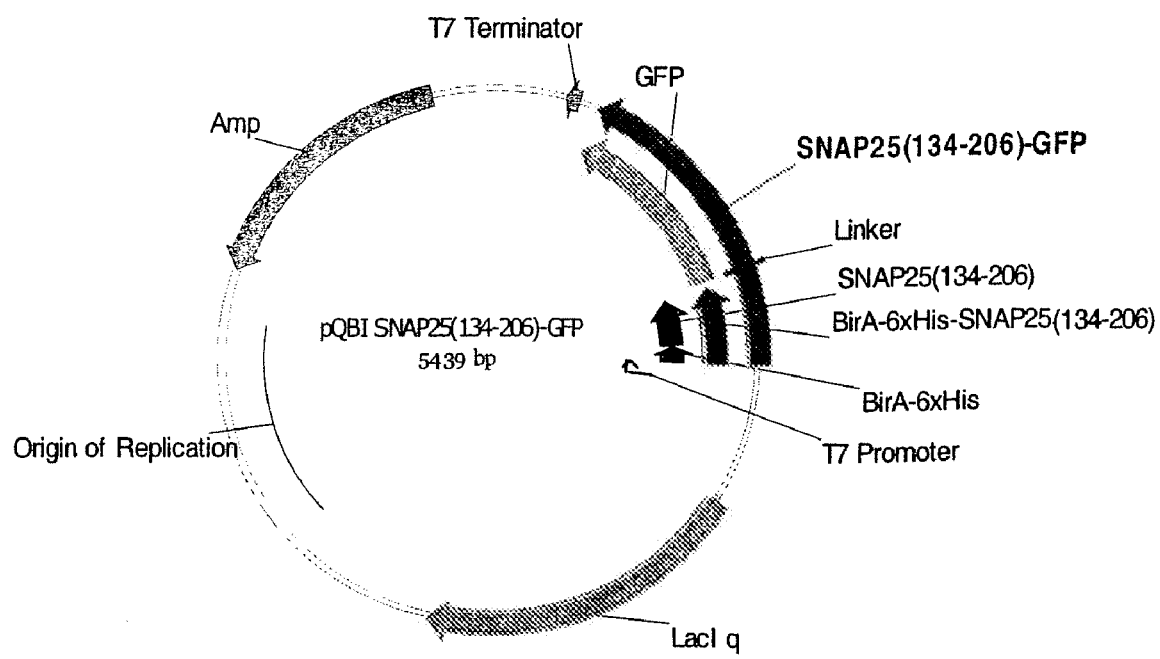
FIG. 9 shows (A) a schematic of plasmid pQBI $SNAP25_{(134-206)}$-GFP and (B) the nucleic acid and amino acid sequences (SEQ ID NOS: 87 and 88) of 6XHIS-$SNAP25_{(134-206)}$-GFP.

Plasmids encoding the green fluorescent protein (GFP) fusion protein substrates were prepared by modifying vector pQBI T7-GFP (Quantum Biotechnologies; Carlsbad, Calif.) as described below. The plasmid maps are shown in FIGS. 8A and 9A below. The nucleic acid and predicted amino acid sequence for the GFP-SNAP25$_{(134-206)}$ and SNAP25$_{(134-206)}$-GFP substrates are shown in FIGS. 8B and 9B, respectively.

Plasmid pQBI GFP-SNAP25$_{(134-206)}$ was constructed in two phases as follows. First, vector pQBI T7-GFP was PCR-modified to remove the stop codon at the 3' terminus of the GFP-coding sequence and to insert the coding sequence for a portion of the peptide linker separating GFP from the SNAP-25 fragment. Second, a DNA fragment coding for SNAP-25$_{(134-206)}$ was PCR amplified from pNTP26 using PCR primers designed to incorporate the coding sequence for the remainder of the peptide linker fused 5' to the SNAP-25$_{(134-206)}$ gene and a 6xHis affinity tag fused 3' of the gene. The resultant PCR product was cloned into the modified pQBI vector described above to yield the pQBI GFP-SNAP25$_{(134-206)}$ plasmid (see FIG. 8A) for expression of GFP-SNAP25$_{(134-206)}$-6xHis.

Plasmid pQBI SNAP25$_{(134-206)}$-GFP was constructed as follows. Plasmid pQBI SNAP25$_{(134-206)}$-GFP, shown in FIG. 9B, was constructed by subcloning a PCR amplified gene containing the BirAsp biotinylation sequence, a poly-His affinity tag, and SNAP25 residues 134-206 into pQBI T7-GFP. The entire BirAsp, 6xHis, and SNAP25$_{(134-206)}$ gene from pNTP26 was PCR amplified using primers designed to incorporate the coding sequence for a fusion protein linker 3' of the amplified gene and to facilitate fusion to the 5' terminus of the GFP gene, yielding a single gene for expression of BirAsp-6xHis-SNAP25$_{(134-206)}$-linker-GFP as shown in FIG. 9B.

C. Construction of Vectors Encoding SNAP-25/GFP Expression Vector Variants

Modification of vector pQBI GFP-SNAP25$_{(134-206)}$ to create the Arg198Ala and Arg180Asp analogues was performed using primers 5'-GATGAAGCCAA CCAAGCTGCAA-CAAAGATGCTG-3' (SEQ ID NO: 106; "SNAP25 (R198A)") and 5'-CGCCAGATCGACGATATCATG-GAGAAGGCTG-3' (SEQ ID NO: 107; "SNAP25(R180D)") along with their complementary sequences.

For each pair of primers, six 50 μL PCR reactions were assembled containing 5 μL 10×Pfu Buffer (Stratagene; La Jolla, Calif.), 1 μL dNTPs (12.5 mM each; Promega; Madison, Wis.), 1 μL Pfu Turbo DNA polymerase (Stratagene; hot start addition), varying concentrations of template DNA (10 to 100 ng pQBI GFP-SNAP25$_{134-206)}$ and each primer at a final concentration of 0.2 μM. The reactions were brought to a final volume of 50 μL with nuclease-free water. Following incubation at 95° C. for 2 minutes, 25 cycles of amplification were performed (95° C. for 1 minute; 60° C. for 30 seconds; and 72° C. for 12 minutes), followed by a final 72° C. extension for 7 minutes.

Following thermocycling, 1 μL DpnI restriction enzyme (Stratagene) was added to each reaction and incubated for one hour at 37° C. to digest template DNA. The reactions were purified by QIAquick kit (Qiagen; Valencia, Calif.) and analyzed by agarose gel electrophoresis. All but one of the reactions produced full-length plasmid. Sequencing of the candidate plasmids revealed one Arg180Asp variant and two Arg198Ala variants containing the desired changes.

D. Expression and Purification of GFP-SNAP25 Substrate

The expression vectors described above were transformed into *E. coli* BL21(DE3) cells (Novagen; Madison, Wis.; or Invitrogen; Carlsbad, Calif.) or into *E. coli* BL21 CODON-PLUS® (DE3)-RIL cells (Stratagene) containing the T7 RNA polymerase gene. Transformed cells were selected on LB(amp) plates overnight at 37° C. Single colonies were used to inoculate 1-3 mL starter cultures which were in turn used to inoculate 0.5 to 1.0 L cultures. The large cultures were grown at 37° C. with shaking until A$_{595}$ reached 0.5-0.6, at which time they were removed from the incubator and were allowed to cool briefly. After induction of protein expression with 1 mM IPTG, GFP-SNAP25 substrate was expressed from the pQBI GFP-SNAP25$_{(134-206)}$ plasmid overnight with shaking at 16° C. in order to facilitate folding of the GFP moiety. Cells from 250 mL aliquots of the expression cultures were collected by centrifugation (30 minutes, 6,000×g, 4° C.) and stored at −80° C. until needed.

Substrates were purified at 4° C. by a two-step procedure involving IMAC purification, followed by a de-salting step to remove imidazole, typically yielding greater than 150 mg/L of purified substrate, as follows. Cell pellets from 250 mL cultures were each resuspended in 7-12 mL Column Binding Buffer (25 mM HEPES, pH 8.0; 500 mM NaCl; 1 mM β-mercaptoethanol; 10 mM imidazole), lysed by sonication (1 minute 40 seconds in 10-second pulses at 38% amplitude), and clarified by centrifugation (16000 rpm, 4° C., 1 hour). Affinity resin (3-5 mL Talon SuperFlow $Co^{2+}$ per cell pellet) was equilibrated in a glass or disposable column support (Bio-Rad) by rinsing with 4 column volumes of sterile dd$H_2O$ and 4 column volumes of Column Binding Buffer. Clarified lysate was applied to the column in one of two ways: (1) Lysate was added to the resin and batch bound by horizontal incubation for 1 hour with gentle rocking or (2) Lysate was applied to the vertical column and allowed to enter the column slowly by gravity flow. Following batch binding only, the column was righted and the solution drained, collected, and passed over the resin again. In both cases, after the lysate had been applied, the column was washed with 4-5 column volumes of Column Binding Buffer. In some cases, the column was further washed with 1-2 column volumes of Column Wash Buffer (25 mM HEPES, pH8.0; 500 mM NaCl; 1 mM β-mercaptoethanol; 20 mM imidazole). Protein was eluted with 1.5 to 2.0 column volumes of Column Elution Buffer (25 mM HEPES, pH 8.0; 500 mM NaCl; 1 mM β-mercaptoethanol; 250 mM imidazole), which was collected in fractions of ~1.4 mL. The green fractions were combined and desalted by FPLC (BioRad Biologic DuoLogic, QuadTec UV-Vis detector) with a HiPrep 26/10 size exclusion column (Pharmacia) and an isocratic mobile phase of chilled Fusion Protein Desalting Buffer (50 mM HEPES, pH 7.4, 4° C.) at a flow rate of 10 mL/minute. Desalted protein was collected as a single fraction, concentrated in an Apollo 20-mL concentrator (QMWL 10 kDa; Orbital Biosciences), and the concentration determined using a BioRad Protein Assay. The GFP-SNAP25 substrate was monomeric as demonstrated by size-exclusion chromatography. The protein solution was subsequently divided into 500 μL aliquots, flash-frozen with liquid nitrogen and stored at −80° C. Once defrosted, a working aliquot was stored at 4° C., protected from light.

E. Characterization of GFP-SNAP25 Substrates

Figure 10:
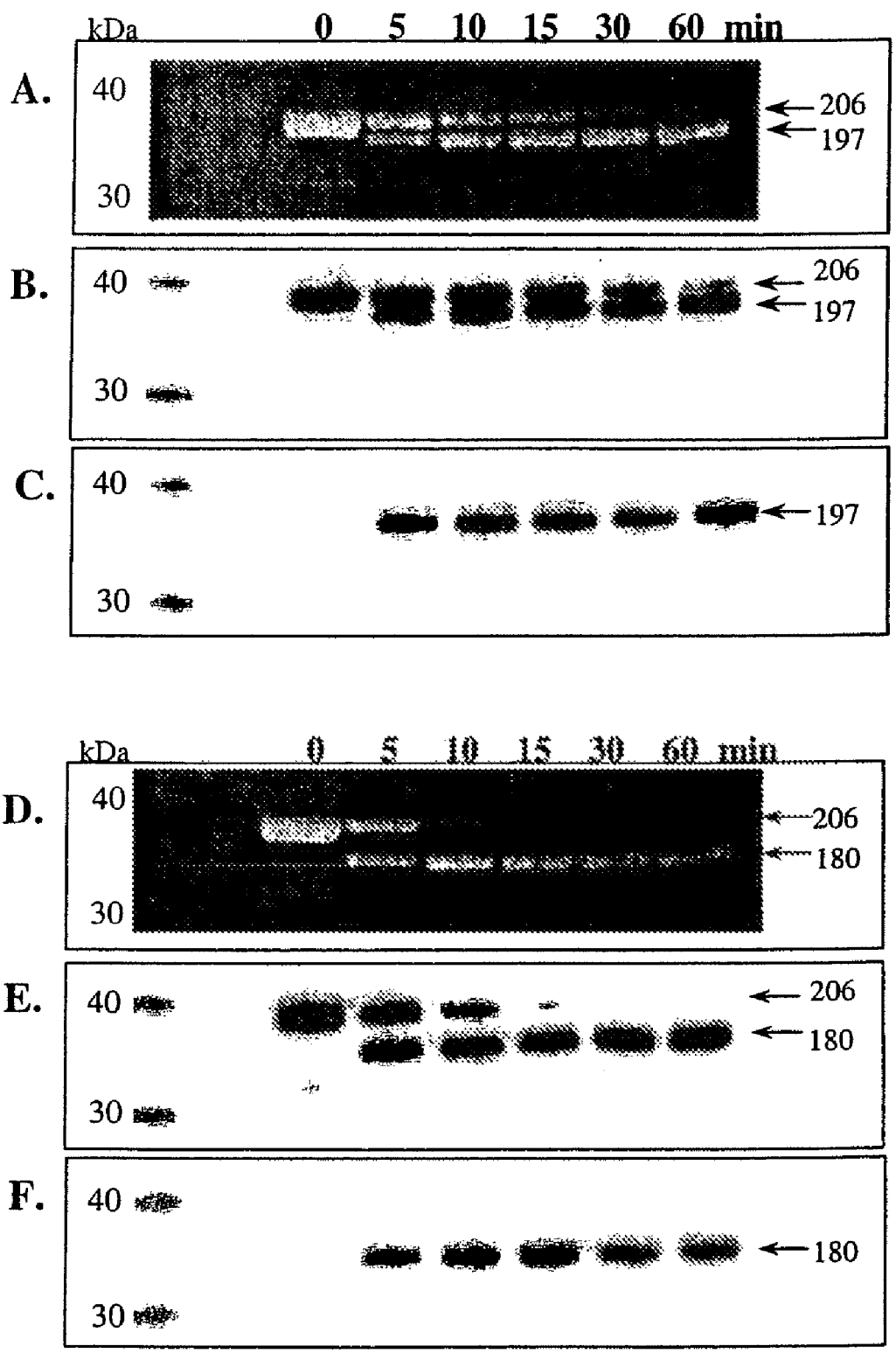
FIG. 10 shows SDS-PAGE and Western blot analysis of rLC/A and BoNT/E proteolysis reactions. A, B, and C show rLC/A proteolytic reactions, while D, E, and F show BoNT/E proteolytic reactions. (A) Sypro Ruby stained SDS-PAGE of samples incubated with rLC/A for 0, 5, 10, 15, 30, and 60 minutes. (B) Western blot probing with anti-GFP primary antibody. (C) Western blot probing with an antibody specific to the C-terminus of the $SNAP25_{197}$ proteolysis product. The protein bands were identified as 206 for the complete GFP-$SNAP25_{(134-206)}$ moiety and as 197 for rLC/A-processed GFP-$SNAP25_{(134-197)}$. (D) Sypro Ruby stained SDS-PAGE of samples incubated with BoNT/E for 0, 5, 10, 15, 30, and 60 minutes. (E) Western blot probing with anti-GFP primary antibody. (F) Western blot probing with an antibody specific to the C-terminus of the $SNAP25_{180}$proteolysis product. The protein bands identified as 206 represent the complete GFP-$SNAP25_{(134-206)}$ moiety and those identified as 180 represent BoNT/E-processed GFP-$SNAP25_{(134-180)}$. (G) Schematic summary of the GFP-SNAP fluorescence release assay.

As shown in FIGS. 10A-C, the specificity of Type A toxin for the Q197-R198 scissile bond of GFP-SNAP25 was verified by SDS-PAGE and Western blot analysis of substrate cleaved by rLC/A. Similarly it was demonstrated that proteolysis of GFP-SNAP25 with BoNT/E yields the expected GFP-SNAP25(134-180) product (FIGS. 10D-F). These results demonstrate that a synthetic substrate containing GFP and a histidine tag as well as a portion of SNAP-25 containing a clostridial toxin recognition sequence and cleavage site can be an effective substrate for the relevant clostridial toxin.

SDS-PAGE and Western blot analysis of BoNT/A and BoNT/E proteolytic reactions were performed as follows. $GFP\text{-}SNAP25_{134\text{-}206}$ substrate (0.4 mg/mL) was combined with either single-chain native BoNT/E (50.0 μg/mL), or rLC/A (0.1 μg/mL) in toxin reaction buffer (50 mM HEPES pH 7.4, 0.1 μg/mL BSA, 10 μM $ZnCl_2$, 10 mM DTT). The reactions were incubated at 37° C., with aliquots removed after incubation for 0, 5, 10, 15, 30, and 60 minutes and quenched by addition to gel loading buffer. Reaction mixtures were analyzed by SDS-PAGE (10% Bis-Tris MOPS) and staining with Sypro Ruby (Bio-Rad) or were transferred to nitrocellulose membranes and probed with antibodies specific for GFP, $SNAP25_{134\text{-}197}$, or $SNAP25_{134\text{-}180}$.

F. Expression and Identification of Cell Lysates Containing Active Recombinant BoNT Types A and E Crude, clarified BL21-Codon Plus cell lysates were prepared as follows. Chemically competent *E. coli*BL21 CODONPLUS® (DE3)-RIL cells (Stratagene) were transformed with a pET vector to provide kanamycin resistance, spread on LB/kan (50 μg/mL) plates and incubated overnight at 37° C. A 3 mL culture grown from a single colony was used to inoculate a 175 mL culture, which was incubated overnight with shaking at 37° C. The cells were pelleted by centrifugation, resuspended in 10 mL 25 mM HEPES buffer, pH 7.4, and lysed by sonication (1 minute 40 seconds in 10-sec pulses at 38% amplitude). The lysate was cleared by centrifugation (16,000 rpm, 4° C., 1 hour), divided into 0.4 mL aliquots, flash-frozen with liquid nitrogen and stored at −80° C. The protein content of the cleared lysate was determined to be 0.7 mg/mL by the BioRad Protein Assay.

TOP10® cell lysates were prepared as follows. Joanne Wang provided a 20 mL culture of ampicillin-resistant *E. coli* TOP10 cells (Invitrogen). Cells were pelleted by centrifugation and resuspended in 2 mL Toxin Reaction Buffer without DTT (50 mM HEPES, pH 7.4; 0.1% (v/v) TWEEN-20® (polyoxyethylene (20) sorbitan monolaureate); 10 μM $ZnCl_2$). Cells were lysed by sonication (1 minute 40 seconds in 10-sec pulses at 38% amplitude). Two 200 μL aliquots were withdrawn before clarifying the lysate by centrifugation (14000 rpm, 4° C., 30 minutes). All but the working aliquots of the crude and clarified lysates were flash-frozen with liquid nitrogen and stored at −80° C.

Single colonies of BL21 (DE3) cells transformed with plasmids potentially encoding the gene for active BoNT/A or BoNT/E were used to inoculate 1.0 mL cultures in OVERNIGHT EXPRESS autoinduction medium (Novagen); the BoNT/A cultures contained 100 μg/mL ampicillin, and the BoNT/E cultures contained 50 μg/mL kanamycin. Safe-Lock tubes equipped with membrane lids (2 mL; Eppendorf; Westbury, N.Y.) were used. Cultures were grown at 37° C., 1400 rpm, in a Thermomixer R (Eppendorf) until cloudy (about 3 hours for Type A and 7 hours for Type E), at which point the temperature was reduced, and the cultures incubated at 16° C. overnight. Cells were collected by centrifugation (15 minutes at 6,000×g, 4° C.) and stored at −80° C. until needed.

To identify cultures expressing active toxin, clarified cell lysates were prepared and tested in the GFP-SNAP25 assay. Cell pellets were defrosted on ice and each was lysed (20 minutes at 23° C., 300 rpm in the Thermomixer R) with 500 μL BUGBUSTER® Protein Extraction Reagent containing 25 U/mL benzonase nuclease and, for the Type A cell pellets, 1.2 KU/mL RLYSOZYME® and 1× Protease Inhibitor Cocktail III (all four reagents from Novagen). Lysates were clarified by centrifugation (20 minutes at 16000 rpm, 4° C.) and the supernatant solutions transferred to fresh microcentrifuge tubes. The assay reactions contained 10 μL clarified lysate and 10 μM (Type A) or 15 μM (Type E) GFP-SNAP25 substrate in a total volume of 50 μL Toxin Reaction Buffer (50 mM HEPES, pH 7.2; 10 μM $ZnCl_2$; 10 mM DTT; 0.1% (v/v) TWEEN-20® (polyoxyethylene (20) sorbitan monolaureate)). Two control reactions were assembled, each containing $dH_2O$ in place of the lysate and one containing rLC/E at a final concentration of 0.01 μg/mL. All reactions were assembled in triplicate and incubated at 37° C., for 40 minutes (Type A reactions) or 1 hour (Type E reactions). Reactions were quenched and processed as described below under general procedures for the GFP-SNAP25 assay.

EXAMPLE II

GFP-SNAP25 Fluorescence Release Assay

This example describes specific proteolysis of $GFP\text{-}SNAP25_{(134\text{-}206)}$ and quantification of proteolysis using a fluorescence release assay.

A. Overview of GFP-SNAP25 Fluorescence Release Assay

Figure 10G:
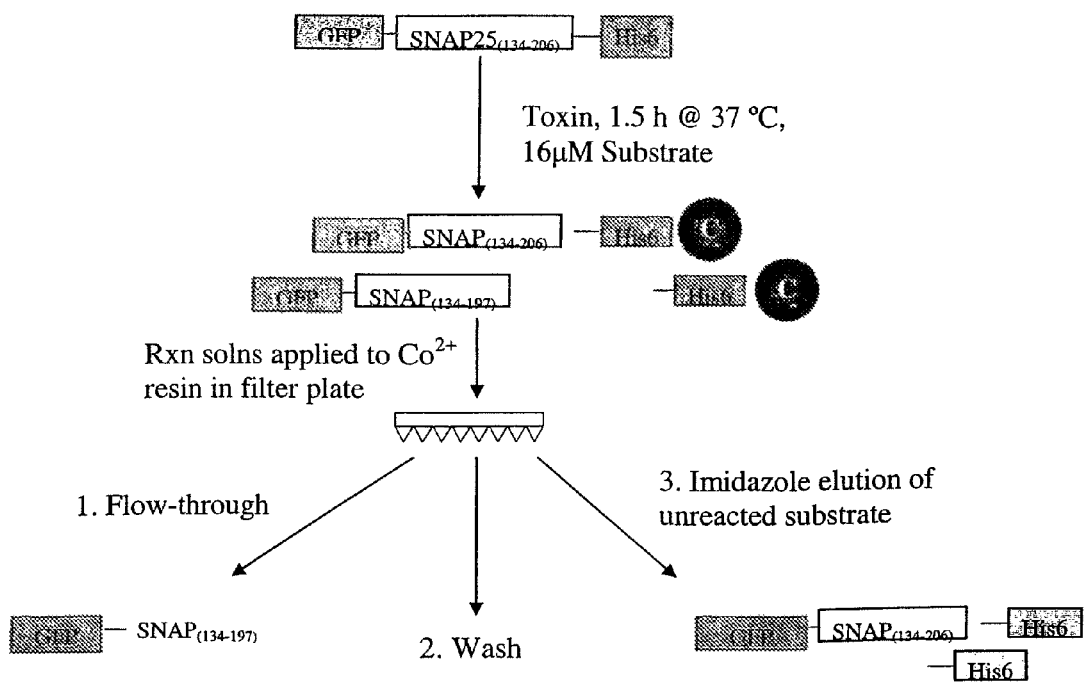

A summary of the GFP-SNAP25 fluorescence release assay is illustrated in FIG. 10G. Processing of the reaction mixture was dependent on the presence of a polyhistidine affinity tag which facilitates immobilized metal affinity chromatography (IMAC) separation of unreacted GFP-SNAP25 from endopeptidase generated GFP-SNAP25$_{(134-197)}$ cleavage product. As an overview, the treated substrate was processed as follows. First, a solution phase reaction was initiated by the addition of substrate to the appropriate light chain (zinc metalloprotease) or pre-reduced botulinum neurotoxin (serotype A, C, or E). Following incubation for the desired period of time under conditions described further below, the reaction was quenched by the addition of guanidinium chloride to a final concentration of 1-2 M. After termination of the reaction, unreacted substrate was separated from the endopeptidase-generated GFP-containing product (GFP-SNAP25$_{(134-197)}$) on IMAC resin. The reaction mixture was applied to a spin column or a 96-well filter plate containing Co$^{2+}$ resin in order to bind the polyhistidine-tagged species. The GFP-SNAP25$_{(134-197)}$ fragment that is freed from the polyhistidine affinity tag by proteolysis passes through the resin in the first "flow-through" fraction, while the unreacted substrate remains bound to the resin. Following collection of the flow-through fraction, the resin was washed with buffer to remove residual GFP-SNAP25$_{(134-197)}$ before unreacted GFP-SNAP25 substrate was eluted with imidazole. Collection of both the GFP-SNAP25$_{(134-197)}$ cleavage product as well as the GFP-SNAP25 substrate facilitates quantification of both product and unreacted substrate by fluorescence. The relative fluorescence of endopeptidase product (and, if desired, unreacted substrate) can then be plotted against the toxin concentration.

B. Solution Phase Clostridial Oroteolysis Reactions

Clostridial toxin protease reactions were performed as follows. Toxin, recombinant toxin, or recombinant LC/A or LC/E was diluted to twice the desired reaction concentration with 2× Toxin Reaction Buffer (100 mM HEPES, pH 7.2 or 7.4; 20 µM ZnCl$_2$; 20 mM DTT; 0.2% (v/v) BSA or TWEEN-20® (polyoxyethylene (20) sorbitan monolaureate)) and added to black v-bottom 96-well plates (Whatman; Clifton, N.J.) or microcentrifuge tubes in aliquots equal to one-half the final reaction volume. Each light chain or toxin sample was pre-incubated at 37° C. for 20 minutes. Prior to initiation of the reactions, GFP-SNAP25 substrate was diluted with sterile ddH$_2$O to twice the desired reaction concentration and warmed to 37° C. Reactions were initiated by addition of substrate to each well or tube in aliquots equal to one-half the final reaction volume. The final concentration of substrate in standard reactions was 10-16 µM. Reaction vessels were sealed, protected from light, and incubated at 37° C. The incubation period was generally 90 minutes, except that time course reactions were frequently run for longer periods; reactions were run in triplicate. At the end of the incubation period or at specified time points, reactions or reaction aliquots were quenched by the addition of 8 M guanidine hydrochloride to a final concentration of 1-2 M and subsequently processed as described below.

C. Separation of Fluorescent Cleavage Product

Samples were processed as described below with all steps either performed manually with a UniVac® vacuum manifold (Whatman) for elution at −15 in Hg or, with the exception of the addition of resin to the filter plate, were performed on a Biomek-FX liquid handling system (Beckman/Coulter; Fullerton, Calif.). The required number of wells in a 96-well filter plate (400 µL or 800 µL wells, 0.45 µm filter, long drip; Innovative Microplate; Chicopee, Mass.) were loaded with 75 µL of Talon™ Superflow Co$^{2+}$ affinity resin (Becton Dickinson Biosciences). Resin storage buffer was removed by vacuum, and the resin conditioned by rinsing with 4 column volumes ddH$_2$O and 4 column volumes Assay Rinse Buffer (50 mM HEPES, pH 7.4). The last aliquot of Assay Rinse Buffer was eluted from the resin immediately prior to use.

Following quenching with guanidine hydrochloride, reaction solutions were transferred to filter plate wells containing conditioned Co$^{2+}$ resin, where they were incubated at room temperature for 15 minutes. The reaction solutions were then eluted, collected in a black, flat-bottom 96-well plate (BD Falcon), passed over the resin beds twice more and collected after the final pass. Each resin bed was then rinsed with 2×135 µL Assay Rinse Buffer that was eluted into the plate containing the eluant reaction solution, which contains the GFP product.

In some cases, unreacted substrate was collected after washing the resin beds with 3×250 µL Assay Rinse Buffer. Unreacted substrate was then eluted from the resin beds with 260 µL Assay Elution Buffer 500 (50 mM HEPES, pH 7.4; 500 mM imidazole) and collected in a black, flat-bottom 96-well plate (BD Falcon).

The fluorescence of the reaction flow-through and imidazole eluant solutions was quantified with a SpectraMax Gemini XS spectrophotometer (Molecular Devices; $\lambda_{Ex}$ 474 nm; $\lambda_{Em}$ 509 nm; 495 nm cutoff filter).

D. Results of GFP-SNAP25 Fluorescence Release Assays

Results of the GFP-SNAP25 fluorescence release assays are summarized below. The ability to easily measure unreacted starting material provided an internal control for the reactions and served to demonstrate that substrate was completely converted to product (see FIG. 11C as an example). Proteolytic activity of recombinant light chain type A (rLC/A) and botulinum neurotoxin serotypes A and E was detected at picomolar concentrations. The enzymatic activity of BoNT/C complex was also detected at low nanomolar concentrations, consistent with literature reports for serotype C requiring the presence of membranes for activity and having poor in vitro activity in general (Vaidyanathan et al., *J. Neurochem* 72:327-337 (1999); Foran et al., *Biochemistry* 35:2630-2636 (1996); Blasi et al., *EMBO J.* 12:4821-4828 (1993)).

Figure 11A:
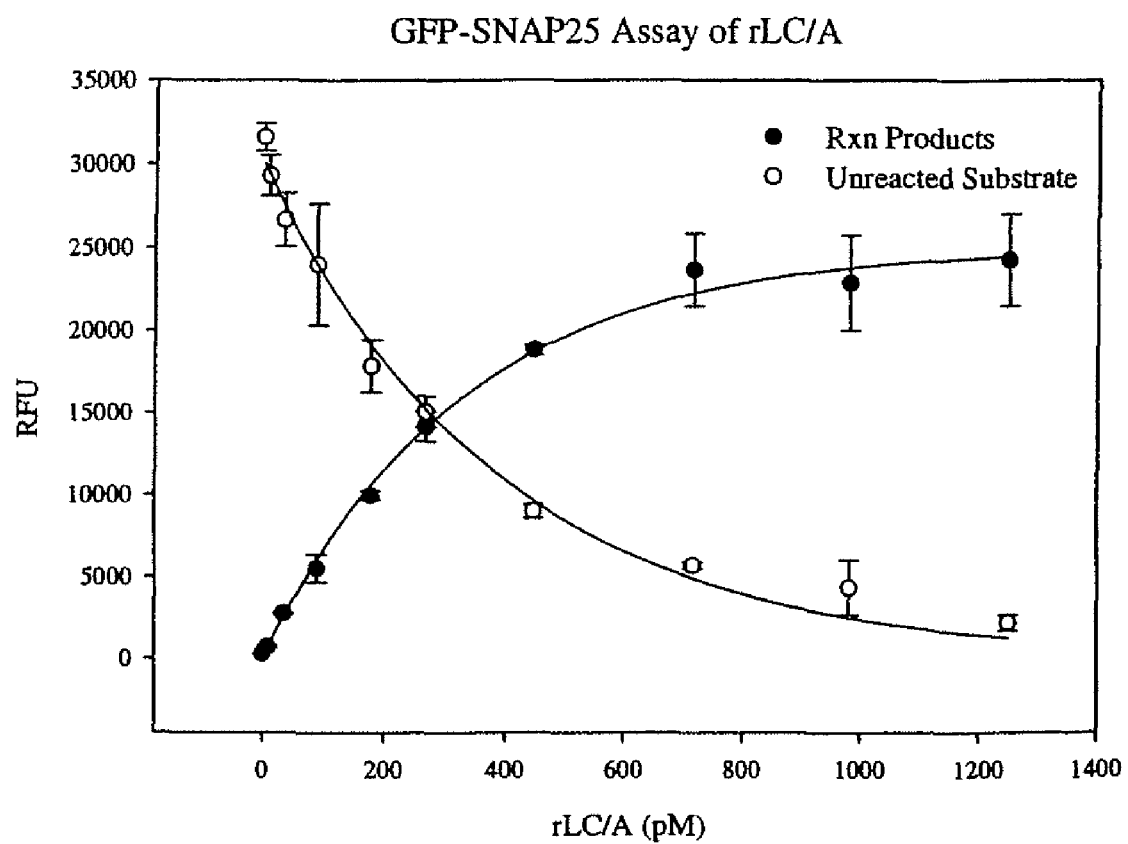
FIG. 11 shows endopeptidase activity of recombinant light chain, native and bulk A toxin. (A) Endopeptidase activity of recombinant type A light chain. (B) Endopeptidase activity of native BoNT/A dichain toxin. (C) Endopeptidase activity of bulk A toxin.

Recombinant type A light chain (rLC/A) activity. The activity of rLC/A was efficiently measured with the GFP-SNAP25 fluorescence release assay as shown in FIG. 11A. For reactions in which the substrate concentration was 16 µM, rLC/A at a concentration range of 9 to 1,250 pM yielded reaction products with relative fluorescence units (RFUs) from 730 to over 24,000. As further demonstrated in FIG. 11A, a significant signal was measured at a rLC/A concentration of 36 pM.

150 kDa BoNT/A (pure A) toxin activity. The activity of native BoNT/A toxin was also efficiently measured with the GFP-SNAP25 fluorescence release assay (see FIG. 11B). For reactions in which the substrate concentration was 16 µM, native pure BoNT/A at a concentration range of 17 to 1,000 pM yielded reaction products with relative fluorescence units from 4,600 to almost 24,000. FIG. 11B further shows that a significant signal was measured at a pure BoNT/A concentration of 17 pM.

900 kDa BoNT/A (bulk) toxin activity. The BoNT/A complex was very efficient at cleaving GFP-SNAP25 substrate, with 6 pM of bulk BoNT/A toxin complex yielding a signal that was 19 fold above background (see FIG. 11C). For reactions in which the substrate concentration was 16 µM, BoNT/A at a concentration range of 3 to 89 pM yielded reaction products with (relative fluorescence units) from 2,600 to over 60,000 (FIG. 11C).

146 kDa BoNT/E (pure E) toxin activity. Unlike BoNT/A, single chain (SC) BoNT/E is not nicked by Clostridia to form the activated dichain form. Activation of native single chain BoNT/E toxin can be accomplished by exogenous treatment of toxin with trypsin. As shown in FIGS. 12A and 12B, respectively, native single chain and dichain BoNT/E both cleaved the GFP-SNAP25 substrate. Trypsin nicking of single chain BoNT/E to yield the dichain form substantially increased the proteolytic activity of serotype E.

As shown in FIG. 12A, for reactions in which the substrate concentration was 16 µM, native single-chain BoNT/E at a concentration range of 2 to 21 nM yielded reaction products with relative fluorescence units from approximately 3,800 to 22,000. As shown in FIG. 12B, the specific activity of native dichain BoNT/E under the same reaction conditions was much greater. At a concentration range of 17 to 1,546 µM, dichain BoNT/E yielded reaction products with relative fluorescence units from approximately 1,200 to 19,000.

BoNT/C complex activity. As discussed above, BoNT/C is known to cleave both syntaxin and SNAP-25 in vivo, with the BoNT/C cleavage site within the GFP-SNAP substrate residing at Arg198-Ala199 of SNAP25. GFP-SNAP substrate was assayed as a substrate for type C by incubation with BoNT/C complex. As shown in FIG. 12C, GFP-SNAP can detect BoNT/C activity; however, it is not detected as readily as BoNT/A or /E activity. For reactions in which the substrate concentration was 16 µM, native BoNT/C at a concentration range of 4 to 60 nM yielded reaction products with relative fluorescence units from approximately 3,800 to 22,000, consistent with literature reports of poor in vitro activity for serotype C and reports that BoNT/C may require the presence of membranes for efficient enzymatic activity (Vaidyanathan et al., supra, 1999; Foran et al., supra, 1996; Blasi et al., supra, 1993).

EXAMPLE III

Variation of Assay Conditions with Recombinant GFP-SNAP-25 Substrate

This example describes variation and optimization of the GFP-SNAP25 fluorescence release assay.

A. Assay Optimization: BSA vs. Tween-20

Initially, GFP-SNAP assays were conducted in Toxin Reaction Buffer containing bovine serum albumin (BSA) as a protein carrier/stabilizer (50 mM Hepes, pH 7.4, 10 µM $ZnCl_2$, 10 mM DTT, and 0.1 mg/mL BSA). The reaction buffers for some botulinum neurotoxin assays contain the detergent TWEEN-20® (polyoxyethylene (20) sorbitan monolaureate), rather than BSA. An investigation comparing the effect of these protein stabilizers on BoNT reactions revealed that serotypes A, C, and E all have significantly higher activity in the presence of 0.1% (v/v) TWEEN-20® (polyoxyethylene (20) sorbitan monolaureate) as compared to BSA. These results indicate that the use of TWEEN-20® (polyoxyethylene (20) sorbitan monolaureate) in place of BSA results in higher activity for BoNT/A, /C and /E.

B. Assay Optimization: pH

The pH of the protease reaction buffers was varied within the range of 7.0-8.2. Bulk A toxin was most active at pH 7.2 while type E dichain was most active at pH 7.0. pH values below 7 were not assayed since fluorescence of the GFP fusion protein substrate is quenched under acidic conditions (Ekong et al., Dev. Animal Vet. Sci. 27:1039-1044 (1997)). Although the activity of bulk A toxin is known to be dependent on the release of toxin and light chain from the complex, a process which is most efficient at elevated pH (Hallis et al., J. Clin. Microbiol. 34:1934-1938 (1996)), the results obtained with the GFP-SNAP25 substrate agree with those indicating that the optimum pH for rLC/A expressed from a synthetic gene is pH 7.2 and that activity drops fairly quickly on either side of this optimum. In contrast, the pH preference of type E toxin was not as pronounced as that of Bulk A; type E activity was not completely eliminated even at pH 8.2.

pH profiles of bulk A toxin and pure E dichain toxin were determined as follows. The general procedures for the GFP-SNAP25 assay described above were followed to determine the optimal toxin reaction pH, except as noted. Seven 2× Toxin Reaction Buffer solutions were prepared at pH 7.00, 7.20, 7.41, 7.60, 7.80, 8.01, and 8.24. These buffers were used to prepare the toxin dilutions. The final reaction concentrations of the toxins were 89 µM native BoNT/A complex and 203 µM native pure E dichain. Reactions were quenched after a 90 minute incubation.

C. Assay Optimization: Dithiothreitol Dependence

Using bulk A toxin, it was observed that the lack of a pre-incubation period with 10 mM dithiothreitol simply resulted in a delay in the production of cleavage product. In contrast, the absence of dithiothreitol resulted in essentially complete loss of activity.

GFP-SNAP25 time-course assays of bulk BoNT/A toxin for dithiothreitol (DTT) dependence were performed as follows. The general procedures for the GFP-SNAP25 assay described above were followed, except as noted below, for testing the dependence of bulk A activity upon DTT and the requirement for a pre-incubation period. An initial dilution of bulk A toxin was made in 2× Toxin Reaction Buffer without DTT. Aliquots were removed from this solution to prepare additional dilutions, one into Toxin Reaction Buffer containing DTT and the other into the same buffer without DTT. Buffer solutions were pre-warmed to 30° C. Four types of reactions plus one substrate-only control, each in triplicate, were assembled. Two sets of reactions contained DTT and two did not, with just one set of each type pre-incubated for 20 minutes at 30° C. prior to initiation of the reactions. The time elapsed from transfer of the bulk A from the stock solution to the initiation of the "no pre-incubation" reactions was 1.5 minutes. The substrate-only control reactions did not contain DTT but were pre-incubated. The final reaction volume was 400 µL and contained 44 pM bulk A and 16 µM GFP-SNAP25 substrate. Aliquots of 50 µL were removed from each reaction and quenched with 20 µL guanidine HCl at 15, 30, 45, 60, and 90 minute time points.

D. Specificity of Toxin Cleavage Demonstrated Using Mutant GFP-SNAP25 Substrate with Altered Scissile Bonds As discussed above, the fusion protein substrate used in the GFP-SNAP25 assay contains residues 134-206 of SNAP-25. BoNT/A cleaves SNAP-25 between residues Ala 197 and Arg 198, while BoNT/C cleaves the neighboring peptide bond between residues Arg 198 and Ala 199. The conversion of Arg 198 to alanine has been shown to eliminate detectable hydrolysis by BoNT/A in certain assays (Schmidt et al., FEBS Lett 435:61-64 (1998)) and likely also eliminates proteolysis by BoNT/C. The Arg 198 to Ala change was therefore introduced into the GFP-SNAP25 substrate by site-directed mutagenesis to create a control fusion protein denoted GFP-SNAP25(R198A).

The cleavage site for BoNT/E resides between residues Arg 180 and Ile 181; however, no single-residue mutation has been shown to eliminate hydrolysis. An Arg 180 to aspartate mutation was selected for a possible control substrate, due to the charge reversal as well as steric differences introduced by the change. The GFP-SNAP substrate analogue containing this mutation is denoted GFP-SNAP(R180D).

Figure 13:
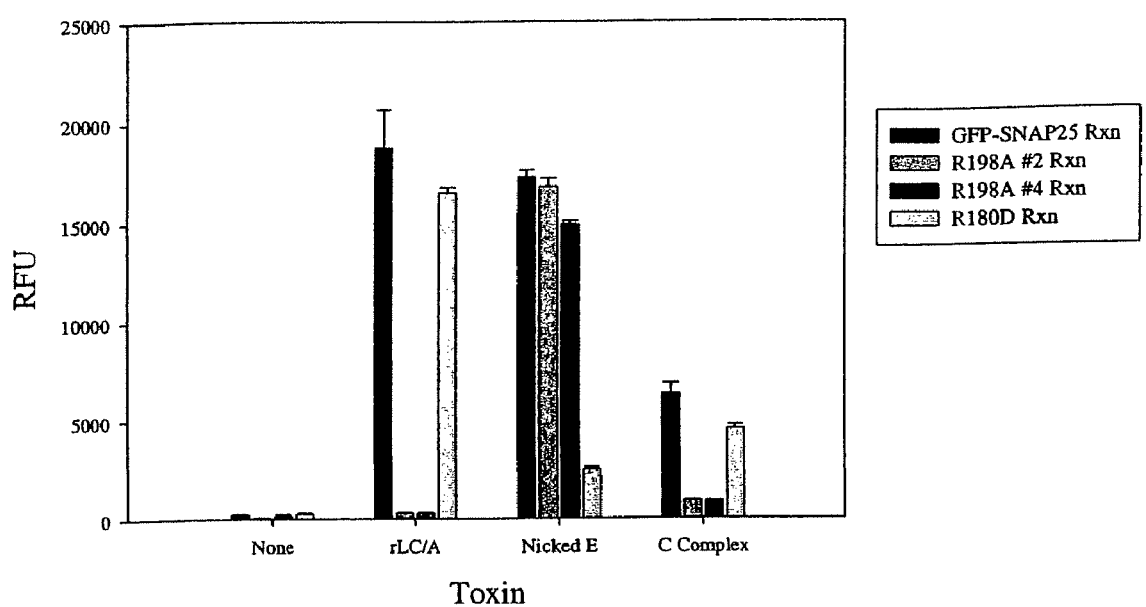

Fusion protein substrate mutants R198A#2, R198A#4 and R180D were expressed and purified essentially as described above for the standard GFP-SNAP25$_{(134-206)}$ substrate. Mutant substrates were then tested under GFP-SNAP25 assay conditions with relatively high concentrations of toxins (4.5 nM rLC/A, 6.8 nM native pure E dichain, and 60 nM BoNT/C complex). As demonstrated in FIG. 13, despite high toxin concentrations, there was virtually no cleavage of the R198A mutants by rLC/A; furthermore, cleavage by the BoNT/C complex was reduced to approximately 14% of the level seen with the GFP-SNAP25 substrate, which translates to ~4× the background signal. Proteolysis by BoNT/E of the R180D mutant was significantly reduced to approximately 15% of the standard substrate proteolysis, although the signal remained greater than 11× the background signal in spite of the steric differences and reversal of charge introduced into the substrate at the site of the scissile bond.

Analysis of R180D proteolysis by type E toxin was repeated to confirm that the result was reproducible and to verify cleavage at the Asp180/Ile181 bond. SDS-PAGE analysis of the reaction products confirmed that the R180D mutant was partially cleaved by Type E, and that the larger fragment produced has the same apparent molecular weight as that produced by proteolysis of the standard GFP-SNAP25 substrate.

In addition to the toxin proteolysis experiments, trypsin digestion of the substrates was performed. The GFP portion of the substrates was expected to remain intact as GFP has been shown to be resistant to proteases other than pronase (U.S. Pat. No. 5,965,699). As expected, essentially all of the GFP was released by trypsin digestion.

Trypsin digestion of GFP-SNAP25 substrates was performed as follows. Spin columns and filters (35 μm pore size; MoBiTec; Goettingen, Germany) were packed with 5 μL of agarose bead-bound trypsin (24.1 U/mL of packed gel; Sigma). Fusion protein substrates (GFP-SNAP25 and mutants R198A#4 and R180D) were diluted to a concentration of 30 μg/15 μL in Digest Buffer (20 mM HEPES, pH 7.4; 300 mM NaCl). Reactions were run in duplicate and initiated by addition of 15 μL of the substrate solution to a spin column containing the trypsin gel. After incubation for one hour at 30° C., reaction products were eluted by centrifugation and collected in 1.7 mL microcentrifuge tubes. Each resin bed was rinsed with 40 μL Digest Buffer, which was eluted and collected in the same tube as the reaction solution. Samples were subsequently processed according to the filter-plate processing methods described above.

E. Cleavage of Fusion Protein Substrates by Endogenous Proteases in Crude Lysates Substrate mutants R180D and R198A serve as substrate controls to distinguish toxin activity in a cell lysate from the proteolytic activity of endogenous proteases. Essentially, any non-toxin proteolysis in a lysate would be reflected in the signal from control substrates, while the GFP-SNAP25 signal would reflect the combined activity of toxin and endogenous proteases.

Lysates from two types of E. coli cells were assayed. The first was a lysate from BL21-CODONPLUS® (DE3)-RIL, a protease deficient cell line transformed to express rLC/A and the fusion protein substrates. Reactions were assembled to mimic the GFP-SNAP25 assay conditions, except that either 5 μL or 20 μL of clarified lysate was included in lieu of toxin.

Figure 14A:
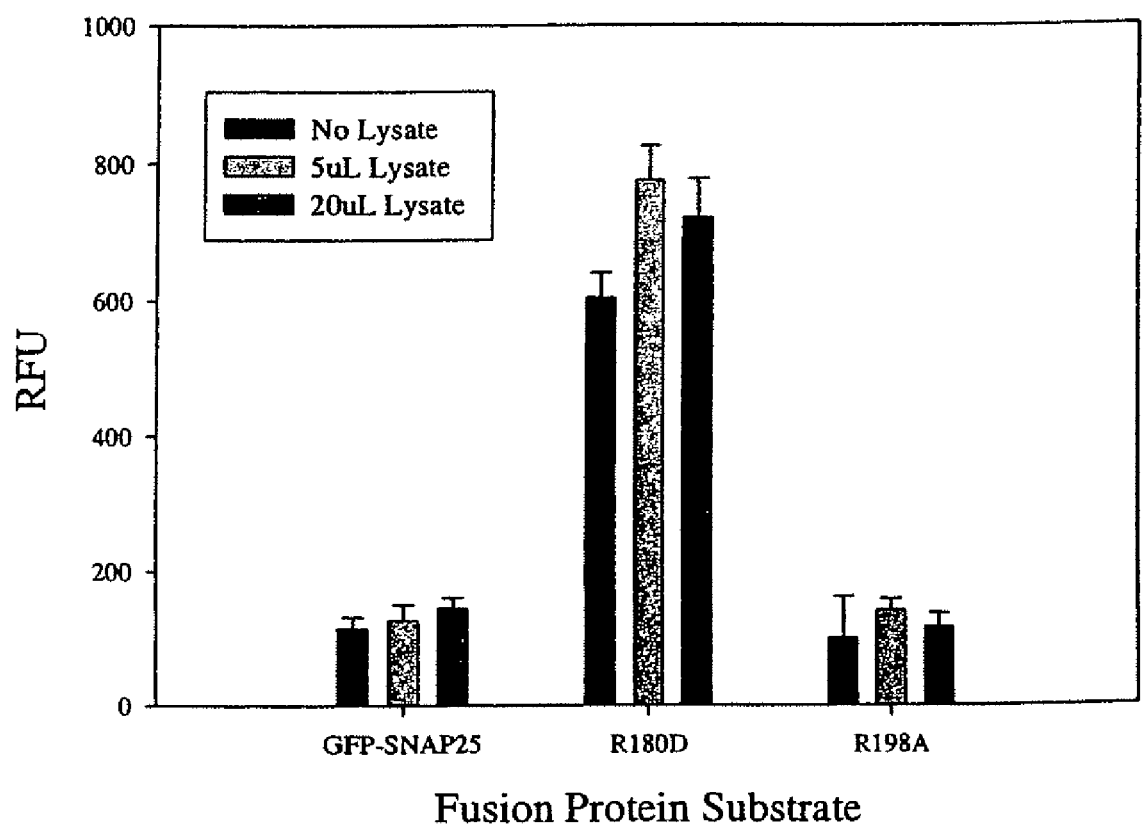
Figure 14B:
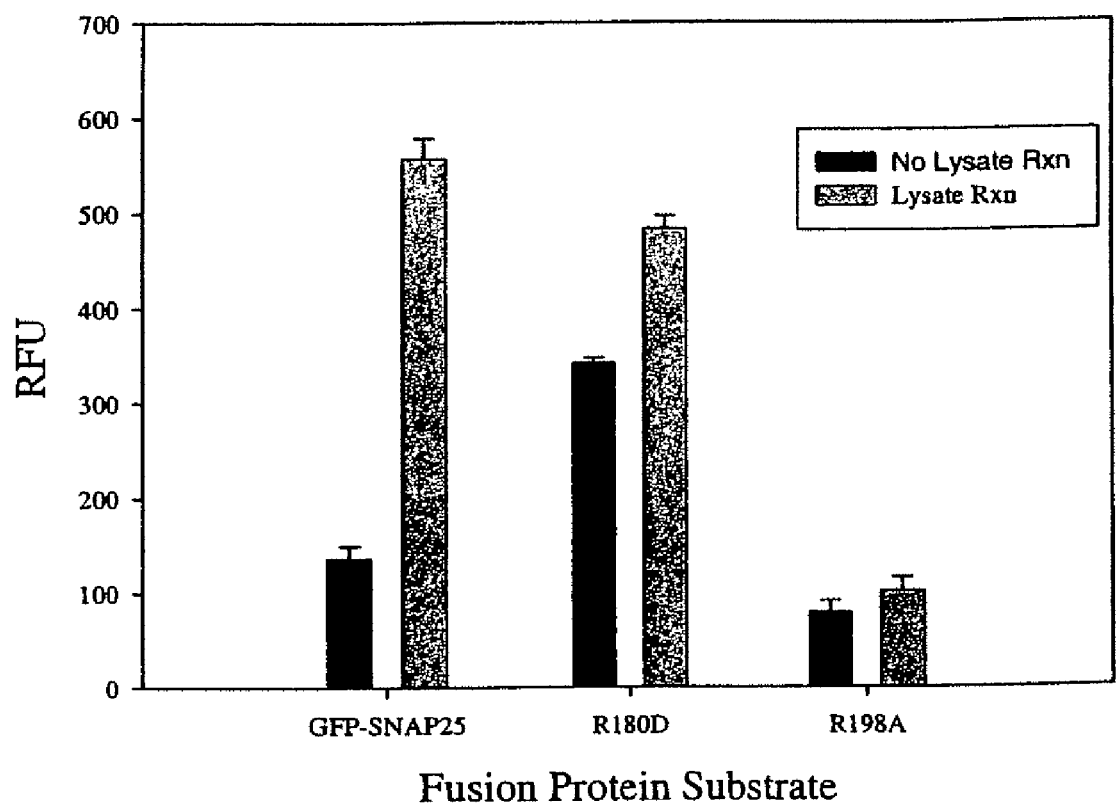

As shown in FIG. 14A, there was insignificant proteolysis of any of the substrates. Only the signals for the reactions containing R180D exceed the background signals typically seen in the GFP-SNAP25 assay. Cell lysates from TOP10® cells, which are not protease deficient, were also assayed. In these experiments, 20 μL of clarified lysate was included, and once again the level of hydrolysis was negligible (FIG. 14B). These results indicate that the proteolysis of GFP-SNAP25 substrates is specific to clostridial toxins and is not due to other proteases endogenous to cell lystates.

Proteolysis of fusion protein substrates in crude, clarified cell lysates was performed as follows. Reactions containing 5 μL or 20 μL of crude, clarified lysate from E. coli BL21-CODONPLUA® (DE3)-RIL cells (Stratagene) or E. coli TOP10® cells (Invitrogen) were assembled and initiated by addition of GFP substrate (GFP-SNAP25, R198A, or R180D) to a final concentration of 16 μM. Substrate dilutions were prepared with 2× Toxin Reaction Buffer (100 mM HEPES, pH 7.4; 20 μM ZnCl$_2$; 20 mM DTT; 0.2% (v/v) TWEEN-20® (polyoxyethylene (20) sorbitan monolaureate)), and an additional 5 μL of the 2× Toxin Reaction Buffer was included in each reaction so that the final concentration would be approximately 1× Toxin Reaction Buffer. In all cases final reaction volumes were 50 μL, and reactions were run in triplicate. For control reactions, sterile ddH$_2$O was included in place of cell lysate. Reactions were incubated for one hour at 37° C., quenched with 15 μL 8M guanidine hydrochloride, and processed according to the filter-plate processing method described above.

F. Kinetic Data for rLC/A

Several reaction and processing conditions were explored in order to determine whether the GFP-SNAP25 fluorescence release assay was sensitive over a substrate concentration range flanking the KM, and whether the required substrate concentrations can be accommodated under the standard processing conditions. Data were obtained by running a series of time course assays at a single toxin concentration over a range of substrate concentrations. The reaction conditions and processing details such as the length of the reactions and the resin volumes were varied among assays. For these initial tests, all the reactions contained 178 pM rLC/A and the substrate concentration was varied from 2.5-80 μM.

Figure 15:
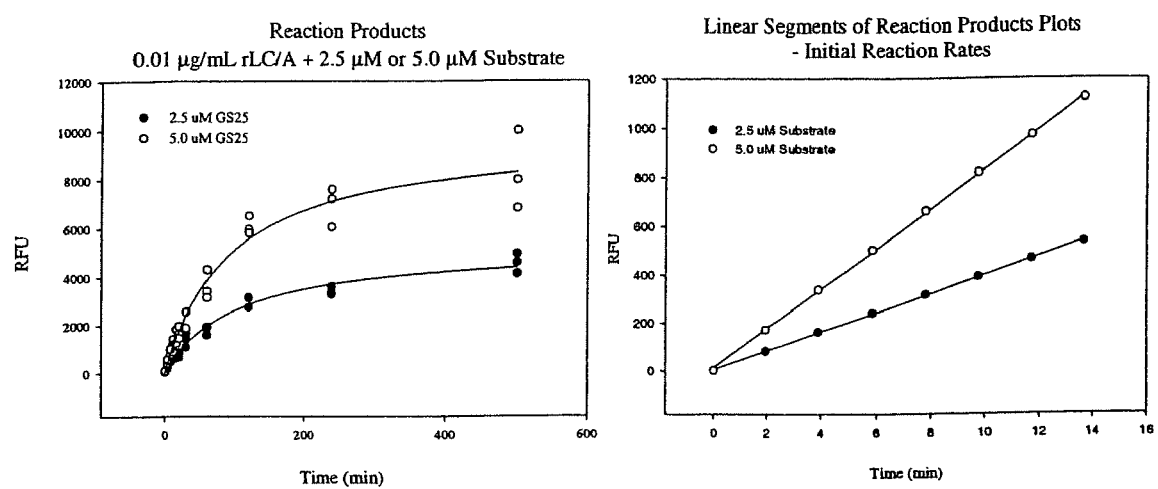
Figure 16:
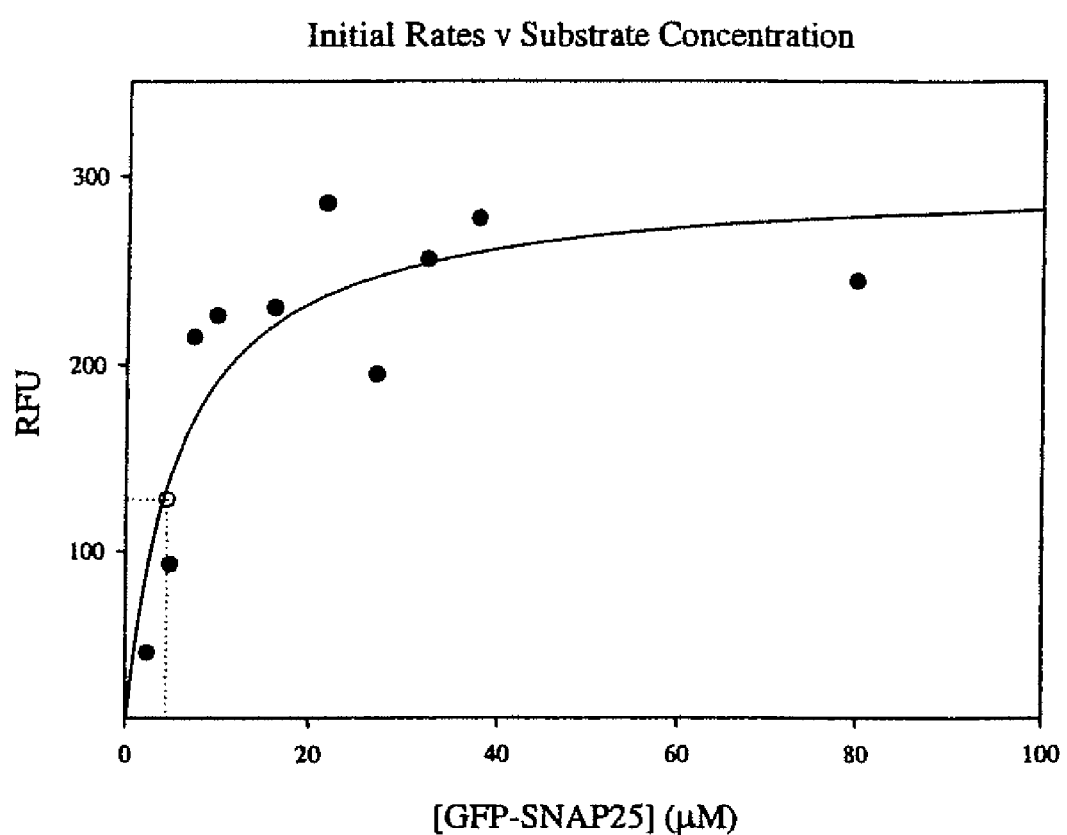

The process of kinetic analysis included non-linear fitting of curves to plots of the data, determination of initial substrate velocities from these curves, and lastly plotting the initial velocities against substrate concentration to estimate of $v_{max}$ and $K_m$. The initial plot provides a preliminary $K_m$ value of 4.6 μM at this toxin concentration (FIGS. 15 and 16). Alternatively, the assay can be run at many times this substrate concentration.

Published Type A toxin kinetic constants, most of which were determined with HPLC-based assays, are shown in Table 6.

Time-course assays of rLC/A for kinetic analyses were performed using a final toxin concentration of 0.01 μg/mL (0.18 nM), while the substrate concentration was varied from 2.5-80 μM. Three reactions plus one to three substrate-only controls were assembled at each substrate concentration as described under general procedures for the GFP-SNAP25 Assay, and the reactions were incubated for two to seven hours. Aliquots of 50 μL (30 μL for the 80 μM substrate reactions) were withdrawn over the course of the reactions, beginning at the 4 minute point, and quenched with 20 μL 8M guanidine hydrochloride. The quenched samples were processed as described above under general procedures for the GFP-SNAP25 assay.

TABLE 6

Published Kinetic Constants

| Enzyme | Substrate | $K_m$ (µM) | $k_{cat}$ (s-1) | Reference |
|---|---|---|---|---|
| BoNT/A | rSNAP25$_{(1-206)}$ | 79 ± 8 | 0.009 | Schmidt et al., J Prot. Chem 16: 19-26 (1997) |
| BoNT/A | rSNAP25$_{(137-206)}$ | 353 ± 17 | 0.02 | Schmidt et al., supra, 1997 |
| BoNT/A | Various 17-mer peptides | 580-5000 | 1.8-56 | Schmidt et al., FEBS Lett. 435: 61-64, (1998) |
| BoNT/A | 17-mer peptide | 5000 ± 500 | 4.7 ± 0.5 | U.S. Pat. No. 5,965,699 |
| rLC/A | 17-mer peptide | 1100 ± 100 | 23 ± 1 | U.S. Pat. No. 5,965,699 |
| rLC/A | FIA | 96 ± 10 | 7.2 ± 0.4 | U.S. Pat. No. 5,965,699 |

G. GFP-SNAP25 Fluorescence Release Assay of Single Vials of Botox®

Figure 17:
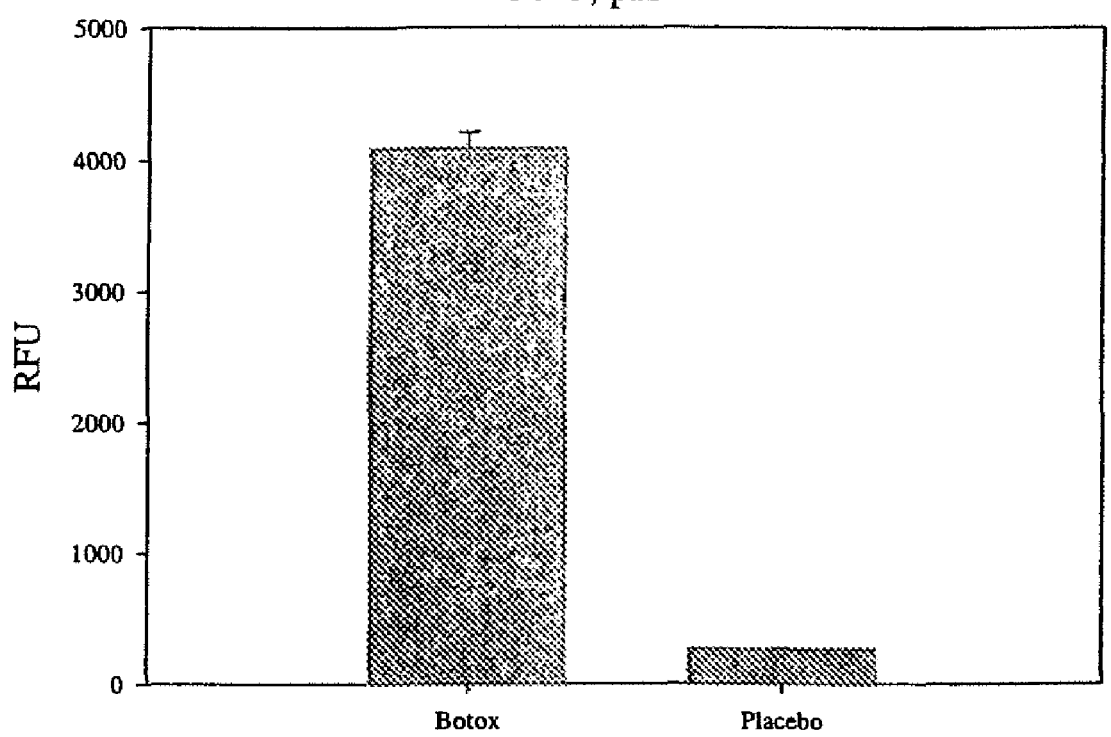

From the results described above, the GFP-SNAP assay is sensitive enough to assay the contents of single vials of BOTOX® (botulinum toxin serotype A). However, BOTOX® (botulinum toxin serotype A) did not significantly cleave GFP-SNAP25 substrate under the standard conditions described above. Notably, a salt content (~0.88 mg NaCl/vial) as well as a large amount of HSA (~0.5 mg/vial) are present in BOTOX® (botulinum toxin serotype A). A dialysis step to remove the salt resulted in increased background fluorescence and did not produce significant proteolysis. To remove the HSA, which might interfere with proteolysis or binding of His-tagged species to the purification resin, the BOTOX® (botulinum toxin serotype A) vial contents were dialyzed using a Teflon-coated dialysis unit with 100,000 MWCO membrane. The contents of a vial were resuspended in 100 µL dH$_2$O, and, following dialysis, approximately ⅕ of the toxin from a vial was included in each of the final reactions, assuming that 100% of the toxin was transferred from the vial and recovered following dialysis. The contents of two vials were assayed in a total of six reactions, and a placebo control vial was also assayed in triplicate. As shown in FIG. 17, the BOTOX® (botulinum toxin serotype A) signal was readily detectable at 15-fold above background. These results indicate that the high NaCl and HSA content of formulated BOTOX® (botulinum toxin serotype A) product can interfere with the GFP-SNAP25 fluorescence release assay. These results further indicate that, following removal of NaCl and human serum albumin through dialysis or another method, BOTOX® (botulinum toxin serotype A) or other formulated toxin product can be assayed using the GFP-SNAP25 fluorescence release assay disclosed herein.

GFP-SNAP25 Assays of BOTOX® (botulinum toxin serotype A) were performed as follows. The contents of two vials of BOTOX® (botulinum toxin serotype A)® were dissolved, each in 100 µL sterile dH$_2$O, and transferred to the same dialysis unit (Fast Spin Dializer, Harvard Apparatus, 100,000 MWCO). The contents of a single placebo vial were also dissolved in 100 µL sterile dH$_2$O and transferred to a dialysis unit of the same type but smaller volume. The toxin solution was dialyzed against 2×1 L BOTOX® (botulinum toxin serotype A) Dialysis Buffer (50 mM HEPES, pH 7.2; 10 µM ZnCl$_2$), and the placebo solution was dialyzed against 2×500 mL BOTOX® (botulinum toxin serotype A) Dialysis Buffer, with a total dialysis time of one hour at room temperature. Following dialysis, 140 µL of the BOTOX® (botulinum toxin serotype A) solution was combined with 35 µL BOTOX® (botulinum toxin serotype A) Reaction Buffer (50 mM HEPES, pH 7.2; 10 µM ZnCl$_2$; 0.17% (v/v) TWEEN-20® (polyoxyethylene (20) sorbitan monolaureate); 16 mM DTT) pre-warmed to 30° C.; 80 µL of the placebo solution was combined with 20 µL of the BOTOX® (botulinum toxin serotype A) Reaction Buffer. Both solutions were preincubated at 30° C. for 20 minutes. The GFP-SNAP25 dilution (to 40 µM) was prepared with the BOTOX® (botulinum toxin serotype A) Reaction Buffer. Reactions were initiated by combining 25 µL of either the BOTOX® (botulinum toxin serotype A) or placebo solution with 25 µL of the substrate solution. Six BOTOX® (botulinum toxin serotype A) reactions and three placebo control reactions were initiated and incubated at 30° C. for 3 hours, 5 minutes. Reactions were quenched with 20 µL 8 M guanidine hydrochloride and processed as described in the above general procedures for the GFP-SNAP25 assay.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the following claims.

We claim:

1. A method of determining Botulinum toxin serotype C1 protease activity, comprising the steps of:
   (a) treating with a sample, in solution phase under conditions suitable for Botulinum toxin serotype C1 protease activity, a tagged toxin substrate comprising
      (i) a fluorescent protein;
      (ii) a first partner of an affinity couple; and
      (iii) a Botulinum toxin serotype C1 recognition sequence comprising a cleavage site, where the cleavage site intervenes between said fluorescent protein and said first partner of the affinity couple, such that a fluorescent cleavage product is generated when Botulinum toxin serotype C1 is present in said sample;
   (b) contacting said treated sample with a second partner of the affinity couple, thereby forming stable complexes comprising said first and second partners of said affinity couple; and
   (c) assaying the presence or amount of said fluorescent cleavage product in said treated sample, thereby determining Botulinum toxin serotype C1 protease activity.

2. The method of claim 1, wherein said fluorescent protein is selected from the group green fluorescent protein (GFP), blue fluorescent protein (BFP), cyan fluorescent protein (CFP), yellow fluorescent protein (YFP) and red fluorescent protein (RFP).

3. The method of claim 2, wherein said fluorescent protein is GFP.

4. The method of claim 1, 2 or 3, wherein said first partner of the affinity couple is selected from the group histidine tag, glutathione-S-transferase, maltose-binding protein, a biotinylation sequence, streptavidin, S peptide, S protein, FLAG, hemagluttinin (HA), c myc and AU1.

5. The method of claim 1, wherein said first partner of the affinity couple is a histidine tag.

6. The method of claim 1, wherein said Botulinum toxin serotype C1 recognition sequence comprises at least six consecutive residues of syntaxin, said six consecutive residues comprising Lys-Ala.

7. The method of claim 6, wherein said Botulinum toxin serotype C1 recognition sequence comprises SEQ ID NO: 5.

8. The method of claim 1, wherein said Botulinum toxin serotype C1 recognition sequence comprises at least six consecutive residues of SNAP-25, said six consecutive residues comprising Arg-Ala.

9. The method of claim 8, wherein said Botulinum toxin serotype C1 recognition sequence comprises SEQ ID NO: 1.

10. The method of claim 8, wherein said Botulinum toxin serotype A recognition sequence comprises SEQ ID NO: 27.

11. The method of claim 8, wherein said Botulinum toxin serotype A recognition sequence comprises SEQ ID NO: 28, SEQ ID NO: 29, SEQ ID NO: 30, SEQ ID NO: 31, SEQ ID NO: 32.

12. The method of claim 8, wherein said Botulinum toxin serotype A recognition sequence comprises residues 134 to 206 of SEQ ID NO: 2, residues 137 to 206 of SEQ ID NO: 2.

13. The method of claim 1, wherein said substrate is cleaved with an activity of at least 1 nanomole/minute/milligram toxin.

14. The method of claim 1, wherein said substrate is cleaved with an activity of at least 100 nanomoles/minute/milligram toxin.

15. The method of claim 1, wherein said substrate is cleaved with an activity of at least 1000 nanomoles/minute/milligram toxin.

16. The method of claim 1, wherein said second partner of the affinity couple is immobilized.

17. The method of claim 1, wherein said second partner of the affinity couple comprises cobalt (Co2+).

18. The method of claim 1, wherein said second partner of the affinity couple comprises nickel (Ni2+).

19. The method of claim 1, further comprising separating said fluorescent cleavage product from said stable complexes prior to step (c).

20. The method of claim 19, wherein said separating comprises applying said treated sample to a column, wherein said second partner of the affinity couple is immobilized on said column.

21. The method of claim 19, wherein said separating comprises applying said treated sample to a filter plate, wherein said second partner of the affinity couple is immobilized on said filter plate.

22. The method of claim 1, further comprising step (d) assaying the amount of uncleaved tagged toxin substrate in said treated sample.

23. The method of claim 1, wherein said sample is isolated Botulinum toxin serotype C1.

24. The method of claim 1, wherein said sample is isolated Botulinum toxin serotype C1 light chain.

25. The method of claim 1, wherein said formulated product is a formulated Botulinum toxin serotype C1 product.

26. The method of claim 1, wherein said sample is a whole or partially purified cellular extract containing recombinantly expressed Botulinum toxin serotype C1.

* * * * *

UNITED STATES PATENT AND TRADEMARK OFFICE
CERTIFICATE OF CORRECTION

PATENT NO.      : 7,838,260 B2
APPLICATION NO. : 12/019120
DATED           : November 23, 2010
INVENTOR(S)     : Lance E. Steward et al.

It is certified that error appears in the above-identified patent and that said Letters Patent is hereby corrected as shown below:

On page 2, in column 1, under "Other Publications", line 16, delete "protein ,"" and insert -- protein," --, therefor.

On page 2, in column 2, under "Other Publications", line 8, delete "synaptosomeassociated" and insert -- synaptosome associated --, therefor.

On page 3, in column 2, under "Other Publications", line 53, delete ""Fluorigenic" and insert -- "Fluorogenic --, therefor.

On page 3, in column 2, under "Other Publications", line 71, delete "fluorimetric" and insert -- fluorometric --, therefor.

On page 4, in column 1, under "Other Publications", line 13, delete "gluthation" and insert -- glutathione --, therefor.

In column 1, line 33, delete "laringeal" and insert -- laryngeal --, therefor.

In column 4, line 22, delete "(Botulinum toxin serotype A)" and insert -- (botulinum toxin serotype A). --, therefor.

In column 9, line 17, delete "(Neimann," and insert -- (Niemann, --, therefor.

In column 9, line 39, delete "neutrotoxin" and insert -- neurotoxin --, therefor.

In column 12, line 26, delete "Val 63Ala" and insert -- Val163ALa --, therefor.

In column 12, line 64, delete "Entacmeae" and insert -- Entacmaea --, therefor.

In column 13, line 52-53, delete "β-glucouronidase" and insert -- β-glucuronidase --, therefor.

Signed and Sealed this
Tenth Day of May, 2011

David J. Kappos
*Director of the United States Patent and Trademark Office*

CERTIFICATE OF CORRECTION (continued)

U.S. Pat. No. 7,838,260 B2

In column 14, line 11, delete "β-glucouronidase" and insert -- β-glucuronidase --, therefor.

In column 14, line 30, delete "Entacmeae" and insert -- Entacmaea --, therefor.

In column 19, line 2, delete "invention" and insert -- invention. --, therefor.

In column 23, line 6, delete "Drosphila" and insert -- Drosophila --, therefor.

In column 23, line 8, delete "Drosphila" and insert -- Drosophila --, therefor.

In column 25, line 46, delete "1" and insert -- 1. --, therefor.

In column 30, line 28, delete "NO." and insert -- NO: --, therefor.

In column 39, line 34, delete "F," and insert -- $F_V$ --, therefor.

In column 40, line 47-53, delete "Conditions suitable for clostridial toxin protease activity can optionally include a detergent such as TWEEN-20, which can be used, for example, in place of bovine serum albumin. TWEEN-20 can be provided, for example, in the range of 0.001% to 10% (v/v) Tween-20, or in the range of 0.01% to 1.0% (v/v) Tween-20. In one embodiment, TWEEN-20 is provided at a concentration of 0.1% (v/v; see Example II)." and insert -- Conditions suitable for clostridial toxin protease activity can optionally include a detergent such as TWEEN-20® (polyoxyethylene (20) sorbitan monolaureate), which can be used, for example, in place of bovine serum albumin. TWEEN-20® (polyoxyethylene (20) sorbitan monolaureate) can be provided, for example, in the range of 0.001% to 10% (v/v) TWEEN-20® (polyoxyethylene (20) sorbitan monolaureate), or in the range of 0.01% to 1.0% (v/v) TWEEN-20® (polyoxyethylene (20) sorbitan monolaureate). In one embodiment, TWEEN-20® (polyoxyethylene (20) sorbitan monolaureate) is provided at a concentration of 0.1% (v/v; see Example II). --, therefor.

In column 40, line 54-65, delete "Conditions suitable for clostridial toxin protease activity can optionally include a detergent such as TWEEN-20 (polyoxyethylene (20) sorbitan monolaureate), which can be used, for example, in place of bovine serum albumin. TWEEN-20® (polyoxyethylene (20) sorbitan monolaureate) can be provided, for example, in the range of 0.001% to 10% (v/v) TWEEN-20® (polyoxyethylene (20) sorbitan monolaureate), or in the range of 0.01% to 1.0% (v/v) Tween-20® (polyoxyethylene (20) sorbitan monolaureate). In one embodiment, TWEEN-20® (polyoxyethylene (20) sorbitan monolaureate) is provided at a concentration of 0.1% (v/v; see Example II)." and insert -- Conditions suitable for clostridial toxin protease activity also can include, if desired, bovine serum albumin (BSA). When included, BSA typically is provided in the range of 0.1 mg/ml to 10 mg/ml. In one embodiment, BSA is included at a concentration of 1 mg/ml. See, for example, Schmidt and Bostian, supra, 1997. In another embodiment, BSA is included at a concentration of 0.1% (v/v; see Example II). --, therefor.

CERTIFICATE OF CORRECTION (continued)
U.S. Pat. No. 7,838,260 B2

In column 44, line 49, delete "pDQE50" and insert -- pQE50 --, therefor.

In column 44, line 63, delete "AGATCT" and insert -- AGA TCT --, therefor.

In column 44, line 63, delete "MC" and insert -- AAC --, therefor.

In column 45, line 6, delete "CCGCGG" and insert -- CCG CGG --, therefor.

In column 45, line 7, delete "MC" and insert -- AAC --, therefor.

In column 45, line 8, delete "CM MG" and insert -- GCT CAA --, therefor.

In column 45, line 11, delete "MG" and insert -- AAG --, therefor.

In column 45, line 39, delete "MC" and insert -- AAC --, therefor.

In column 48, line 24, delete "(DE3)" and insert -- (DE3)® --, therefor.

In column 49, line 35, delete "Oroteolysis" and insert -- proteolysis --, therefor.

In column 52, line 61, delete "Left" and insert -- Lett --, therefor.

In column 53, line 63, delete "-CODONPLUS®" and insert -- CODONPLUS® --, therefor.

In column 54, line 13-14, delete "-CODONPLUA®" and insert -- CODONPLUS® --, therefor.

In column 54, line 35, delete "KM," and insert -- $K_M$, --, therefor.

In column 55, line 51, delete "A)®" and insert -- A) --, therefor.

In column 127, line 55, in claim 4, delete "claim" and insert -- claims --, therefor.

In column 128, line 54, in claim 17, delete "(Co2+)." and insert -- $(Co^{2+})$. --, therefor.

In column 128, line 56, in claim 18, delete "(Ni2+)." and insert -- $(Ni^{2+})$. --, therefor.

SEQUENCE LISTING

```
<160> NUMBER OF SEQ ID NOS: 113

<210> SEQ ID NO 1
<211> LENGTH: 8
<212> TYPE: PRT
<213> ORGANISM: Artificial Sequence
<220> FEATURE:
<223> OTHER INFORMATION: synthetic construct

<400> SEQUENCE: 1
```

-continued

```
Glu Ala Asn Gln Arg Ala Thr Lys
 1               5

<210> SEQ ID NO 2
<211> LENGTH: 206
<212> TYPE: PRT
<213> ORGANISM: Homo sapiens

<400> SEQUENCE: 2

Met Ala Glu Asp Ala Asp Met Arg Asn Glu Leu Glu Met Gln Arg
 1               5                  10                  15

Arg Ala Asp Gln Leu Ala Asp Glu Ser Leu Glu Ser Thr Arg Arg Met
                 20                  25                  30

Leu Gln Leu Val Glu Glu Ser Lys Asp Ala Gly Ile Arg Thr Leu Val
             35                  40                  45

Met Leu Asp Glu Gln Gly Glu Gln Leu Glu Arg Ile Glu Glu Gly Met
         50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                 85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 3
<211> LENGTH: 8
<212> TYPE: PRT
<213> ORGANISM: Artificial Sequence
<220> FEATURE:
<223> OTHER INFORMATION: synthetic construct

<400> SEQUENCE: 3

Gly Ala Ser Gln Phe Glu Thr Ser
 1               5

<210> SEQ ID NO 4
<211> LENGTH: 116
<212> TYPE: PRT
<213> ORGANISM: Homo sapiens

<400> SEQUENCE: 4

Met Ser Ala Thr Ala Ala Thr Ala Pro Pro Ala Ala Pro Ala Gly Glu
 1               5                  10                  15

Gly Gly Pro Pro Ala Pro Pro Pro Asn Leu Thr Ser Asn Arg Arg Leu
                 20                  25                  30

Gln Gln Thr Gln Ala Gln Val Asp Glu Val Val Asp Ile Met Arg Val
```

```
                    35                  40                  45
Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
                100                 105                 110

Tyr Phe Ser Ser
        115

<210> SEQ ID NO 5
<211> LENGTH: 8
<212> TYPE: PRT
<213> ORGANISM: Artificial Sequence
<220> FEATURE:
<223> OTHER INFORMATION: synthetic construct

<400> SEQUENCE: 5

Asp Thr Lys Lys Ala Val Lys Trp
1               5

<210> SEQ ID NO 6
<211> LENGTH: 8
<212> TYPE: PRT
<213> ORGANISM: Artificial Sequence
<220> FEATURE:
<223> OTHER INFORMATION: synthetic construct

<400> SEQUENCE: 6

Arg Asp Gln Lys Leu Ser Glu Leu
1               5

<210> SEQ ID NO 7
<211> LENGTH: 116
<212> TYPE: PRT
<213> ORGANISM: Rattus sp.

<400> SEQUENCE: 7

Met Ser Ala Thr Ala Ala Thr Val Pro Pro Ala Ala Pro Ala Gly Glu
1               5                   10                  15

Gly Gly Pro Pro Ala Pro Pro Pro Asn Leu Thr Ser Asn Arg Arg Leu
                20                  25                  30

Gln Gln Thr Gln Ala Gln Val Asp Glu Val Val Asp Ile Met Arg Val
            35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
                100                 105                 110

Tyr Phe Ser Thr
        115

<210> SEQ ID NO 8
<211> LENGTH: 8
<212> TYPE: PRT
```

```
<213> ORGANISM: Artificial Sequence
<220> FEATURE:
<223> OTHER INFORMATION: synthetic construct

<400> SEQUENCE: 8

Gln Ile Asp Arg Ile Met Glu Lys
 1               5

<210> SEQ ID NO 9
<211> LENGTH: 8
<212> TYPE: PRT
<213> ORGANISM: Artificial Sequence
<220> FEATURE:
<223> OTHER INFORMATION: synthetic construct

<400> SEQUENCE: 9

Glu Arg Asp Gln Lys Leu Ser Glu
 1               5

<210> SEQ ID NO 10
<211> LENGTH: 8
<212> TYPE: PRT
<213> ORGANISM: Artificial Sequence
<220> FEATURE:
<223> OTHER INFORMATION: synthetic construct

<400> SEQUENCE: 10

Glu Thr Ser Ala Ala Lys Leu Lys
 1               5

<210> SEQ ID NO 11
<211> LENGTH: 8
<212> TYPE: PRT
<213> ORGANISM: Artificial Sequence
<220> FEATURE:
<223> OTHER INFORMATION: synthetic construct

<400> SEQUENCE: 11

Gly Ala Ser Gln Phe Glu Thr Ser
 1               5

<210> SEQ ID NO 12
<211> LENGTH: 206
<212> TYPE: PRT
<213> ORGANISM: Mus musculus

<400> SEQUENCE: 12

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
        50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
               100                 105                 110

Val Ala Ser Gln Pro Ala Arg Val Val Asp Glu Arg Glu Gln Met Ala
           115                 120                 125
```

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 13
<211> LENGTH: 212
<212> TYPE: PRT
<213> ORGANISM: Drosophila sp.

<400> SEQUENCE: 13

Met Pro Ala Asp Pro Ser Glu Val Ala Pro Gln Val Pro Lys Thr
1               5                   10                  15

Glu Leu Glu Glu Leu Gln Ile Asn Ala Gln Gly Val Ala Asp Glu Ser
            20                  25                  30

Leu Glu Ser Thr Arg Arg Met Leu Ala Leu Cys Glu Glu Ser Lys Glu
        35                  40                  45

Ala Gly Ile Arg Thr Leu Val Ala Leu Asp Asp Gln Gly Glu Gln Leu
    50                  55                  60

Asp Arg Ile Glu Glu Gly Met Asp Gln Ile Asn Ala Asp Met Arg Glu
65                  70                  75                  80

Ala Glu Lys Asn Leu Ser Gly Met Glu Lys Cys Cys Gly Ile Cys Val
                85                  90                  95

Leu Pro Cys Asn Lys Ser Gln Ser Phe Lys Glu Asp Asp Gly Thr Trp
            100                 105                 110

Lys Gly Asn Asp Asp Gly Lys Val Val Asn Asn Gln Pro Gln Arg Val
        115                 120                 125

Met Asp Asp Arg Asn Gly Met Met Ala Gln Ala Gly Tyr Ile Gly Arg
    130                 135                 140

Ile Thr Asn Asp Ala Arg Glu Asp Glu Met Glu Glu Asn Met Gly Gln
145                 150                 155                 160

Val Asn Thr Met Ile Gly Asn Leu Arg Asn Met Ala Leu Asp Met Gly
                165                 170                 175

Ser Glu Leu Glu Asn Gln Asn Arg Gln Ile Asp Arg Ile Asn Arg Lys
            180                 185                 190

Gly Glu Ser Asn Glu Ala Arg Ile Ala Val Ala Asn Gln Arg Ala His
        195                 200                 205

Gln Leu Leu Lys
    210

<210> SEQ ID NO 14
<211> LENGTH: 203
<212> TYPE: PRT
<213> ORGANISM: Carassius auratus

<400> SEQUENCE: 14

Met Ala Asp Glu Ala Asp Met Arg Asn Glu Leu Thr Asp Met Gln Ala
1               5                   10                  15

Arg Ala Asp Gln Leu Gly Asp Glu Ser Leu Glu Ser Thr Arg Arg Met
            20                  25                  30

```
Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
 50                  55                  60

Asp Gln Ile Asn Lys Asp Met Lys Glu Ala Glu Lys Asn Leu Thr Asp
 65                  70                  75                  80

Leu Gly Asn Leu Cys Gly Leu Cys Pro Cys Pro Cys Asn Lys Leu Lys
                 85                  90                  95

Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
            115                 120                 125

Gly Phe Ile Arg Arg Val Thr Asn Asp Ala Arg Glu Asn Glu Met Asp
            130                 135                 140

Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

Arg Ile Met Asp Met Ala Asp Ser Asn Lys Thr Arg Ile Asp Glu Ala
            180                 185                 190

Asn Gln Arg Ala Thr Lys Met Leu Gly Ser Gly
            195                 200

<210> SEQ ID NO 15
<211> LENGTH: 212
<212> TYPE: PRT
<213> ORGANISM: Strongylocentrotus purpuratus

<400> SEQUENCE: 15

Met Glu Asp Gln Asn Asp Met Asn Met Arg Ser Glu Leu Glu Glu Ile
 1               5                  10                  15

Gln Met Gln Ser Asn Met Gln Thr Asp Glu Ser Leu Glu Ser Thr Arg
                20                  25                  30

Arg Met Leu Gln Met Ala Glu Ser Gln Asp Met Gly Ile Lys Thr
            35                  40                  45

Leu Val Met Leu Asp Glu Gln Gly Glu Gln Leu Asp Arg Ile Glu Glu
 50                  55                  60

Gly Met Asp Gln Ile Asn Thr Asp Met Arg Glu Ala Glu Lys Asn Leu
 65                  70                  75                  80

Thr Gly Leu Glu Lys Cys Cys Gly Ile Cys Val Cys Pro Trp Lys Lys
                 85                  90                  95

Leu Gly Asn Phe Glu Lys Gly Asp Tyr Lys Lys Thr Trp Lys Gly
            100                 105                 110

Asn Asp Asp Gly Lys Val Asn Ser His Gln Pro Met Arg Met Glu Asp
            115                 120                 125

Asp Arg Asp Gly Cys Gly Gly Asn Ala Ser Met Ile Thr Arg Ile Thr
            130                 135                 140

Asn Asp Ala Arg Glu Asp Glu Met Asp Glu Asn Leu Thr Gln Val Ser
145                 150                 155                 160

Ser Ile Val Gly Asn Leu Arg His Met Ala Ile Asp Met Gln Ser Glu
                165                 170                 175

Ile Gly Ala Gln Asn Ser Gln Val Gly Arg Ile Thr Ser Lys Ala Glu
            180                 185                 190

Ser Asn Glu Gly Arg Ile Asn Ser Ala Asp Lys Arg Ala Lys Asn Ile
```

```
                195                 200                 205
Leu Arg Asn Lys
    210

<210> SEQ ID NO 16
<211> LENGTH: 249
<212> TYPE: PRT
<213> ORGANISM: Gallus gallus

<400> SEQUENCE: 16

Met Ala Glu Asp Ala Asp Met Arg Asn Glu Leu Glu Glu Met Gln Arg
  1               5                  10                  15

Arg Ala Asp Gln Leu Ala Asp Glu Ser Leu Glu Ser Thr Arg Arg Met
                 20                  25                  30

Leu Gln Leu Val Glu Glu Ser Lys Asp Ala Gly Ile Arg Thr Leu Val
             35                  40                  45

Met Leu Asp Glu Gln Gly Glu Gln Leu Asp Arg Val Glu Glu Gly Met
         50                  55                  60

Asn His Ile Asn Gln Asp Met Lys Glu Ala Glu Lys Asn Leu Lys Asp
 65                  70                  75                  80

Leu Gly Lys Cys Cys Gly Leu Phe Ile Cys Pro Cys Asn Lys Leu Lys
                 85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Leu Ile Pro Ile Lys Pro Gly Leu
            180                 185                 190

Met Lys Pro Thr Ser Val Gln Gln Arg Cys Ser Ala Val Val Lys Cys
        195                 200                 205

Ser Lys Val His Phe Leu Leu Met Leu Ser Gln Arg Ala Val Pro Ser
    210                 215                 220

Cys Phe Tyr His Gly Ile Tyr Leu Leu Gly Leu His Thr Cys Thr Tyr
225                 230                 235                 240

Gln Pro His Cys Lys Cys Cys Pro Val
                245

<210> SEQ ID NO 17
<211> LENGTH: 116
<212> TYPE: PRT
<213> ORGANISM: Mus musculus

<400> SEQUENCE: 17

Met Ser Ala Thr Ala Ala Thr Val Pro Pro Ala Pro Ala Gly Glu
  1               5                  10                  15

Gly Gly Pro Pro Ala Pro Pro Pro Asn Leu Thr Ser Asn Arg Arg Leu
                 20                  25                  30

Gln Gln Thr Gln Ala Gln Val Asp Glu Val Val Asp Ile Met Arg Val
             35                  40                  45

Asn Val Asp Lys Val Leu Glu Arg Asp Gln Lys Leu Ser Glu Leu Asp
```

```
                50                    55                    60
Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
                     85                  90                  95

Ile Ile Leu Gly Val Ile Cys Ala Ile Ile Leu Ile Ile Ile Ile Val
                    100                 105                 110

Tyr Phe Ser Thr
            115

<210> SEQ ID NO 18
<211> LENGTH: 116
<212> TYPE: PRT
<213> ORGANISM: Bos taurus

<400> SEQUENCE: 18

Met Ser Ala Thr Ala Ala Thr Ala Pro Pro Ala Ala Pro Ala Gly Glu
 1               5                  10                  15

Gly Gly Pro Pro Ala Pro Pro Asn Leu Thr Ser Asn Arg Arg Leu
                20                  25                  30

Gln Gln Thr Gln Ala Gln Val Asp Glu Val Val Asp Ile Met Arg Val
                35                  40                  45

Asn Val Asp Lys Val Leu Glu Arg Asp Gln Lys Leu Ser Glu Leu Asp
 50                  55                  60

Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
                     85                  90                  95

Ile Ile Leu Gly Val Ile Cys Ala Ile Ile Leu Ile Ile Ile Ile Val
                    100                 105                 110

Tyr Phe Ser Ser
            115

<210> SEQ ID NO 19
<211> LENGTH: 114
<212> TYPE: PRT
<213> ORGANISM: Xenopus laevis

<400> SEQUENCE: 19

Met Ser Ala Pro Ala Ala Gly Pro Pro Ala Ala Pro Gly Asp Gly
 1               5                  10                  15

Ala Pro Gln Gly Pro Pro Asn Leu Thr Ser Asn Arg Arg Leu Gln Gln
                20                  25                  30

Thr Gln Ala Gln Val Asp Glu Val Val Asp Ile Met Arg Val Asn Val
                35                  40                  45

Asp Lys Val Leu Glu Arg Asp Thr Lys Leu Ser Glu Leu Asp Asp Arg
 50                  55                  60

Ala Asp Ala Leu Gln Ala Gly Ala Ser Gln Phe Glu Thr Ser Ala Ala
 65                  70                  75                  80

Lys Leu Lys Arg Lys Tyr Trp Trp Lys Asn Met Lys Met Met Ile Ile
                     85                  90                  95

Met Gly Val Ile Cys Ala Ile Ile Leu Ile Ile Ile Ile Val Tyr Phe
                    100                 105                 110

Ser Thr

<210> SEQ ID NO 20
```

<211> LENGTH: 104
<212> TYPE: PRT
<213> ORGANISM: Strongylocentrotus purpuratus

<400> SEQUENCE: 20

```
Met Ala Ala Pro Pro Pro Gln Pro Ala Pro Ser Asn Lys Arg Leu
 1               5                  10                  15

Gln Gln Thr Gln Ala Gln Val Asp Glu Val Val Asp Ile Met Arg Val
             20                  25                  30

Asn Val Asp Lys Val Leu Glu Arg Asp Gln Ala Leu Ser Val Leu Asp
         35                  40                  45

Asp Arg Ala Asp Ala Leu Gln Gln Gly Ala Ser Gln Phe Glu Thr Asn
     50                  55                  60

Ala Gly Lys Leu Lys Arg Lys Tyr Trp Trp Lys Asn Cys Lys Met Met
 65                  70                  75                  80

Ile Ile Leu Ala Ile Ile Ile Val Ile Leu Ile Ile Ile Val
                 85                  90                  95

Ala Ile Val Gln Ser Gln Lys Lys
                100
```

<210> SEQ ID NO 21
<211> LENGTH: 288
<212> TYPE: PRT
<213> ORGANISM: Homo sapiens

<400> SEQUENCE: 21

```
Met Lys Asp Arg Thr Gln Glu Leu Arg Thr Ala Lys Asp Ser Asp Asp
 1               5                  10                  15

Asp Asp Asp Val Ala Val Thr Val Asp Arg Asp Arg Phe Met Asp Glu
             20                  25                  30

Phe Phe Glu Gln Val Glu Glu Ile Arg Gly Phe Ile Asp Lys Ile Ala
         35                  40                  45

Glu Asn Val Glu Glu Val Lys Arg Lys His Ser Ala Ile Leu Ala Ser
     50                  55                  60

Pro Asn Pro Asp Glu Lys Thr Lys Glu Glu Leu Glu Glu Leu Met Ser
 65                  70                  75                  80

Asp Ile Lys Lys Thr Ala Asn Lys Val Arg Ser Lys Leu Lys Ser Ile
                 85                  90                  95

Glu Gln Ser Ile Glu Gln Glu Glu Gly Leu Asn Arg Ser Ser Ala Asp
                100                 105                 110

Leu Arg Ile Arg Lys Thr Gln His Ser Thr Leu Ser Arg Lys Phe Val
            115                 120                 125

Glu Val Met Ser Glu Tyr Asn Ala Thr Gln Ser Asp Tyr Arg Glu Arg
        130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ala
225                 230                 235                 240
```

```
Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
            260                 265                 270

Val Ile Leu Gly Ile Val Ile Ala Ser Thr Val Gly Gly Ile Phe Ala
        275                 280                 285

<210> SEQ ID NO 22
<211> LENGTH: 288
<212> TYPE: PRT
<213> ORGANISM: Homo sapiens

<400> SEQUENCE: 22

Met Lys Asp Arg Thr Gln Glu Leu Arg Ser Ala Lys Asp Ser Asp Asp
  1               5                  10                  15

Glu Glu Glu Val Val His Val Asp Arg Asp His Phe Met Asp Glu Phe
                 20                  25                  30

Phe Glu Gln Val Glu Glu Ile Arg Gly Cys Ile Glu Lys Leu Ser Glu
             35                  40                  45

Asp Val Glu Gln Val Lys Lys Gln His Ser Ala Ile Leu Ala Ala Pro
         50                  55                  60

Asn Pro Asp Glu Lys Thr Lys Gln Glu Leu Glu Asp Leu Thr Ala Asp
 65                  70                  75                  80

Ile Lys Lys Thr Ala Asn Lys Val Arg Ser Lys Leu Lys Ala Ile Glu
                 85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Ile Cys Cys Val
            260                 265                 270

Val Leu Gly Val Val Leu Ala Ser Ser Ile Gly Gly Thr Leu Gly Leu
        275                 280                 285

<210> SEQ ID NO 23
<211> LENGTH: 288
<212> TYPE: PRT
<213> ORGANISM: Mus musculus

<400> SEQUENCE: 23
```

Met Lys Asp Arg Thr Gln Glu Leu Arg Thr Ala Lys Asp Ser Asp Asp
1               5                   10                  15

Asp Asp Asp Val Thr Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Thr Ser
        195                 200                 205

Ile Arg Glu Leu His Asp Met Phe Met Asp Met Ala Met Leu Val Glu
210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
            260                 265                 270

Val Ile Leu Gly Ile Ile Ala Ser Thr Ile Gly Gly Ile Phe Gly
        275                 280                 285

<210> SEQ ID NO 24
<211> LENGTH: 291
<212> TYPE: PRT
<213> ORGANISM: Drosophila sp.

<400> SEQUENCE: 24

Met Thr Lys Asp Arg Leu Ala Ala Leu His Ala Ala Gln Ser Asp Asp
1               5                   10                  15

Glu Glu Glu Thr Glu Val Ala Val Asn Val Asp Gly His Asp Ser Tyr
            20                  25                  30

Met Asp Asp Phe Phe Ala Gln Val Glu Glu Ile Arg Gly Met Ile Asp
        35                  40                  45

Lys Val Gln Asp Asn Val Glu Glu Val Lys Lys His Ser Ala Ile
    50                  55                  60

Leu Ser Ala Pro Gln Thr Asp Glu Lys Thr Lys Gln Glu Leu Glu Asp
65                  70                  75                  80

Leu Met Ala Asp Ile Lys Lys Asn Ala Asn Arg Val Arg Gly Lys Leu

```
                85                  90                  95
Lys Gly Ile Glu Gln Asn Ile Glu Gln Glu Gln Gln Asn Lys Ser
            100                 105                 110
Ser Ala Asp Leu Arg Ile Arg Lys Thr Gln His Ser Thr Leu Ser Arg
            115                 120                 125
Lys Phe Val Glu Val Met Thr Glu Tyr Asn Arg Thr Gln Thr Asp Tyr
        130                 135                 140
Arg Glu Arg Cys Lys Gly Arg Ile Gln Arg Gln Leu Glu Ile Thr Gly
145                 150                 155                 160
Arg Pro Thr Asn Asp Asp Glu Leu Glu Lys Met Leu Glu Glu Gly Asn
                165                 170                 175
Ser Ser Val Phe Thr Gln Gly Ile Ile Met Glu Thr Gln Gln Ala Lys
            180                 185                 190
Gln Thr Leu Ala Asp Ile Glu Ala Arg His Gln Asp Ile Met Lys Leu
        195                 200                 205
Glu Thr Ser Ile Lys Glu Leu His Asp Met Phe Met Asp Met Ala Met
    210                 215                 220
Leu Val Glu Ser Gln Gly Glu Met Ile Asp Arg Ile Glu Tyr His Val
225                 230                 235                 240
Glu His Ala Met Asp Tyr Val Gln Thr Ala Thr Gln Asp Thr Lys Lys
                245                 250                 255
Ala Leu Lys Tyr Gln Ser Lys Ala Arg Arg Lys Lys Ile Met Ile Leu
            260                 265                 270
Ile Cys Leu Thr Val Leu Gly Ile Leu Ala Ala Ser Tyr Val Ser Ser
        275                 280                 285
Tyr Phe Met
    290

<210> SEQ ID NO 25
<211> LENGTH: 291
<212> TYPE: PRT
<213> ORGANISM: Caenorhabditis elegans

<400> SEQUENCE: 25

Met Thr Lys Asp Arg Leu Ser Ala Leu Lys Ala Ala Gln Ser Glu Asp
1               5                  10                  15
Glu Gln Asp Asp Met His Met Asp Thr Gly Asn Ala Gln Tyr Met
            20                  25                  30
Glu Glu Phe Phe Glu Gln Val Glu Glu Ile Arg Gly Ser Val Asp Ile
        35                  40                  45
Ile Ala Asn Asn Val Glu Glu Val Lys Lys Lys His Ser Ala Ile Leu
    50                  55                  60
Ser Asn Pro Val Asn Asp Gln Lys Thr Lys Glu Glu Leu Asp Glu Leu
65                  70                  75                  80
Met Ala Val Ile Lys Arg Ala Ala Asn Lys Val Arg Gly Lys Leu Lys
                85                  90                  95
Leu Ile Glu Asn Ala Ile Asp His Asp Glu Gln Gly Ala Gly Asn Ala
            100                 105                 110
Asp Leu Arg Ile Arg Lys Thr Gln His Ser Thr Leu Ser Arg Arg Phe
        115                 120                 125
Val Glu Val Met Thr Asp Tyr Asn Lys Thr Gln Thr Asp Tyr Arg Glu
    130                 135                 140
Arg Cys Lys Gly Arg Ile Gln Arg Gln Leu Asp Ile Ala Gly Lys Gln
145                 150                 155                 160
```

```
Val Gly Asp Glu Asp Leu Glu Met Ile Glu Ser Gly Asn Pro Gly
            165                 170                 175

Val Phe Thr Gln Gly Ile Ile Thr Asp Thr Gln Gln Ala Lys Gln Thr
            180                 185                 190

Leu Ala Asp Ile Glu Ala Arg His Asn Asp Ile Met Lys Leu Glu Ser
            195                 200                 205

Ser Ile Arg Glu Leu His Asp Met Phe Met Asp Met Ala Met Leu Val
            210                 215                 220

Glu Ser Gln Gly Glu Met Val Asp Arg Ile Glu Tyr Asn Val Glu His
225                 230                 235                 240

Ala Lys Glu Phe Val Asp Arg Ala Val Ala Asp Thr Lys Lys Ala Val
            245                 250                 255

Gln Tyr Gln Ser Lys Ala Arg Arg Lys Lys Ile Cys Ile Leu Val Thr
            260                 265                 270

Gly Val Ile Leu Ile Thr Gly Leu Ile Ile Phe Ile Leu Phe Tyr Ala
            275                 280                 285

Lys Val Leu
            290

<210> SEQ ID NO 26
<211> LENGTH: 288
<212> TYPE: PRT
<213> ORGANISM: Strongylocentrotus purpuratus

<400> SEQUENCE: 26

Met Arg Asp Arg Leu Gly Ser Leu Lys Arg Asn Glu Glu Asp Asp Val
 1                5                  10                  15

Gly Pro Glu Val Ala Val Asn Val Glu Ser Glu Lys Phe Met Glu Glu
            20                  25                  30

Phe Phe Glu Gln Val Glu Glu Val Arg Asn Asn Ile Asp Lys Ile Ser
            35                  40                  45

Lys Asn Val Asp Glu Val Lys Lys His Ser Asp Ile Leu Ser Ala
            50                  55                  60

Pro Gln Ala Asp Glu Lys Val Lys Asp Glu Leu Glu Glu Leu Met Ser
65                  70                  75                  80

Asp Ile Lys Lys Thr Ala Asn Lys Val Arg Ala Lys Leu Lys Met Met
                85                  90                  95

Glu Gln Ser Ile Glu Gln Glu Glu Ser Ala Lys Met Asn Ser Ala Asp
            100                 105                 110

Val Arg Ile Arg Lys Thr Gln His Ser Thr Leu Ser Arg Lys Phe Val
            115                 120                 125

Glu Val Met Thr Asp Tyr Asn Ser Thr Gln Thr Asp Tyr Arg Glu Arg
            130                 135                 140

Cys Lys Gly Arg Ile Gln Arg Gln Leu Glu Ile Thr Gly Lys Ser Thr
145                 150                 155                 160

Thr Asp Ala Glu Leu Glu Asp Met Leu Glu Ser Gly Asn Pro Ala Ile
            165                 170                 175

Phe Thr Ser Gly Ile Ile Met Asp Thr Gln Ala Lys Gln Thr Leu
            180                 185                 190

Arg Asp Ile Glu Ala Arg His Asn Asp Ile Lys Leu Glu Ser Ser
            195                 200                 205

Ile Arg Glu Leu His Asp Met Phe Met Asp Met Ala Met Leu Val Glu
            210                 215                 220

Ser Gln Gly Glu Met Ile Asp Arg Ile Glu Tyr Asn Val Glu Gln Ser
225                 230                 235                 240
```

```
Val Asp Tyr Val Glu Thr Ala Lys Met Asp Thr Lys Lys Ala Val Lys
                245                 250                 255

Tyr Gln Ser Lys Ala Arg Arg Lys Lys Phe Tyr Ile Ala Ile Cys Cys
            260                 265                 270

Gly Val Ala Leu Gly Ile Leu Val Leu Ile Ile Val Leu Ala
        275                 280                 285

<210> SEQ ID NO 27
<211> LENGTH: 13
<212> TYPE: PRT
<213> ORGANISM: Homo sapiens

<400> SEQUENCE: 27

Thr Arg Ile Asp Glu Ala Asn Gln Arg Ala Thr Lys Met
1               5                   10

<210> SEQ ID NO 28
<211> LENGTH: 15
<212> TYPE: PRT
<213> ORGANISM: Homo sapiens

<400> SEQUENCE: 28

Ser Asn Lys Thr Arg Ile Asp Glu Ala Asn Gln Arg Ala Thr Lys
1               5                   10                  15

<210> SEQ ID NO 29
<211> LENGTH: 16
<212> TYPE: PRT
<213> ORGANISM: Homo sapiens

<400> SEQUENCE: 29

Ser Asn Lys Thr Arg Ile Asp Glu Ala Asn Gln Arg Ala Thr Lys Met
1               5                   10                  15

<210> SEQ ID NO 30
<211> LENGTH: 17
<212> TYPE: PRT
<213> ORGANISM: Homo sapiens

<400> SEQUENCE: 30

Ser Asn Lys Thr Arg Ile Asp Glu Ala Asn Gln Arg Ala Thr Lys Met
1               5                   10                  15

Leu

<210> SEQ ID NO 31
<211> LENGTH: 17
<212> TYPE: PRT
<213> ORGANISM: Homo sapiens

<400> SEQUENCE: 31

Asp Ser Asn Lys Thr Arg Ile Asp Glu Ala Asn Gln Arg Ala Thr Lys
1               5                   10                  15

Met

<210> SEQ ID NO 32
<211> LENGTH: 18
<212> TYPE: PRT
<213> ORGANISM: Homo sapiens

<400> SEQUENCE: 32

Asp Ser Asn Lys Thr Arg Ile Asp Glu Ala Asn Gln Arg Ala Thr Lys
1               5                   10                  15
```

Met Leu

<210> SEQ ID NO 33
<211> LENGTH: 33
<212> TYPE: PRT
<213> ORGANISM: Mus musculus

<400> SEQUENCE: 33

Gln Asn Arg Gln Ile Asp Arg Ile Met Glu Lys Ala Asp Ser Asn Lys
1               5                   10                  15

Thr Arg Ile Asp Glu Ala Asn Gln Arg Ala Thr Lys Met Leu Gly Ser
            20                  25                  30

Gly

<210> SEQ ID NO 34
<211> LENGTH: 32
<212> TYPE: PRT
<213> ORGANISM: Homo sapiens

<400> SEQUENCE: 34

Gln Asn Pro Gln Ile Lys Arg Ile Thr Asp Lys Ala Asp Thr Asn Arg
1               5                   10                  15

Asp Arg Ile Asp Ile Ala Asn Ala Arg Ala Lys Lys Leu Ile Asp Ser
            20                  25                  30

<210> SEQ ID NO 35
<211> LENGTH: 32
<212> TYPE: PRT
<213> ORGANISM: Mus musculus

<400> SEQUENCE: 35

Gln Asn Gln Gln Ile Gln Lys Ile Thr Glu Lys Ala Asp Thr Asn Lys
1               5                   10                  15

Asn Arg Ile Asp Ile Ala Asn Thr Arg Ala Lys Lys Leu Ile Asp Ser
            20                  25                  30

<210> SEQ ID NO 36
<211> LENGTH: 34
<212> TYPE: PRT
<213> ORGANISM: Gallus gallus

<400> SEQUENCE: 36

Gln Asn Arg Gln Ile Asp Arg Ile Met Glu Lys Leu Ile Pro Ile Lys
1               5                   10                  15

Pro Gly Leu Met Lys Pro Thr Ser Val Gln Gln Arg Cys Ser Ala Val
            20                  25                  30

Val Lys

<210> SEQ ID NO 37
<211> LENGTH: 33
<212> TYPE: PRT
<213> ORGANISM: Carassius auratus

<400> SEQUENCE: 37

Gln Asn Arg Gln Ile Asp Arg Ile Met Asp Met Ala Asp Ser Asn Lys
1               5                   10                  15

Thr Arg Ile Asp Glu Ala Asn Gln Arg Ala Thr Lys Met Leu Gly Ser
            20                  25                  30

Gly

<210> SEQ ID NO 38
<211> LENGTH: 33
<212> TYPE: PRT
<213> ORGANISM: Carassius auratus

<400> SEQUENCE: 38

Gln Asn Arg Gln Ile Asp Arg Ile Met Glu Lys Ala Asp Ser Asn Lys
 1               5                  10                  15

Thr Arg Ile Asp Glu Ala Asn Gln Arg Ala Thr Lys Met Leu Gly Ser
            20                  25                  30

Gly

<210> SEQ ID NO 39
<211> LENGTH: 30
<212> TYPE: PRT
<213> ORGANISM: Torpedo sp.

<400> SEQUENCE: 39

Gln Asn Ala Gln Val Asp Arg Ile Val Val Lys Gly Asp Met Asn Lys
 1               5                  10                  15

Ala Arg Ile Asp Glu Ala Asn Lys His Ala Thr Lys Met Leu
            20                  25                  30

<210> SEQ ID NO 40
<211> LENGTH: 33
<212> TYPE: PRT
<213> ORGANISM: Strongylocentrotus purpuratus

<400> SEQUENCE: 40

Gln Asn Ser Gln Val Gly Arg Ile Thr Ser Lys Ala Glu Ser Asn Glu
 1               5                  10                  15

Gly Arg Ile Asn Ser Ala Asp Lys Arg Ala Lys Asn Ile Leu Arg Asn
            20                  25                  30

Lys

<210> SEQ ID NO 41
<211> LENGTH: 31
<212> TYPE: PRT
<213> ORGANISM: Caenorhabditis elagans

<400> SEQUENCE: 41

Gln Asn Arg Gln Leu Asp Arg Ile His Asp Lys Gln Ser Asn Glu Val
 1               5                  10                  15

Arg Val Glu Ser Ala Asn Lys Arg Ala Lys Asn Leu Ile Thr Lys
            20                  25                  30

<210> SEQ ID NO 42
<211> LENGTH: 31
<212> TYPE: PRT
<213> ORGANISM: Drosophila sp.

<400> SEQUENCE: 42

Gln Asn Arg Gln Ile Asp Arg Ile Asn Arg Lys Gly Glu Ser Asn Glu
 1               5                  10                  15

Ala Arg Ile Ala Val Ala Asn Gln Arg Ala His Gln Leu Leu Lys
            20                  25                  30

<210> SEQ ID NO 43
<211> LENGTH: 32
<212> TYPE: PRT
<213> ORGANISM: Hirudinida sp.

<400> SEQUENCE: 43

Gln Asn Arg Gln Val Asp Arg Ile Asn Asn Lys Met Thr Ser Asn Gln
1               5                   10                  15

Leu Arg Ile Ser Asp Ala Asn Lys Arg Ala Ser Lys Leu Leu Lys Glu
            20                  25                  30

<210> SEQ ID NO 44
<211> LENGTH: 17
<212> TYPE: PRT
<213> ORGANISM: Artificial Sequence
<220> FEATURE:
<223> OTHER INFORMATION: synthetic peptide

<400> SEQUENCE: 44

Ser Asn Lys Thr Arg Ile Asp Glu Ala Asn Gln Arg Ala Thr Lys Ala
1               5                   10                  15

Leu

<210> SEQ ID NO 45
<211> LENGTH: 17
<212> TYPE: PRT
<213> ORGANISM: Artificial Sequence
<220> FEATURE:
<223> OTHER INFORMATION: synthetic peptide
<221> NAME/KEY: MOD_RES
<222> LOCATION: 16
<223> OTHER INFORMATION: Xaa=Nle

<400> SEQUENCE: 45

Ser Asn Lys Thr Arg Ile Asp Glu Ala Asn Gln Arg Ala Thr Lys Xaa
1               5                   10                  15

Leu

<210> SEQ ID NO 46
<211> LENGTH: 17
<212> TYPE: PRT
<213> ORGANISM: Artificial Sequence
<220> FEATURE:
<223> OTHER INFORMATION: synthetic peptide

<400> SEQUENCE: 46

Ser Asn Lys Thr Arg Ile Asp Glu Ala Asn Gln Arg Ala Thr Ala Met
1               5                   10                  15

Leu

<210> SEQ ID NO 47
<211> LENGTH: 17
<212> TYPE: PRT
<213> ORGANISM: Artificial Sequence
<220> FEATURE:
<223> OTHER INFORMATION: synthetic peptide

<400> SEQUENCE: 47

Ser Asn Lys Thr Arg Ile Asp Glu Ala Asn Gln Arg Ala Ser Lys Met
1               5                   10                  15

Leu

<210> SEQ ID NO 48
<211> LENGTH: 17
<212> TYPE: PRT
<213> ORGANISM: Artificial Sequence
<220> FEATURE:
<223> OTHER INFORMATION: synthetic peptide

```
<221> NAME/KEY: MOD_RES
<222> LOCATION: 14
<223> OTHER INFORMATION: Xaa=Abu

<400> SEQUENCE: 48

Ser Asn Lys Thr Arg Ile Asp Glu Ala Asn Gln Arg Ala Xaa Lys Met
1               5                   10                  15
Leu

<210> SEQ ID NO 49
<211> LENGTH: 17
<212> TYPE: PRT
<213> ORGANISM: Artificial Sequence
<220> FEATURE:
<223> OTHER INFORMATION: synthetic peptide
<221> NAME/KEY: MOD_RES
<222> LOCATION: 13
<223> OTHER INFORMATION: Xaa=Abu

<400> SEQUENCE: 49

Ser Asn Lys Thr Arg Ile Asp Glu Ala Asn Gln Arg Xaa Thr Lys Met
1               5                   10                  15
Leu

<210> SEQ ID NO 50
<211> LENGTH: 17
<212> TYPE: PRT
<213> ORGANISM: Artificial Sequence
<220> FEATURE:
<223> OTHER INFORMATION: synthetic peptide

<400> SEQUENCE: 50

Ser Asn Lys Thr Arg Ile Asp Glu Ala Asn Ala Arg Ala Thr Lys Met
1               5                   10                  15
Leu

<210> SEQ ID NO 51
<211> LENGTH: 17
<212> TYPE: PRT
<213> ORGANISM: Artificial Sequence
<220> FEATURE:
<223> OTHER INFORMATION: synthetic peptide
<221> NAME/KEY: MOD_RES
<222> LOCATION: 11
<223> OTHER INFORMATION: Xaa=Abu

<400> SEQUENCE: 51

Ser Asn Lys Thr Arg Ile Asp Glu Ala Asn Xaa Arg Ala Thr Lys Met
1               5                   10                  15
Leu

<210> SEQ ID NO 52
<211> LENGTH: 17
<212> TYPE: PRT
<213> ORGANISM: Artificial Sequence
<220> FEATURE:
<223> OTHER INFORMATION: synthetic peptide

<400> SEQUENCE: 52

Ser Asn Lys Thr Arg Ile Asp Glu Ala Asn Asn Arg Ala Thr Lys Met
1               5                   10                  15
Leu

<210> SEQ ID NO 53
```

```
<211> LENGTH: 17
<212> TYPE: PRT
<213> ORGANISM: Artificial Sequence
<220> FEATURE:
<223> OTHER INFORMATION: synthetic peptide

<400> SEQUENCE: 53

Ser Asn Lys Thr Arg Ile Asp Glu Ala Ala Gln Arg Ala Thr Lys Met
1               5                   10                  15

Leu

<210> SEQ ID NO 54
<211> LENGTH: 17
<212> TYPE: PRT
<213> ORGANISM: Artificial Sequence
<220> FEATURE:
<223> OTHER INFORMATION: synthetic peptide
<221> NAME/KEY: MOD_RES
<222> LOCATION: 9
<223> OTHER INFORMATION: Xaa=Abu

<400> SEQUENCE: 54

Ser Asn Lys Thr Arg Ile Asp Glu Xaa Asn Gln Arg Ala Thr Lys Met
1               5                   10                  15

Leu

<210> SEQ ID NO 55
<211> LENGTH: 17
<212> TYPE: PRT
<213> ORGANISM: Artificial Sequence
<220> FEATURE:
<223> OTHER INFORMATION: synthetic peptide

<400> SEQUENCE: 55

Ser Asn Lys Thr Arg Ile Asp Gln Ala Asn Gln Arg Ala Thr Lys Met
1               5                   10                  15

Leu

<210> SEQ ID NO 56
<211> LENGTH: 17
<212> TYPE: PRT
<213> ORGANISM: Artificial Sequence
<220> FEATURE:
<223> OTHER INFORMATION: synthetic peptide

<400> SEQUENCE: 56

Ser Asn Lys Thr Arg Ile Asn Glu Ala Asn Gln Arg Ala Thr Lys Met
1               5                   10                  15

Leu

<210> SEQ ID NO 57
<211> LENGTH: 40
<212> TYPE: PRT
<213> ORGANISM: Homo sapiens

<400> SEQUENCE: 57

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Ser Ser Ala Ala
                20                  25                  30

Lys Leu Lys Arg Lys Tyr Trp Trp
                35                  40
```

```
<210> SEQ ID NO 58
<211> LENGTH: 40
<212> TYPE: PRT
<213> ORGANISM: Bos taurus

<400> SEQUENCE: 58

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Thr Ser Ala Ala
            20                  25                  30

Lys Leu Lys Arg Lys Tyr Trp Trp
        35                  40

<210> SEQ ID NO 59
<211> LENGTH: 40
<212> TYPE: PRT
<213> ORGANISM: Rattus sp.

<400> SEQUENCE: 59

Asp Lys Val Leu Glu Arg Asp Gln Lys Leu Ser Glu Leu Asp Asp Arg
1               5                   10                  15

Ala Asp Ala Leu Gln Ala Gly Ala Ser Val Phe Glu Ser Ser Ala Ala
            20                  25                  30

Lys Leu Lys Arg Lys Tyr Trp Trp
        35                  40

<210> SEQ ID NO 60
<211> LENGTH: 40
<212> TYPE: PRT
<213> ORGANISM: Rattus sp.

<400> SEQUENCE: 60

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Thr Ser Ala Ala
            20                  25                  30

Lys Leu Lys Arg Lys Tyr Trp Trp
        35                  40

<210> SEQ ID NO 61
<211> LENGTH: 40
<212> TYPE: PRT
<213> ORGANISM: Rattus sp.

<400> SEQUENCE: 61

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Thr Ser Ala Ala
            20                  25                  30

Lys Leu Lys Arg Lys Tyr Trp Trp
        35                  40

<210> SEQ ID NO 62
<211> LENGTH: 40
<212> TYPE: PRT
<213> ORGANISM: Rattus sp.

<400> SEQUENCE: 62

Asp Leu Val Ala Gln Arg Gly Glu Arg Leu Glu Leu Leu Ile Asp Lys
1               5                   10                  15

Thr Glu Asn Leu Val Asp Ser Ser Val Thr Phe Lys Thr Thr Ser Arg
```

```
                    20                  25                  30

Asn Leu Ala Arg Ala Met Cys Met
            35                  40

<210> SEQ ID NO 63
<211> LENGTH: 32
<212> TYPE: PRT
<213> ORGANISM: Gallus gallus

<400> SEQUENCE: 63

Glu Arg Asp Gln Lys Leu Ser Glu Leu Asp Asp Arg Ala Asp Ala Leu
1               5                  10                  15

Gln Ala Gly Ala Ser Val Phe Glu Ser Ser Ala Ala Lys Leu Lys Arg
            20                  25                  30

<210> SEQ ID NO 64
<211> LENGTH: 32
<212> TYPE: PRT
<213> ORGANISM: Gallus gallus

<400> SEQUENCE: 64

Glu Arg Asp Gln Lys Leu Ser Glu Leu Asp Asp Arg Ala Asp Ala Leu
1               5                  10                  15

Gln Ala Gly Ala Ser Gln Phe Glu Thr Ser Ala Ala Lys Leu Lys Arg
            20                  25                  30

<210> SEQ ID NO 65
<211> LENGTH: 40
<212> TYPE: PRT
<213> ORGANISM: Torpedo sp.

<400> SEQUENCE: 65

Asp Lys Val Leu Glu Arg Asp Gln Lys Leu Ser Glu Leu Asp Asp Arg
1               5                  10                  15

Ala Asp Ala Leu Gln Ala Gly Ala Ser Gln Phe Glu Ser Ser Ala Ala
            20                  25                  30

Lys Leu Lys Arg Lys Tyr Trp Trp
            35                  40

<210> SEQ ID NO 66
<211> LENGTH: 40
<212> TYPE: PRT
<213> ORGANISM: Strongylocentrotus purpuratus

<400> SEQUENCE: 66

Asp Lys Val Leu Asp Arg Asp Gly Ala Leu Ser Val Leu Asp Asp Arg
1               5                  10                  15

Ala Asp Ala Leu Gln Gln Gly Ala Ser Gln Phe Glu Thr Asn Ala Gly
            20                  25                  30

Lys Leu Lys Arg Lys Tyr Trp Trp
            35                  40

<210> SEQ ID NO 67
<211> LENGTH: 40
<212> TYPE: PRT
<213> ORGANISM: Aplysia sp.

<400> SEQUENCE: 67

Glu Lys Val Leu Asp Arg Asp Gln Lys Ile Ser Gln Leu Asp Asp Arg
1               5                  10                  15

Ala Glu Ala Leu Gln Ala Gly Ala Ser Gln Phe Glu Ala Ser Ala Gly
```

```
                20                  25                  30
Lys Leu Lys Arg Lys Tyr Trp Trp
            35                  40

<210> SEQ ID NO 68
<211> LENGTH: 40
<212> TYPE: PRT
<213> ORGANISM: Teuthoida sp.

<400> SEQUENCE: 68

Asp Lys Val Leu Glu Arg Asp Ser Lys Ile Ser Glu Leu Asp Arg
1               5                   10                  15

Ala Asp Ala Leu Gln Ala Gly Ala Ser Gln Phe Glu Ala Ser Ala Gly
            20                  25                  30

Lys Leu Lys Arg Lys Phe Trp Trp
            35                  40

<210> SEQ ID NO 69
<211> LENGTH: 40
<212> TYPE: PRT
<213> ORGANISM: Caenorhabditis elegans

<400> SEQUENCE: 69

Asn Lys Val Met Glu Arg Asp Val Gln Leu Asn Ser Leu Asp His Arg
1               5                   10                  15

Ala Glu Val Leu Gln Asn Gly Ala Ser Gln Phe Gln Gln Ser Ser Arg
            20                  25                  30

Glu Leu Lys Arg Gln Tyr Trp Trp
            35                  40

<210> SEQ ID NO 70
<211> LENGTH: 40
<212> TYPE: PRT
<213> ORGANISM: Drosophila sp.

<400> SEQUENCE: 70

Glu Lys Val Leu Glu Arg Asp Gln Lys Leu Ser Glu Leu Gly Glu Arg
1               5                   10                  15

Ala Asp Gln Leu Glu Gly Gly Ala Ser Gln Ser Glu Gln Gln Ala Gly
            20                  25                  30

Lys Leu Lys Arg Lys Gln Trp Trp
            35                  40

<210> SEQ ID NO 71
<211> LENGTH: 40
<212> TYPE: PRT
<213> ORGANISM: Drosophila sp.

<400> SEQUENCE: 71

Glu Lys Val Leu Glu Arg Asp Ser Lys Leu Ser Glu Leu Asp Asp Arg
1               5                   10                  15

Ala Asp Ala Leu Gln Gln Gly Ala Ser Gln Phe Glu Gln Gln Ala Gly
            20                  25                  30

Lys Leu Lys Arg Lys Phe Trp Leu
            35                  40

<210> SEQ ID NO 72
<211> LENGTH: 39
<212> TYPE: PRT
<213> ORGANISM: Hirudinida sp.
```

```
<400> SEQUENCE: 72

Asp Lys Val Leu Glu Lys Asp Gln Lys Leu Ala Glu Leu Asp Arg Ala
1               5                   10                  15

Asp Ala Leu Gln Ala Gly Ala Ser Gln Phe Glu Ala Ser Ala Gly Lys
            20                  25                  30

Leu Lys Arg Lys Phe Trp Trp
            35

<210> SEQ ID NO 73
<211> LENGTH: 18
<212> TYPE: PRT
<213> ORGANISM: Homo sapiens

<400> SEQUENCE: 73

Glu Arg Ala Val Ser Asp Thr Lys Lys Ala Val Lys Tyr Gln Ser Lys
1               5                   10                  15

Ala Arg

<210> SEQ ID NO 74
<211> LENGTH: 18
<212> TYPE: PRT
<213> ORGANISM: Bos taurus

<400> SEQUENCE: 74

Glu Arg Ala Val Ser Asp Thr Lys Lys Ala Val Lys Tyr Gln Ser Lys
1               5                   10                  15

Ala Arg

<210> SEQ ID NO 75
<211> LENGTH: 18
<212> TYPE: PRT
<213> ORGANISM: Rattus sp.

<400> SEQUENCE: 75

Glu His Ala Lys Glu Glu Thr Lys Lys Ala Ile Lys Tyr Gln Ser Lys
1               5                   10                  15

Ala Arg

<210> SEQ ID NO 76
<211> LENGTH: 18
<212> TYPE: PRT
<213> ORGANISM: Rattus sp.

<400> SEQUENCE: 76

Glu Lys Ala Arg Asp Glu Thr Arg Lys Ala Met Lys Tyr Gln Gly Gly
1               5                   10                  15

Ala Arg

<210> SEQ ID NO 77
<211> LENGTH: 18
<212> TYPE: PRT
<213> ORGANISM: Rattus sp.

<400> SEQUENCE: 77

Glu Arg Gly Gln Glu His Val Lys Ile Ala Leu Glu Asn Gln Lys Lys
1               5                   10                  15

Ala Arg

<210> SEQ ID NO 78
<211> LENGTH: 18
```

-continued

```
<212> TYPE: PRT
<213> ORGANISM: Gallus gallus

<400> SEQUENCE: 78

Val Pro Glu Val Phe Val Thr Lys Ser Ala Val Met Tyr Gln Cys Lys
1               5                   10                  15

Ser Arg

<210> SEQ ID NO 79
<211> LENGTH: 18
<212> TYPE: PRT
<213> ORGANISM: Strongylocentrotus purpuratus

<400> SEQUENCE: 79

Val Arg Arg Gln Asn Asp Thr Lys Lys Ala Val Lys Tyr Gln Ser Lys
1               5                   10                  15

Ala Arg

<210> SEQ ID NO 80
<211> LENGTH: 18
<212> TYPE: PRT
<213> ORGANISM: Aplysia sp.

<400> SEQUENCE: 80

Glu Thr Ala Lys Met Asp Thr Lys Lys Ala Val Lys Tyr Gln Ser Lys
1               5                   10                  15

Ala Arg

<210> SEQ ID NO 81
<211> LENGTH: 18
<212> TYPE: PRT
<213> ORGANISM: Teuthoida sp.

<400> SEQUENCE: 81

Glu Thr Ala Lys Val Asp Thr Lys Lys Ala Val Lys Tyr Gln Ser Lys
1               5                   10                  15

Ala Arg

<210> SEQ ID NO 82
<211> LENGTH: 18
<212> TYPE: PRT
<213> ORGANISM: Drosophila sp.

<400> SEQUENCE: 82

Gln Thr Ala Thr Gln Asp Thr Lys Lys Ala Leu Lys Tyr Gln Ser Lys
1               5                   10                  15

Ala Arg

<210> SEQ ID NO 83
<211> LENGTH: 18
<212> TYPE: PRT
<213> ORGANISM: Hirudinida sp.

<400> SEQUENCE: 83

Glu Thr Ala Ala Ala Asp Thr Lys Lys Ala Met Lys Tyr Gln Ser Ala
1               5                   10                  15

Ala Arg

<210> SEQ ID NO 84
<211> LENGTH: 5
<212> TYPE: PRT
```

<213> ORGANISM: Artificial Sequence
<220> FEATURE:
<223> OTHER INFORMATION: synthetic construct

<400> SEQUENCE: 84

Gly Gly Gly Gly Ser
 1               5

<210> SEQ ID NO 85
<211> LENGTH: 1002
<212> TYPE: DNA
<213> ORGANISM: Artificial Sequence
<220> FEATURE:
<223> OTHER INFORMATION: synthetic construct
<221> NAME/KEY: CDS
<222> LOCATION: (1)...(1002)

<400> SEQUENCE: 85

```
atg gct agc aaa gga gaa gaa ctc ttc act gga gtt gtc cca att ctt      48
Met Ala Ser Lys Gly Glu Glu Leu Phe Thr Gly Val Val Pro Ile Leu
 1               5                  10                  15 gtt gaa tta gat ggt gat gtt aac ggc cac aag ttc tct gtc agt gga      96
Val Glu Leu Asp Gly Asp Val Asn Gly His Lys Phe Ser Val Ser Gly
                 20                  25                  30 gag ggt gaa ggt gat gca aca tac gga aaa ctt acc ctg aag ttc atc     144
Glu Gly Glu Gly Asp Ala Thr Tyr Gly Lys Leu Thr Leu Lys Phe Ile
             35                  40                  45 tgc act act ggc aaa ctg cct gtt cca tgg cca aca cta gtc act act     192
Cys Thr Thr Gly Lys Leu Pro Val Pro Trp Pro Thr Leu Val Thr Thr
         50                  55                  60 ctg tgc tat ggt gtt caa tgc ttt tca aga tac ccg gat cat atg aaa     240
Leu Cys Tyr Gly Val Gln Cys Phe Ser Arg Tyr Pro Asp His Met Lys
 65                  70                  75                  80 cgg cat gac ttt ttc aag agt gcc atg ccc gaa ggt tat gta cag gaa     288
Arg His Asp Phe Phe Lys Ser Ala Met Pro Glu Gly Tyr Val Gln Glu
                 85                  90                  95 agg acc atc ttc ttc aaa gat gac ggc aac tac aag aca cgt gct gaa     336
Arg Thr Ile Phe Phe Lys Asp Asp Gly Asn Tyr Lys Thr Arg Ala Glu
            100                 105                 110 gtc aag ttt gaa ggt gat acc ctt gtt aat aga atc gag tta aaa ggt     384
Val Lys Phe Glu Gly Asp Thr Leu Val Asn Arg Ile Glu Leu Lys Gly
        115                 120                 125 att gac ttc aag gaa gat ggc aac att ctg gga cac aaa ttg gaa tac     432
Ile Asp Phe Lys Glu Asp Gly Asn Ile Leu Gly His Lys Leu Glu Tyr
    130                 135                 140 aac tat aac tca cac aat gta tac atc atg gca gac aaa caa aag aat     480
Asn Tyr Asn Ser His Asn Val Tyr Ile Met Ala Asp Lys Gln Lys Asn
145                 150                 155                 160 gga atc aaa gtg aac ttc aag acc cgc cac aac att gaa gat gga agc     528
Gly Ile Lys Val Asn Phe Lys Thr Arg His Asn Ile Glu Asp Gly Ser
                165                 170                 175 gtt caa cta gca gac cat tat caa caa aat act cca att ggc gat ggc     576
Val Gln Leu Ala Asp His Tyr Gln Gln Asn Thr Pro Ile Gly Asp Gly
            180                 185                 190 cct gtc ctt tta cca gac aac cat tac ctg tcc aca caa tct gcc ctt     624
Pro Val Leu Leu Pro Asp Asn His Tyr Leu Ser Thr Gln Ser Ala Leu
        195                 200                 205 tcg aaa gat ccc aac gaa aag aga gac cac atg gtc ctt ctt gag ttt     672
Ser Lys Asp Pro Asn Glu Lys Arg Asp His Met Val Leu Leu Glu Phe
    210                 215                 220 gta aca gct gct ggg att aca cat ggc atg gat gaa ctg tac aac ggc     720
Val Thr Ala Ala Gly Ile Thr His Gly Met Asp Glu Leu Tyr Asn Gly
```

```
                225                 230                 235                 240
ggt gca gga tcc ggt gcg ggt ggc ggt ggc atc cgg agg gta aca aac         768
Gly Ala Gly Ser Gly Ala Gly Gly Gly Gly Ile Arg Arg Val Thr Asn
                245                 250                 255 gat gcc cgg gaa aat gag atg gat gag aac ctg gag cag gtg agc ggc         816
Asp Ala Arg Glu Asn Glu Met Asp Glu Asn Leu Glu Gln Val Ser Gly
            260                 265                 270 atc atc gga aac ctc cgc cat atg gct cta gac atg ggc aat gag att         864
Ile Ile Gly Asn Leu Arg His Met Ala Leu Asp Met Gly Asn Glu Ile
        275                 280                 285 gac acc cag aat cgc cag atc gac agg atc atg gag aag gct gat tcc         912
Asp Thr Gln Asn Arg Gln Ile Asp Arg Ile Met Glu Lys Ala Asp Ser
    290                 295                 300 aac aaa acc aga att gat gaa gcc aac caa cgt gca aca aag atg ctg         960
Asn Lys Thr Arg Ile Asp Glu Ala Asn Gln Arg Ala Thr Lys Met Leu
305                 310                 315                 320 gga agt ggt ggc ggt ggc ggc cat cac cat cac cat cac taa                1002
Gly Ser Gly Gly Gly Gly Gly His His His His His His *
                325                 330

<210> SEQ ID NO 86
<211> LENGTH: 333
<212> TYPE: PRT
<213> ORGANISM: Artificial Sequence
<220> FEATURE:
<223> OTHER INFORMATION: synthetic construct

<400> SEQUENCE: 86

Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Cys Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Gly
```

```
                    225                 230                 235                 240
Gly Ala Gly Ser Gly Ala Gly Gly Gly Ile Arg Arg Val Thr Asn
                245                 250                 255

Asp Ala Arg Glu Asn Glu Met Asp Glu Asn Leu Glu Gln Val Ser Gly
            260                 265                 270

Ile Ile Gly Asn Leu Arg His Met Ala Leu Asp Met Gly Asn Glu Ile
        275                 280                 285

Asp Thr Gln Asn Arg Gln Ile Asp Arg Ile Met Glu Lys Ala Asp Ser
    290                 295                 300

Asn Lys Thr Arg Ile Asp Glu Ala Asn Gln Arg Ala Thr Lys Met Leu
305                 310                 315                 320

Gly Ser Gly Gly Gly Gly His His His His His
                325                 330

<210> SEQ ID NO 87
<211> LENGTH: 1044
<212> TYPE: DNA
<213> ORGANISM: Artificial Sequence
<220> FEATURE:
<223> OTHER INFORMATION: synthetic construct
<221> NAME/KEY: CDS
<222> LOCATION: (1)...(1044)

<400> SEQUENCE: 87 atg gct agc gga gga ctg aac gac atc ttc gag gct caa aag atc gag      48
Met Ala Ser Gly Gly Leu Asn Asp Ile Phe Glu Ala Gln Lys Ile Glu
  1               5                  10                  15 tgg cat gga tcc cat cat cat cat cat cat cat atc cgg agg gta          96
Trp His Gly Ser His His His His His His His Ile Arg Arg Val
                 20                  25                  30 aca aac gat gcc cgg gaa aat gag atg gat gag aac ctg gag cag gtg     144
Thr Asn Asp Ala Arg Glu Asn Glu Met Asp Glu Asn Leu Glu Gln Val
             35                  40                  45 agc ggc atc atc gga aac ctc cgc cat atg gct cta gac atg ggc aat     192
Ser Gly Ile Ile Gly Asn Leu Arg His Met Ala Leu Asp Met Gly Asn
         50                  55                  60 gag att gac acc cag aat cgc cag atc gac agg atc atg gag aag gct     240
Glu Ile Asp Thr Gln Asn Arg Gln Ile Asp Arg Ile Met Glu Lys Ala
 65                  70                  75                  80 gat tcc aac aaa acc aga att gat gaa gcc aac caa cgt gca aca aag     288
Asp Ser Asn Lys Thr Arg Ile Asp Glu Ala Asn Gln Arg Ala Thr Lys
                 85                  90                  95 atg ctg gga agt ggt ggc ggt ggt agc ggc acc ggt ggc gct agc aaa     336
Met Leu Gly Ser Gly Gly Gly Gly Ser Gly Thr Gly Gly Ala Ser Lys
            100                 105                 110 gga gaa gaa ctc ttc act gga gtt gtc cca att ctt gtt gaa tta gat     384
Gly Glu Glu Leu Phe Thr Gly Val Val Pro Ile Leu Val Glu Leu Asp
        115                 120                 125 ggt gat gtt aac ggc cac aag ttc tct gtc agt gga gag ggt gaa ggt     432
Gly Asp Val Asn Gly His Lys Phe Ser Val Ser Gly Glu Gly Glu Gly
    130                 135                 140 gat gca aca tac gga aaa ctt acc ctg aag ttc atc tgc act act ggc     480
Asp Ala Thr Tyr Gly Lys Leu Thr Leu Lys Phe Ile Cys Thr Thr Gly
145                 150                 155                 160 aaa ctg cct gtt cca tgg cca aca cta gtc act act ctg tgc tat ggt     528
Lys Leu Pro Val Pro Trp Pro Thr Leu Val Thr Thr Leu Cys Tyr Gly
                165                 170                 175 gtt caa tgc ttt tca aga tac ccg gat cat atg aaa cgg cat gac ttt     576
Val Gln Cys Phe Ser Arg Tyr Pro Asp His Met Lys Arg His Asp Phe
            180                 185                 190
```

```
ttc aag agt gcc atg ccc gaa ggt tat gta cag gaa agg acc atc ttc      624
Phe Lys Ser Ala Met Pro Glu Gly Tyr Val Gln Glu Arg Thr Ile Phe
        195                 200                 205 ttc aaa gat gac ggc aac tac aag aca cgt gct gaa gtc aag ttt gaa      672
Phe Lys Asp Asp Gly Asn Tyr Lys Thr Arg Ala Glu Val Lys Phe Glu
210                 215                 220 ggt gat acc ctt gtt aat aga atc gag tta aaa ggt att gac ttc aag      720
Gly Asp Thr Leu Val Asn Arg Ile Glu Leu Lys Gly Ile Asp Phe Lys
225                 230                 235                 240 gaa gat ggc aac att ctg gga cac aaa ttg gaa tac aac tat aac tca      768
Glu Asp Gly Asn Ile Leu Gly His Lys Leu Glu Tyr Asn Tyr Asn Ser
            245                 250                 255 cac aat gta tac atc atg gca gac aaa caa aag aat gga atc aaa gtg      816
His Asn Val Tyr Ile Met Ala Asp Lys Gln Lys Asn Gly Ile Lys Val
        260                 265                 270 aac ttc aag acc cgc cac aac att gaa gat gga agc gtt caa cta gca      864
Asn Phe Lys Thr Arg His Asn Ile Glu Asp Gly Ser Val Gln Leu Ala
    275                 280                 285 gac cat tat caa caa aat act cca att ggc gat ggc cct gtc ctt tta      912
Asp His Tyr Gln Gln Asn Thr Pro Ile Gly Asp Gly Pro Val Leu Leu
290                 295                 300 cca gac aac cat tac ctg tcc aca caa tct gcc ctt tcg aaa gat ccc      960
Pro Asp Asn His Tyr Leu Ser Thr Gln Ser Ala Leu Ser Lys Asp Pro
305                 310                 315                 320 aac gaa aag aga gac cac atg gtc ctt ctt gag ttt gta aca gct gct     1008
Asn Glu Lys Arg Asp His Met Val Leu Leu Glu Phe Val Thr Ala Ala
            325                 330                 335 ggg att aca cat ggc atg gat gaa ctg tac aac tga                     1044
Gly Ile Thr His Gly Met Asp Glu Leu Tyr Asn  *
        340                 345

<210> SEQ ID NO 88
<211> LENGTH: 347
<212> TYPE: PRT
<213> ORGANISM: Artificial Sequence
<220> FEATURE:
<223> OTHER INFORMATION: synthetic construct

<400> SEQUENCE: 88

Met Ala Ser Gly Gly Leu Asn Asp Ile Phe Glu Ala Gln Lys Ile Glu
 1               5                  10                  15

Trp His Gly Ser His His His His His His Ile Arg Arg Val
            20                  25                  30

Thr Asn Asp Ala Arg Glu Asn Glu Met Asp Glu Asn Leu Glu Gln Val
        35                  40                  45

Ser Gly Ile Ile Gly Asn Leu Arg His Met Ala Leu Asp Met Gly Asn
    50                  55                  60

Glu Ile Asp Thr Gln Asn Arg Gln Ile Asp Arg Ile Met Glu Lys Ala
65                  70                  75                  80

Asp Ser Asn Lys Thr Arg Ile Asp Glu Ala Asn Gln Arg Ala Thr Lys
                85                  90                  95

Met Leu Gly Ser Gly Gly Gly Ser Gly Thr Gly Ala Ser Lys
            100                 105                 110

Gly Glu Glu Leu Phe Thr Gly Val Val Pro Ile Leu Val Glu Leu Asp
        115                 120                 125

Gly Asp Val Asn Gly His Lys Phe Ser Val Ser Gly Glu Gly Glu Gly
    130                 135                 140

Asp Ala Thr Tyr Gly Lys Leu Thr Leu Lys Phe Ile Cys Thr Thr Gly
```

-continued

```
            145                 150                 155                 160
Lys Leu Pro Val Pro Trp Pro Thr Leu Val Thr Thr Leu Cys Tyr Gly
                165                 170                 175

Val Gln Cys Phe Ser Arg Tyr Pro Asp His Met Lys Arg His Asp Phe
            180                 185                 190

Phe Lys Ser Ala Met Pro Glu Gly Tyr Val Gln Glu Arg Thr Ile Phe
        195                 200                 205

Phe Lys Asp Asp Gly Asn Tyr Lys Thr Arg Ala Glu Val Lys Phe Glu
    210                 215                 220

Gly Asp Thr Leu Val Asn Arg Ile Glu Leu Lys Gly Ile Asp Phe Lys
225                 230                 235                 240

Glu Asp Gly Asn Ile Leu Gly His Lys Leu Glu Tyr Asn Tyr Asn Ser
                245                 250                 255

His Asn Val Tyr Ile Met Ala Asp Lys Gln Lys Asn Gly Ile Lys Val
            260                 265                 270

Asn Phe Lys Thr Arg His Asn Ile Glu Asp Gly Ser Val Gln Leu Ala
        275                 280                 285

Asp His Tyr Gln Gln Asn Thr Pro Ile Gly Asp Gly Pro Val Leu Leu
    290                 295                 300

Pro Asp Asn His Tyr Leu Ser Thr Gln Ser Ala Leu Ser Lys Asp Pro
305                 310                 315                 320

Asn Glu Lys Arg Asp His Met Val Leu Leu Glu Phe Val Thr Ala Ala
                325                 330                 335

Gly Ile Thr His Gly Met Asp Glu Leu Tyr Asn
            340                 345
```

```
<210> SEQ ID NO 89
<211> LENGTH: 2040
<212> TYPE: DNA
<213> ORGANISM: Artificial Sequence
<220> FEATURE:
<223> OTHER INFORMATION: synthetic construct
<221> NAME/KEY: CDS
<222> LOCATION: (164)...(784)

<400> SEQUENCE: 89
```

```
cccgaggttt ggagctgtct ttccttccct ccctacccgg cggctcctcc actcttgcta      60
cctgcaggga tcagcggaca gcatcctctg aagaagacaa ggttccttaa ctaagcacca     120
ctgacttgct ggccccggcg cccagcaacc cccaccact acc atg gcc gag gac        175
                                              Met Ala Glu Asp
                                                1 gca gac atg cgt aat gaa ctg gag gag atg cag agg agg gct gac cag       223
Ala Asp Met Arg Asn Glu Leu Glu Glu Met Gln Arg Arg Ala Asp Gln
  5              10                  15                  20 ctg gct gat gag tcc ctg gaa agc acc cgt cgc atg ctg cag ctg gtc       271
Leu Ala Asp Glu Ser Leu Glu Ser Thr Arg Arg Met Leu Gln Leu Val
             25                  30                  35 gaa gag agt aaa gat gct ggc atc agg act ttg gtt atg ttg gat gag       319
Glu Glu Ser Lys Asp Ala Gly Ile Arg Thr Leu Val Met Leu Asp Glu
         40                  45                  50 caa ggc gaa caa ctg gaa cgc att gag gaa ggg atg gac caa atc aat       367
Gln Gly Glu Gln Leu Glu Arg Ile Glu Glu Gly Met Asp Gln Ile Asn
     55                  60                  65 aag gat atg aaa gaa gca gaa aag aat ttg acg gac cta gga aaa ttc       415
Lys Asp Met Lys Glu Ala Glu Lys Asn Leu Thr Asp Leu Gly Lys Phe
 70                  75                  80 tgc ggg ctt tgt gtg tgt ccc tgt aac aag ctt aaa tcc agt gat gct       463
```

|  |  |  |  |  |  |  |  |  |  |  |  |  |  |  |  |
|---|---|---|---|---|---|---|---|---|---|---|---|---|---|---|---|
| Cys | Gly | Leu | Cys | Val | Cys | Pro | Cys | Asn | Lys | Leu | Lys | Ser | Ser | Asp | Ala |
| 85 |  |  |  | 90 |  |  |  | 95 |  |  |  | 100 |  |  |  |

| tac | aaa | aaa | gcc | tgg | ggc | aat | aat | cag | gat | gga | gta | gtg | gcc | agc | cag | 511 |
|---|---|---|---|---|---|---|---|---|---|---|---|---|---|---|---|---|
| Tyr | Lys | Lys | Ala | Trp | Gly | Asn | Asn | Gln | Asp | Gly | Val | Val | Ala | Ser | Gln |  |
|  |  |  |  | 105 |  |  |  |  | 110 |  |  |  |  | 115 |  |  |

| cct | gcc | cgt | gtg | gtg | gat | gaa | cgg | gag | cag | atg | gcc | atc | agt | ggt | ggc | 559 |
|---|---|---|---|---|---|---|---|---|---|---|---|---|---|---|---|---|
| Pro | Ala | Arg | Val | Val | Asp | Glu | Arg | Glu | Gln | Met | Ala | Ile | Ser | Gly | Gly |  |
|  |  |  | 120 |  |  |  |  | 125 |  |  |  |  | 130 |  |  |  |

| ttc | atc | cgc | agg | gta | aca | aac | gat | gcc | cgg | gaa | aat | gaa | atg | gat | gaa | 607 |
|---|---|---|---|---|---|---|---|---|---|---|---|---|---|---|---|---|
| Phe | Ile | Arg | Arg | Val | Thr | Asn | Asp | Ala | Arg | Glu | Asn | Glu | Met | Asp | Glu |  |
|  |  |  | 135 |  |  |  |  | 140 |  |  |  |  | 145 |  |  |  |

| aac | cta | gag | cag | gtg | agc | ggc | atc | atc | gga | aac | ctc | cgt | cat | atg | gcc | 655 |
|---|---|---|---|---|---|---|---|---|---|---|---|---|---|---|---|---|
| Asn | Leu | Glu | Gln | Val | Ser | Gly | Ile | Ile | Gly | Asn | Leu | Arg | His | Met | Ala |  |
|  |  | 150 |  |  |  |  | 155 |  |  |  |  | 160 |  |  |  |  |

| cta | gac | atg | ggc | aat | gag | att | gac | acc | cag | aat | cgc | cag | att | gac | agg | 703 |
|---|---|---|---|---|---|---|---|---|---|---|---|---|---|---|---|---|
| Leu | Asp | Met | Gly | Asn | Glu | Ile | Asp | Thr | Gln | Asn | Arg | Gln | Ile | Asp | Arg |  |
| 165 |  |  |  |  | 170 |  |  |  |  | 175 |  |  |  |  | 180 |  |

| atc | atg | gag | aag | gct | gac | tcc | aac | aaa | acc | aga | att | gat | gaa | gcc | aac | 751 |
|---|---|---|---|---|---|---|---|---|---|---|---|---|---|---|---|---|
| Ile | Met | Glu | Lys | Ala | Asp | Ser | Asn | Lys | Thr | Arg | Ile | Asp | Glu | Ala | Asn |  |
|  |  |  |  | 185 |  |  |  |  | 190 |  |  |  |  | 195 |  |  |

| caa | cgt | gca | aca | aag | atg | ctg | gga | agt | ggt | taa | atctgccgtt | ctgctgtgct | 804 |
|---|---|---|---|---|---|---|---|---|---|---|---|---|---|
| Gln | Arg | Ala | Thr | Lys | Met | Leu | Gly | Ser | Gly | * |  |  |  |
|  |  | 200 |  |  |  |  | 205 |  |  |  |  |  |  |

| | |
|---|---|
| gtcctccaat gttgttggac aagagagaag agagctcctt catgcttctc tcatggtatt | 864 |
| acctagtaag acttacacac acacacacac acacacacac acacacacac acacacacac | 924 |
| acacacagag tagtcacccc cattgtaaat gtctgtgtgg tttgtcagct tcccaatgat | 984 |
| accatgtgtc ttttgttttc tccggctctc tttctttgcc aaaggttgta catagtggtc | 1044 |
| atctggtgac tctatttcct gacttaagag ttcttgggtc tctctctttc ttttctcagt | 1104 |
| ggcgtttgct gaatgacaac aatttaggaa tgctcaatgt actgttgatt tttctcaata | 1164 |
| cacagtattg ttcttgtaaa actgtgactt accacagagc tactaccaca gtcctttctt | 1224 |
| agggtgtcag gctctgaatc tctccaaatg tgctctcttt ggttcctcag tgctattctt | 1284 |
| tgtctttatg atttcataat tagacaatgt gaaattacat aacaggcatt gcactaaaag | 1344 |
| tgatgtgatt tatgcattta tgcatgagaa ctaaatagac ttttagatcc tacttaaaca | 1404 |
| aaaacttcca tgacagtagc atactgacaa gaaaacacac acaacagcaa caataacaaa | 1464 |
| gcaacaacta cgcatgctca gcattgggac actgtcaaga ttaagtcata ccagcaaaac | 1524 |
| ctgcagctgt gtcaccttct tctgtcaaca tacagactga tcataatgat cccttcttta | 1584 |
| cacacacaca cacacacaca cacacacaca cacacacaaa tggaatttaa ccaacttccc | 1644 |
| agaattgatg aagcaaatat atgtttggct gaaactattg taaatgggtg taatataggg | 1704 |
| tttgtcgaat gcttttgaaa gctctgtttt ccagacaata ctcttgtgtg gaaaacgtga | 1764 |
| agatcttcta agtctggctc ttgtgatcac caaaccctgg tgcatcagta caacactttg | 1824 |
| cgctaatcta gagctatgca caaccaaatt gctgagatgt ttagtagctg ataaagaaac | 1884 |
| ctttaaaaaa ttatataaat gaatgaaata tagataaact gtgagataaa tatcattaca | 1944 |
| gcatgtatat taaatccctc ctgtctcctc tgttggtttg tgaagtgatt tgacattttg | 2004 |
| tagctagttt aaaattatta aaaattatag atgtta | 2040 |

<210> SEQ ID NO 90
<211> LENGTH: 206
<212> TYPE: PRT
<213> ORGANISM: Artificial Sequence
<220> FEATURE:

<223> OTHER INFORMATION: synthetic construct

<400> SEQUENCE: 90

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
            195                 200                 205

<210> SEQ ID NO 91
<211> LENGTH: 8
<212> TYPE: PRT
<213> ORGANISM: Artificial Sequence
<220> FEATURE:
<223> OTHER INFORMATION: synthetic construct

<400> SEQUENCE: 91

Asp Tyr Lys Asp Asp Asp Asp Lys
1               5

<210> SEQ ID NO 92
<211> LENGTH: 9
<212> TYPE: PRT
<213> ORGANISM: Artificial Sequence
<220> FEATURE:
<223> OTHER INFORMATION: synthetic construct

<400> SEQUENCE: 92

Tyr Pro Tyr Asp Val Pro Asp Tyr Ala
1               5

<210> SEQ ID NO 93
<211> LENGTH: 10
<212> TYPE: PRT
<213> ORGANISM: Artificial Sequence
<220> FEATURE:
<223> OTHER INFORMATION: synthetic construct

<400> SEQUENCE: 93

```
<210> SEQ ID NO 94
<211> LENGTH: 6
<212> TYPE: PRT
<213> ORGANISM: Artificial Sequence
<220> FEATURE:
<223> OTHER INFORMATION: synthetic construct

<400> SEQUENCE: 94

Asp Thr Tyr Arg Tyr Ile
 1               5

<210> SEQ ID NO 95
<211> LENGTH: 6
<212> TYPE: PRT
<213> ORGANISM: Artificial Sequence
<220> FEATURE:
<223> OTHER INFORMATION: synthetic construct

<400> SEQUENCE: 95

His His His His His His
 1               5

<210> SEQ ID NO 96
<211> LENGTH: 118
<212> TYPE: PRT
<213> ORGANISM: Homo sapiens

<400> SEQUENCE: 96

Met Ser Ala Pro Ala Gln Pro Pro Ala Glu Gly Thr Glu Gly Thr Ala
 1               5                  10                  15

Pro Gly Gly Gly Pro Pro Gly Pro Pro Pro Asn Met Thr Ser Asn Arg
                20                  25                  30

Arg Leu Gln Gln Thr Gln Ala Gln Val Glu Glu Val Val Asp Ile Ile
            35                  40                  45

Arg Val Asn Val Asp Lys Val Leu Glu Arg Asp Gln Lys Leu Ser Glu
        50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
                100                 105                 110

Val Ile Tyr Phe Phe Thr
            115
```

```
<210> SEQ ID NO 97
<211> LENGTH: 714
<212> TYPE: DNA
<213> ORGANISM: Aequorea victoria
<220> FEATURE:
<221> NAME/KEY: CDS
<222> LOCATION: (1)...(714)

<400> SEQUENCE: 97 atg agt aaa gga gaa gaa ctt ttc act gga gtt gtc cca att ctt gtt      48
Met Ser Lys Gly Glu Glu Leu Phe Thr Gly Val Val Pro Ile Leu Val
 1               5                  10                  15 gaa tta gat ggt gat gtt aat ggg caa aaa ttc tct gtc agg gga gag      96
Glu Leu Asp Gly Asp Val Asn Gly Gln Lys Phe Ser Val Arg Gly Glu
                20                  25                  30
```

```
ggt gaa ggt gat gca aca tac gga aaa ctt acc ctt aaa ttt att tgc    144
Gly Glu Gly Asp Ala Thr Tyr Gly Lys Leu Thr Leu Lys Phe Ile Cys
         35                  40                  45 act act ggg aag cta cct gtt cca tgg cca aca ctt gtc act act ttc    192
Thr Thr Gly Lys Leu Pro Val Pro Trp Pro Thr Leu Val Thr Thr Phe
 50                  55                  60 tct tat ggt gta caa tgc ttc tca aga tac cca gat cat atg aaa cag    240
Ser Tyr Gly Val Gln Cys Phe Ser Arg Tyr Pro Asp His Met Lys Gln
 65                  70                  75                  80 cat gac ttt ctc aag agt gcc atg ccc gaa ggt tat gta cag gaa aga    288
His Asp Phe Leu Lys Ser Ala Met Pro Glu Gly Tyr Val Gln Glu Arg
                 85                  90                  95 act ata ttt tac aaa gat gac ggg aac tac aag aca cgt gct gaa gtc    336
Thr Ile Phe Tyr Lys Asp Asp Gly Asn Tyr Lys Thr Arg Ala Glu Val
             100                 105                 110 aag ttt gag ggt gat acc ctt gtt aat aga atc gag tta aaa ggt att    384
Lys Phe Glu Gly Asp Thr Leu Val Asn Arg Ile Glu Leu Lys Gly Ile
         115                 120                 125 gat ttt aaa gaa gat gga aac att ctt gga cac aaa atg gaa tac aac    432
Asp Phe Lys Glu Asp Gly Asn Ile Leu Gly His Lys Met Glu Tyr Asn
130                 135                 140 tat aac tca cat aat gta tac atc atg gga gac aaa cca aag aat ggc    480
Tyr Asn Ser His Asn Val Tyr Ile Met Gly Asp Lys Pro Lys Asn Gly
145                 150                 155                 160 atc aaa gtt aac ttc aaa att aga cac aac att aaa gat gga agc gtt    528
Ile Lys Val Asn Phe Lys Ile Arg His Asn Ile Lys Asp Gly Ser Val
                 165                 170                 175 caa tta gca gac cat tat caa caa aat act cca att ggc gat ggc cct    576
Gln Leu Ala Asp His Tyr Gln Gln Asn Thr Pro Ile Gly Asp Gly Pro
             180                 185                 190 gtc ctt tta cca gac aac cat tac ctg tcc aca caa tct gcc ctt tcc    624
Val Leu Leu Pro Asp Asn His Tyr Leu Ser Thr Gln Ser Ala Leu Ser
         195                 200                 205 caa gat ccc cac gga aag aga gat cac atg gtc ctt ctt gag ttt gtt    672
Gln Asp Pro His Gly Lys Arg Asp His Met Val Leu Leu Glu Phe Val
210                 215                 220 aca tct gct ggg att aca cat ggc atg gat gaa cta tac aaa            714
Thr Ser Ala Gly Ile Thr His Gly Met Asp Glu Leu Tyr Lys
225                 230                 235

<210> SEQ ID NO 98
<211> LENGTH: 238
<212> TYPE: PRT
<213> ORGANISM: Aequorea victoria

<400> SEQUENCE: 98

Met Ser Lys Gly Glu Glu Leu Phe Thr Gly Val Val Pro Ile Leu Val
 1               5                  10                  15

Glu Leu Asp Gly Asp Val Asn Gly Gln Lys Phe Ser Val Arg Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
 50                  55                  60

Ser Tyr Gly Val Gln Cys Phe Ser Arg Tyr Pro Asp His Met Lys Gln
 65                  70                  75                  80

His Asp Phe Leu Lys Ser Ala Met Pro Glu Gly Tyr Val Gln Glu Arg
                 85                  90                  95
```

```
Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

Tyr Asn Ser His Asn Val Tyr Ile Met Gly Asp Lys Pro Lys Asn Gly
145                 150                 155                 160

Ile Lys Val Asn Phe Lys Ile Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Gln Asp Pro His Gly Lys Arg Asp His Met Val Leu Leu Glu Phe Val
    210                 215                 220

Thr Ser Ala Gly Ile Thr His Gly Met Asp Glu Leu Tyr Lys
225                 230                 235
```

<210> SEQ ID NO 99
<211> LENGTH: 6
<212> TYPE: PRT
<213> ORGANISM: Artificial Sequence
<220> FEATURE:
<223> OTHER INFORMATION: synthetic construct
<221> NAME/KEY: VARIANT
<222> LOCATION: 3,4
<223> OTHER INFORMATION: Xaa=any amino acid

<400> SEQUENCE: 99

```
Cys Cys Xaa Xaa Cys Cys
1               5
```

<210> SEQ ID NO 100
<211> LENGTH: 6
<212> TYPE: PRT
<213> ORGANISM: Artificial Sequence
<220> FEATURE:
<223> OTHER INFORMATION: synthetic construct

<400> SEQUENCE: 100

```
Cys Cys Pro Gly Cys Cys
1               5
```

<210> SEQ ID NO 101
<211> LENGTH: 24
<212> TYPE: DNA
<213> ORGANISM: Artificial Sequence
<220> FEATURE:
<223> OTHER INFORMATION: primer

<400> SEQUENCE: 101
atccggaggg taacaaacga tgcc                                              24

<210> SEQ ID NO 102
<211> LENGTH: 60
<212> TYPE: DNA
<213> ORGANISM: Artificial Sequence
<220> FEATURE:
<223> OTHER INFORMATION: primer

<400> SEQUENCE: 102
cgaattccgc gggccaccat gggaggagga ctgaacgaca tcttcgaggc tcaaaagatc      60

<210> SEQ ID NO 103
<211> LENGTH: 79
<212> TYPE: DNA
<213> ORGANISM: Artificial Sequence
<220> FEATURE:
<223> OTHER INFORMATION: primer

<400> SEQUENCE: 103
tcgtttgtta ccctccggat atgatgatga tgatgatgat gatgggatcc atgccactcg    60
atcttttgag cctcgaaga                                                 79

<210> SEQ ID NO 104
<211> LENGTH: 36
<212> TYPE: DNA
<213> ORGANISM: Artificial Sequence
<220> FEATURE:
<223> OTHER INFORMATION: primer

<400> SEQUENCE: 104
gctagatctc gagttaacca cttcccagca tctttg                              36

<210> SEQ ID NO 105
<211> LENGTH: 30
<212> TYPE: DNA
<213> ORGANISM: Artificial Sequence
<220> FEATURE:
<223> OTHER INFORMATION: primer

<400> SEQUENCE: 105
cgaagatctg gaggactgaa cgacatcttc                                     30

<210> SEQ ID NO 106
<211> LENGTH: 33
<212> TYPE: DNA
<213> ORGANISM: Artificial Sequence
<220> FEATURE:
<223> OTHER INFORMATION: synthetic construct

<400> SEQUENCE: 106
gatgaagcca accaagctgc aacaaagatg ctg                                 33

<210> SEQ ID NO 107
<211> LENGTH: 31
<212> TYPE: DNA
<213> ORGANISM: Artificial Sequence
<220> FEATURE:
<223> OTHER INFORMATION: synthetic construct

<400> SEQUENCE: 107
cgccagatcg acgatatcat ggagaaggct g                                   31

<210> SEQ ID NO 108
<211> LENGTH: 10
<212> TYPE: PRT
<213> ORGANISM: Artificial Sequence
<220> FEATURE:
<223> OTHER INFORMATION: synthetic construct

<400> SEQUENCE: 108

His His His His His His His His His His
 1               5                  10

<210> SEQ ID NO 109
<211> LENGTH: 18

```
<212> TYPE: PRT
<213> ORGANISM: Clostridium sp.

<400> SEQUENCE: 109

Ser Asn Arg Thr Arg Ile Asp Glu Ala Asn Gln Arg Ala Thr Arg Met
1               5                   10                  15

Leu Gly

<210> SEQ ID NO 110
<211> LENGTH: 35
<212> TYPE: PRT
<213> ORGANISM: Clostridium sp.

<400> SEQUENCE: 110

Leu Ser Glu Leu Asp Asp Arg Ala Asp Ala Leu Gln Ala Gly Ala Ser
1               5                   10                  15

Gln Ph

-continued

```
<213> ORGANISM: Clostridium sp.

<400> SEQUENCE: 113

Asn Lys Leu Lys Ser Ser Asp Ala Tyr Lys Lys Ala Trp Gly Asn Asn
1               5                   10                  15

Gln Asp Gly Val Val Ala Ser Gln Pro Ala Arg Val Val Asp Glu Arg
            20                  25                  30

Glu Gln Met Ala Ile Ser Gly Gly Phe Ile Arg Arg Val Thr Asn Asp
        35                  40                  45

Ala Arg Glu Asn Glu Met Asp Glu Asn Leu Glu Gln Val Ser Gly Ile
    50                  55                  60

Ile Gly Asn Leu Arg His Met Ala Leu Asp Met Gly Asn Glu Ile Asp
65                  70                  75                  80

Thr Gln Asn Arg Gln Ile Asp Arg Ile Met Glu Lys Ala Asp Ser Asn
                85                  90                  95

Lys Thr Arg Ile Asp Glu Ala Asn Gln Ala Ala Thr Lys Met Leu Gly
            100                 105                 110

Ser Gly
```